US009650672B2

(12) United States Patent
Bjornson

(10) Patent No.: US 9,650,672 B2
(45) Date of Patent: May 16, 2017

(54) ENZYMES RESISTANT TO PHOTODAMAGE

(71) Applicant: Pacific Biosciences of California, Inc., Menlo Park, CA (US)

(72) Inventor: Keith Bjornson, Fremont, CA (US)

(73) Assignee: Pacific Biosciences of California, Inc., Menlo Park, CA (US)

( * ) Notice: Subject to any disclaimer, the term of this patent is extended or adjusted under 35 U.S.C. 154(b) by 0 days.

(21) Appl. No.: 14/818,728

(22) Filed: Aug. 5, 2015

(65) Prior Publication Data

US 2016/0017413 A1    Jan. 21, 2016

Related U.S. Application Data

(62) Division of application No. 12/384,110, filed on Mar. 30, 2009, now Pat. No. 9,127,259.

(60) Provisional application No. 61/072,643, filed on Mar. 31, 2008.

(51) Int. Cl.
| | |
|---|---|
| *C12N 9/12* | (2006.01) |
| *C12Q 1/68* | (2006.01) |
| *C12P 19/34* | (2006.01) |

(52) U.S. Cl.
CPC ......... *C12Q 1/6869* (2013.01); *C12N 9/1252* (2013.01); *C12N 9/1276* (2013.01); *C12P 19/34* (2013.01)

(58) Field of Classification Search
None
See application file for complete search history.

(56) References Cited

U.S. PATENT DOCUMENTS

| | | | |
|---|---|---|---|
| 4,732,973 A | 3/1988 | Barr et al. | |
| 4,752,585 A | 6/1988 | Koths et al. | |
| 5,198,543 A | 3/1993 | Blanco et al. | |
| 5,346,823 A | 9/1994 | Estell et al. | |
| 5,614,365 A | 3/1997 | Tabor et al. | |
| 5,866,331 A * | 2/1999 | Singer ................ | C12Q 1/6841 250/459.1 |
| 6,596,486 B2 | 7/2003 | Frank-Kamenetskii et al. | |
| 6,917,726 B2 | 7/2005 | Levene et al. | |
| 7,033,764 B2 | 4/2006 | Korlach et al. | |
| 7,052,847 B2 | 5/2006 | Korlach et al. | |
| 7,056,661 B2 | 6/2006 | Korlach et al. | |
| 7,056,676 B2 | 6/2006 | Korlach et al. | |
| 7,993,895 B2 | 8/2011 | Eid et al. | |
| 8,415,128 B2 | 4/2013 | Eid et al. | |
| 8,501,992 B2 | 8/2013 | Kim et al. | |
| 8,834,847 B2 | 9/2014 | Yue et al. | |
| 2003/0044781 A1 | 3/2003 | Korlach et al. | |
| 2003/0174992 A1 * | 9/2003 | Levene ................ | B82Y 20/00 385/129 |
| 2007/0161017 A1 | 7/2007 | Eid et al. | |
| 2007/0196846 A1 | 8/2007 | Hanzel et al. | |
| 2008/0108082 A1 | 5/2008 | Rank et al. | |
| 2010/0261185 A1 | 10/2010 | Nikiforov et al. | |
| 2011/0014612 A1 | 1/2011 | Hendricks et al. | |

FOREIGN PATENT DOCUMENTS

| | | | |
|---|---|---|---|
| WO | 2002086088 A2 | 10/2002 | |
| WO | 2007064905 A2 | 7/2007 | |
| WO | 2007075987 A2 | 7/2007 | |

OTHER PUBLICATIONS

Guo et al. PNAS, vol. 101, pp. 9205-9210, 2004.*
Kapanidis and Weiss Journal of Chemical Physics vol. 117, pp. 10953-10964, 2001.*
Bernad et al. (1990) "Site-directed mutagenesis of the YCDTDS amino acid motif of the ψ29 DNA polymerase," Gene, 94:45-51.
Bernad et al. (1990) "The highly conserved amino acid sequence motif Tyr-Gly-Asp-Thr-Asp-Ser in a α-like DNA polymerases is required by phage ψ29 DNA polymerase for protein-primed initiation and polymerization," PNAS, 87:4610-4614.
Blanco et al. (1991) "A general structure for DNA-dependent DNA polymerases," Gene, 100:27-38.
Blasco et al. (1992) "Primer Terminus Stabilization at the ψ29 DNA Polymerase Active Site." The Journal of Biological Chemistry, 270(6): 2735-2740.
Blasco et al. (1992) "ψ29 DNA Polymerase Active Site." The Journal of Biological Chemistry, 267(27): 19427-19434.
Blasco et al. (1993) "Phi 29 DNA Polymerase Active Site. Residue ASP249 of Conserved Amino Acid Motif 'Dx2SLYP' is Critical for Synthetic Activities." J. Biol Chem., 268(32): 24106-13.
Bonnin et al. (1999) "A Single Tyrosine Prevents Insertion of Ribonucleotides in the Eukaryotic-type ψ29 DNA Polymerase." The Journal of Molecular Biology, 290: 241-251.
Bordo and Argos (1991) "Suggestions for 'safe' residue substitutions in site-directed mutagenesis," Journal of Molecular Biology, 217(4): 721-729.
Brautigam et al. (1999) "Structural elucidation of the binding and inhibitory properties of lanthanide (III) ions at the 3'-5' exonucleolytic active site of the Klenow frament," Chem. Biol., 6:901-908.
Dufour et al. (2003) "A conserved insertion in protein-primed DNA polymerases involved in primer terminus stabilisation," J. Mol. Biol., 331:781-794.
Eid et al., "Real-time DNA sequencing from single polymerase molecules" Science (2008) 323(5910):133-138.
Frey et al. (1996) "Elucidation of the metal-binding properties of the Kleow fragment of *Escherichia coli* polymerase I and bacteriophage T4 DNA polymerases by lanthanide (III) luminescence spectroscopy," Chem. Biol., 3:393-403.
Guo et al. (2004) "Protein Tolerance to Random Amino Acid Change", PNAS 101(25):9205-9210.

(Continued)

*Primary Examiner* — Richard Hutson
(74) *Attorney, Agent, or Firm* — Monicia Elrod-Erickson

(57) ABSTRACT

Provided are compositions comprising modified DNA polymerases that exhibit improved photostability compared to the parental polymerases from which they were derived. Provided are methods for generating enzymes, such as DNA polymerases, with the aforementioned phenotype. Provided are methods of using polymerases with increased resistance to photodamage to make a DNA or to sequence a DNA template.

16 Claims, 19 Drawing Sheets

(56) References Cited

OTHER PUBLICATIONS

Hayes et al. (2202) "Combing computational and experimental screening for rapid optimization of protein properties." Proceedings on the National Acadmey of Sciences, USA, 99(25):15926-15931.
Levene et al., "Zero mode waveguides for single molecule analysis at high concentrations" Science (2003) 299 (5607):682-686.
Ngo et al. in the Protein Folding Problem and Tertiary Structure Prediction, 1994, Merz et al. (ed.), Birkhauser, Boston, MA, pp. 433 and 492-495.
Rodriguez et al. (2003) "ψ29 DNA Polymerase Residue Phe128 of the Highly Conserved (S/T)Lx2h Motif is Required for a Stable and Functional Interaction with the Termial Protein." The Journal of Molecular Biology, 325: 85-97.
Shih et al. (2008) "Typtophan-accelerated electron flow though proteins." Science, 320(5884):1760-1762.
Truniger et al. (1996) "A DNA binding motif coordinating synthesis and degradation in proofreading DNA polymerases," Embo J., 15(13):3430-3441.
Truniger et al. (1999) "Role of the "YxGG/A" motif of ψ29 DNA polymerase in protein-primed replication," J. Mol. Biol., 286:57-69.
Vasquez-Ibar et al. (2002) "Engineering a terbium-binding site into an integral membrane protein for luminescence energy transfer." Proceedings on the National Academy of Sciences, USA, 99(6):3487-3492.
Widengren et al. (2007) "Strategies to improve photostabilities in ultrasensitive fluorescence spectroscopy." Journal of Physical Chemistry, 111(3):429-440.

\* cited by examiner

SEQ ID NO: 1
Amino acid sequence of WT Φ29 DNA polymerase

```
MKHMPRKMYSCDFETTTKVEDCRVWAYGYMNIEDHSEYKIGNSLDEFMAWVLKVQADLYFHNLKF
DGAFIINWLERNGFKWSADGLPNTYNTIISRMGQWYMIDICLGYKGKRKIHTVIYDSLKKLPFPV
KKIAKDFKLTVLKGDIDYHKERPVGYKITPEEYAYIKNDIQIIAEALLIQFKQGLDRMTAGSDSL
KGFKDIITTKKPKKVFPTLSLGLDKEVRYAYRGGFTWLNDRFKEKEIGEGMVFDVNSLYPAQMYS
RLLPYGEPIVFEGKYVWDEDYPLHIQHIRCEFELKEGYIPTIQIKRSRFYKGNEYLKSSGGEIAD
LWLSNVDLELMKEHYDLYNVEYISGLKFKATTGLPKDFIDKWTYIKTTSEGAIKQLAKLMLNSLY
GKFASNPDVTGKVPYLKENGALGFRLGEEETKDPVYTPMGVFITAWARYTTITAAQACYDRIIYC
DTDSIHLTGTEIPDVIKDIVDPKKLGYWAHESTFKRAKYLRQKTYIQDIYMKEVDGKLVEGSPDD
YTDIKFSVKCAGMTDKIKKEVTFENFKVGFSRKMKPKPVQVPGGVVLVDDTFTIK
```

SEQ ID NO: 2
Amino acid sequence of Φ29-derived DNA polymerase mutant 290P. 290P comprises an N62D substitution mutation.

```
MKHMPRKMYSCDFETTTKVEDCRVWAYGYMNIEDHSEYKIGNSLDEFMAWVLKVQADLYFHDLKF
DGAFIINWLERNGFKWSADGLPNTYNTIISRMGQWYMIDICLGYKGKRKIHTVIYDSLKKLPFPV
KKIAKDFKLTVLKGDIDYHKERPVGYKITPEEYAYIKNDIQIIAEALLIQFKQGLDRMTAGSDSL
KGFKDIITTKKPKKVFPTLSLGLDKEVRYAYRGGFTWLNDRFKEKEIGEGMVFDVNSLYPAQMYS
RLLPYGEPIVFEGKYVWDEDYPLHIQHIRCEFELKEGYIPTIQIKRSRFYKGNEYLKSSGGEIAD
LWLSNVDLELMKEHYDLYNVEYISGLKFKATTGLPKDFIDKWTYIKTTSEGAIKQLAKLMLNSLY
GKFASNPDVTGKVPYLKENGALGFRLGEEETKDPVYTPMGVFITAWARYTTITAAQACYDRIIYC
DTDSIHLTGTEIPDVIKDIVDPKKLGYWAHESTFKRAKYLRQKTYIQDIYMKEVDGKLVEGSPDD
YTDIKFSVKCAGMTDKIKKEVTFENFKVGFSRKMKPKPVQVPGGVVLVDDTFTIK
```

SEQ ID NO: 3
Amino acid sequence of PZA-derived polymerase mutant comprising an N62D substitution mutation, wherein the numbering of amino acid positions is relative to WT Φ29 DNA polymerase (SEQ ID NO: 1)

```
MPRKMYSCDFETTTKVEDCRVWAYGYMNIEDHSEYKIGNSLDEFMAWVLKVQADLYFHDLKFDGA
FIINWLERNGFKWSADGLPNTYNTIISRMGQWYMIDICLGYKGKRKIHTVIYDSLKKLPFPVKKI
AKDFKLTVLKGDIDYHKERPVGYEITPDEYAYIKNDIQIIAEALLIQFKQGLDRMTAGSDDLKGF
KDIITTKKPKKVFPTLSLGLDKEVRYAYRGGFTWLNDRFKEKEIGEGMVFDVNSLYPAQMYSRLL
PYGEPIVFEGKYVWDEDYPLHIQHIRCEFELKEGYIPTIQIKRSRFYKGNEYLKSSGGEIADLWV
SNVDLELMKEHYDLYNVEYISGLKFKATTGLPKDFIDKWTHIKTTSEGAIKQLAKLMLNSLYGKF
ASNPDVTGKVPYLKENGALGFRLGEEETKDPVYTPMGVFITAWARYTTITAAQACFDRIIYCDTD
SIHLTGTEIPDVIKDIVDPKKLGYWAHESTFKRAKYLRQKTYIQDIYMKEVDGKLVEGSPDDYTT
IKFSVKCAGMTDKIKKEVTFENFKVGFSRKMKPKPVQVPGGVVLVDDTFTIK
```

Fig. 6

SEQ ID NO: 4
Amino acid sequence of B103-derived polymerase mutant comprising an N62D
substitution mutation, wherein the numbering of amino acid positions is relative to WT
Φ29 DNA polymerase (SEQ ID NO: 1)

MPRKMPSCDFETTTKLDDCRVWAYGYMEIGNLDNYKIGNSLDEFMQWVMEIQADLYFHDLKFDGA
FIVNWLEHHGFKWSNEGLPNTYNTIISKMGQWYMIDICFGYKGKRKLHTVIYDSLKKLPFPVKKI
AKDFQLPLLKGDIDYHAERPVGHEITPEEYEYIKNDIEIIARALDIQFKQGLDRMTAGSDSLKGF
KDILSTKKFNKVFPKLSLPMDKEIRRAYRGGFTWLNDKYKEKEIGEGMVFDVNSLYPSQMYSRFL
PYGAPIVFQGKYEKDEQYPLYIQRIRFEFELKEGYIPTIQIKKNPFFKGNEYLKNSGAEPVELYL
TNVDLELIQEHYEMYNVEYIDGFKFREKTGLPKEFIDKWTYVKTHEKGAKKQLAKLMFDSLYGKF
ASNPDVTGKVPYLKEDGSLGFRVGDEEYKDPVYTPMGVPITAWARFTTITAAQACYDRIIYCDTD
SIHLTGTEVPEIIKDIVDPKKLGYWAHESTFKRAKYLRQKTYIQDIYAKEVDGKLIECSPDEATT
TKFSVKCAGMTDTIKKKVTFDNFRVGFSSTGKPKPVQVNGGVVLVDSVFTIKKPKPVQVNGGVVL
VDSVFTIK

SEQ ID NO: 5
Amino acid sequence of M2-derived polymerase mutant comprising an N62D
substitution mutation, wherein the numbering of amino acid positions is relative to WT
Φ29 DNA polymerase (SEQ ID NO: 1)

MSRKMFSCDFETTTKLDDCRVWAYGYMEIGNLDNYKIGNSLDEFMQWVMEIQADLYFHDLKFDGA
FIVNWLEQHGFKWSNEGLPNTYNTIISKMGQWYMIDICFGYKGKRKLHTVIYDSLKKLPFPVKKI
AKDFQLPLLKGDIDYHTERFVGHEITPEEYEYIKNDIEIIARALDIQFKQGLDRMTAGEDSLKGF
KDILSTKKFNKVFPKLSLPMDKEIRKAYRGGFTWLNDKYKEKEIGEGMVFDVNSLYPSQMYSRFL
PYGAPIVFQGKYEKDEQYPLYIQRIRFEFELKEGYIPTIQIKKNPFFKGNEYLKNSGVEPVELYL
TNVDLELIQEHYELYNVEYIDGFKFREKTGLPKDFIDKWTYVKTHEEGAKKQLAKLMLNSLYGKF
ASNPDVTGKVPYLKDDGLGFRVGDEEYKDPVYTPMGVPITAWARFTTITAAQACYDRIIYCDTDS
IHLTGTEVPEIIKDIVDPKKLGYWAHESTFKRAKYLRQKTYIQDIYVKEVDGKLKECSPDEATTT
KFSVKCAGMTDTIKKKVTFDNFAVGFSSMGKPKPVQVNGGVVLVDSVFTIK

SEQ ID NO: 6
Amino acid sequence of GA1-derived polymerase mutant comprising an N62D
substitution mutation, wherein the numbering of amino acid positions is relative to WT
Φ29 DNA polymerase (SEQ ID NO: 1)

MARSVYVCDFETTTDPEDCRLWAWGWMDIYNTDKWSYGEDIDSFMEWALNSNSDIYFHDLKFDGS
FILPWWLRNGYVHTEEDRTNTPKEFTTTISGMGQWYAVDVCINTRGKNKNHVFYDSLKKLPFKV
EQIAKGFGLPVLKGDIDYKKYRPVGYVMDDNEISYLKHDLLIVALALRSMFDNDFTSMTVGSDAL
NTYKEMLGVKQWEKYFPVLSLKVNSEIRKAYKGGFTWVNPKYQGETVYGGMVFDVNSMYPAMMKN
KLLPYGEPVMFKGEYEKNVEYPLYIQQVRCFFELKKDKIPCIQIKGNARFGQNEYLSTSGDEYVD
LYVTNVDWELIKKHYDIFEEEFIGGFMFKGFIGFFDEYIDRFMEIKNSPDSSAEQSLQAKLMLNS
LYGKFATNPDITGKVPYLDENGVLKFRKGELKERDFVYTPMGCFITAYARENILSNAQKLYPRFI
YADTDSIHVEGLGEVDAIKDVIDPKKLGYWDHEATFQRARYVRQKTYFIETTWKENDKGKLVVCB
PQDATKVKPKIACAGMSDAIKERIRFNEPKIGYSTHGSLKPKNVLGGVVLMDYPFAIK

Fig. 6 cont'd

SEQ ID NO: 7
Amino acid sequence of Φ29-derived DNA polymerase mutant 587P. 587P comprises
N62D and W483S substitution mutations.

```
MKHMPRKMYSCDFETTTKVEDCRVWAYGYMNIEDHSEYKIGNSLDEFMAWVLKVQADLYFHDLKF
DGAFIINWLERNGFKWSADGLPNTYNTIISRMGQWYMIDICLGYKGKRKIHTVIYDSLKKLPFPV
KKIAKDFKLTVLKGDIDYHKERPVGYKITPEEYAYIKNDIQIIAEALLIQFKQGLDRMTAGSDSL
KGFKDIITTKKFKKVFPTLSLGLDKEVRYAYRGGFTWLNDRFKEKEIGEGMVFDVNSLYPAQMYS
RLLPYGEPIVFEGKYVWDEDYPLHIQHIRCEFELKEGYIPTIQIKRSRFYKGNEYLKSSGGEIAD
LWLSNVDLELMKEHYDLYNVEYISGLKFKATTGLFKDFIDKWTYIKTTSEGAIKQLAKLMLNSLY
GKFASNPDVTGKVPYLKENGALGFRLGEEETKDPVYTPMGVFITAWARYTTITAAQACYDRIIYC
DTDSIHLTGTEIPDVIKDIVDPKKLGYSAHESTFKRAKYLRQKTYIQDIYMKEVDGKLVEGSPDD
YTDIKFSVKCAGMTDKIKKEVTFENFKVGFSRKMKPKPVQVPGGVVLVDDTFTIK
```

SEQ ID NO: 8
Amino acid sequence of Φ29-derived DNA polymerase mutant 596P. 596P comprises
N62D and F526L substitution mutations.

```
MKHMPRKMYSCDFETTTKVEDCRVWAYGYMNIEDHSEYKIGNSLDEFMAWVLKVQADLYFHDLKF
DGAFIINWLERNGFKWSADGLPNTYNTIISRMGQWYMIDICLGYKGKRKIHTVIYDSLKKLPFPV
KKIAKDFKLTVLKGDIDYHKERPVGYKITPEEYAYIKNDIQIIAEALLIQFKQGLDRMTAGSDSL
KGFKDIITTKKFKKVFPTLSLGLDKEVRYAYRGGFTWLNDRFKEKEIGEGMVFDVNSLYPAQMYS
RLLPYGEPIVFEGKYVWDEDYPLHIQHIRCEFELKEGYIPTIQIKRSRFYKGNEYLKSSGGEIAD
LWLSNVDLELMKEHYDLYNVEYISGLKFKATTGLFKDFIDKWTYIKTTSEGAIKQLAKLMLNSLY
GKFASNPDVTGKVPYLKENGALGFRLGEEETKDPVYTPMGVFITAWARYTTITAAQACYDRIIYC
DTDSIHLTGTEIPDVIKDIVDPKKLGYWAHESTFKRAKYLRQKTYIQDIYMKEVDGKLVEGSPDD
YTDIKLSVKCAGMTDKIKKEVTFENFKVGFSRKMKPKPVQVPGGVVLVDDTFTIK
```

SEQ ID NO: 9
Amino acid sequence of chimeric DNA polymerase mutant 604P. 604P is derived from
the polymerases encoded by SEQ ID NOs: 2-6.

```
MKHMPRKMYSCDFETTTKVEDCRVWAYGYMNIEDHSEYKIGNSLDEFMAWVLKVQADLYFHDLKF
DGAFIINWLERNGFKWSADGLPNTYNTIISRMGQWYMIDICLGYKGKRKIHTVIYDSLKKLPFPV
KKIAKDFQLPLLKGDIDYHAERPVGHETTPEEYEYIKNDIEIIARALDIQFKQGLDRMTAGSDSL
KGFKDILSTKKFNKVPPKLSLPMDKEIRRAYRGGFTWLNDKYKEKEIGEGMVFDVNSMYPAMMKN
KLLPYGEPVMFKGEYKENVEYPLYIQQVRCFFELKKDKIPCIQIKGNARFGQNEYLSTSGDEYVD
LYVTNVDWELIKKHYDIFEEEFIGGFMFKGFIGFFDEYIDRFMEIKNSPDSSAEQSLQAKLMLNS
LYGKFATNPDVTGKVPYLKENGALGFRLGEEETKDPVYTPMGVFITAWARFTTITAAQACYDRII
YCDTDSIHLTGTEVPEIIKDIVDPKKLGYWAHESTFKRAKYLRQKTYIQDIYVKEVDGKLKECSP
DEATTTKFSVKCAGMTDTIKKKVTFDNFRVGFSSTGKPKPVQVNGGVVLVDSVFTIK
```

Fig. 6 cont'd

SEQ ID NO: 10
Amino acid sequence of chimeric DNA polymerase mutant 605P. 605P is derived from from the polymerases encoded by SEQ ID NOs: 2-6.

MAKSVYVCDFETTTDPEDCRLWAWGWMDIYNTDKWSYGEDIDSFMEWALNSNSDIYFHDLKFDGA
FIINWLERNGFKWSADGLPNTYNTIISRMGQWYMIDICLGYKGKRKIHTVIYDSLKKLPFKVEQI
AKGFGLPVLKGDIDYKKYRPVGYVMDDNEIEYLKHDLLIVALALRSMFDNDFTSMTVGSDALNTY
KEMLGVKQWEKYFPVLSLKVNSEIRKAYKGGFTWVNPKYQGETVYGGMVFDVNSLYPAQMYSRLL
PYGEPIVFEGKYVWDEDYPLHIQHIRCEFELKEGYIPTIQIKRSRFYKGNEYLKSSGGEIADLWL
SNVDLELMKEHYDLYNVEYISGLKFKATTGLFKDFIDKWTYIKTTSEGAIKQLAKLMLNSLYGKF
ASNPDVTGKVPYLKEDGSLGFRVGDEEYKDPVYTPMGVFITAWARFTTITAAQACYDRIIYCDTD
SIHLTGTEVPEIIKDIVDPKKLGYWAHESTFKRAKYLRQKTYIQDIYAKEVDGKLIECSPDEATT
TKFSVKCAGMTDTIKKKVTFDNFRVGFSSTGKPKPVQVNGGVVLVDSVFTIK

SEQ ID NO: 11
Amino acid sequence of chimeric DNA polymerase mutant 1093P. 1093P is derived from the polymerases encoded by SEQ ID NOs: 2-6.

MKHMPRKMYSCDFETTTKVEDCRVWAYGYMNIEDHSEYKIGNSLDEFMAWVLKVQADLYFHDLKF
DGAFIINWLERNGFKWSADGLPNTYNTIISRMGQWYMIDICLGYKGKRKIHTVIYDSLKKLPFPV
KKIAKDFQLPLLKGDIDYHAERPVGHEITPEEYEYIKNDIEIIARALDIQFKQGLDRMTAGSDSL
KGFKDILSTKKFNKVFPKLSLPMDKEIRRAYRGGFTWLNDKYKEKEIGEGMVFDVNSMYPAMMKN
KLLPYGEPVMFKGEYKKNVEYPLYIQQVRCFFELKKDKIPCIQIKGNARFGQNEYLSTSGDEYVD
LYVTNVDWELIKKHYDIFEEEFIGGFMFKGFIGFFDEYIDRFFEIKNSPYSSAKQSLQAKLMLNS
LYGKFATNPDVTGKVPYLKENGALGFRLGEEETKDPVYTPMGVFITAWARFTTITAAQACYDRII
YCDTDSIHLTGTEVPEIIKDIVDPKKLGYWAHESTFKRAKYLRQKTYIQDIYVKEVDGYLKECSP
DEATTTKFSVKCAGMTDTIKKKVTFDNFRVGFSSTGKPKPVQVNGGVVLVDSVFTIK

SEQ ID NO: 12
Amino acid sequence of chimeric DNA polymerase mutant 1094P. 1094P is derived from the polymerases encoded by SEQ ID NOs: 2-6.

MKHMPRKMYSCDFETTTKVEDCRVWAYGYMNIEDHSEYKIGNSLDEFMAWVLKVQADLYFHDLKF
DGAFIINWLERNGFKWSADGLPNTYNTIISRMGQWYMIDICLGYKGKRKIHTVIYDSLKKLPFPV
KKIAKDFQLPLLKGDIDYHAERPVGHEITPEEYEYIKNDIEIIARALDIQFKQGLDRMTAGSDSL
KGFKDILSTKKFNKVFPKLSLPMDKEIRRAYRGGFTWLNDKYKEKEIGEGMVFDVNSMYPAMMKN
KLLPYGEPVMFKGEYKKNVEYPLYIQQVRCFFELKKDKIPCIQIKGNARFGQNEYLSTSGDEYVD
LYVTNVDWELIKKHYDIFEEEFIGGFMFKGFIGFFDEYIDRFFEIKNSPYSSAKQLAKLMLNSLY
GKFATNPDVTGKVPYLKENGALGFRLGEEETKDPVYTPMGVFITAWARFTTITAAQACYDRIIYC
DTDSIHLTGTEVPEIIKDIVDPKKLGYWAHESTFKRAKYLRQKTYIQDIYVKEVDGYLKECSPDE
ATTTKFSVKCAGMTDTIKKKVTFDNFRVGFSSTGKPKPVQVNGGVVLVDSVFTIK

Fig. 6 cont'd

SEQ ID NO: 13
Nucleotide sequence of the Φ29-derived DNA polymerase mutant 290P ATGAAACACATGCCACGTAAAATGTATTCCTGCGACTTTGAGACTACCACCAAGGTTGAAGATTG
CCGCGTATGGGCATACGGTTACATGAACATCGAAGACCACTCCGAGTATAAGATTGGTAACTCCC
TGGATGAATTTATGGCTTGGGTTCTGAAAGTTCAGGCTGACCTGTACTTCCACGATCTGAAATTT
GATGGCGCATTCATCATCAACTGGCTGGAACGTAACGGTTTTAAATGGTCCGCAGATGGTCTGCC
AAATACCTACAACACCATCATTTCTCGCATGGGCCAGTGGTATATGATTGATATTTGCCTGGGTT
ACAAGGGTAAACGCAAGATCCACACCGTGATCTACGACTCTCTGAAGAAACTGCCGTTTCCGGTT
AAGAAAATTGCGAAAGACTTTAAGCTGACGGTACTGAAAGGCGACATCGACTATCATAAGGAGCG
CCCGGTCGGTTACAAAATCACCCCGGAAGAATATGCCTACATTAAAAACGATATTCAGATTATCG
CAGAAGCTCTGCTGATCCAGTTCAAGCAGGGTCTGGATCGTATGACGGCAGGTTCTGACTCTCTG
AAAGGCTTCAAAGACATTATCACCACCAAGAAGTTTAAAAAGGTTTTCCCGACCCTGAGCCTGGG
TCTGGACAAGGAAGTTCGTTATGCCTACCGTGGTGGTTTCACCTGGCTGAATGACCGTTTTAAAG
AAAAAGAGATCGGCGAAGGTATGGTTTTTGATGTTAATTCCCTGTACCCAGCGCAAATGTACTCT
CGCCTGCTGCCGTACGGCGAGCCGATCGTATTCGAGGGTAAATACGTCTGGGACGAGGACTACCC
TCTGCACATTCAGCACATTCGTTGTGAATTTGAACTGAAGGAAGGCTACATCCCGACCATCCAGA
TCAAGCGTTCCCGTTTCTACAAGGGTAACGAATACCTGAAATCTTCCGGCGGTGAAATTGCTGAC
CTGTGGCTGTCTAATGTTGATCTGGAACTGATGAAAGAGCACTACGACCTGTACAATGTTGAATA
TATCTCTGGTCTGAAGTTCAAAGCAACCACTGGCCTGTTCAAGGACTTTATCGACAAATGGACGT
ATATCAAAACTACCTCTGAAGGCGCCATCAAACAGCTGGCGAAGCTGATGCTGAACAGCCTGTAC
GGTAAATTCGCGTCCAACCCGGACGTTACCGGTAAAGTGCCATACCTGAAAGAGAACGGTGCTCT
GGGTTTTCGTCTGGGTGAGGAGGAAACGAAAGACCCTGTATATACCCCGATGGGTGTCTTTATCA
CGGCCTGGGCACGCTATACGACCATCACGGCAGCGCAGGCTTGTTATGATCGTATTATCTACTGC
GATACCGATTCTATTCACCTGACTGGTACTGAAATTCCGGACGTTATCAAAGACATCGTAGACCC
GAAGAAACTGGGCTACTGGGCGCACGAATCCACTTTTAAGCGTGCAAAATATCTGCGTCAGAAAA
CCTACATCCAGGATATTTACATGAAAGAAGTAGACGGCAAACTGGTAGAGGGCTCTCCTGACGAC
TACACTGACATCAAGTTCTCTGTGAAATGCGCAGGCATGACGGACAAAATCAAAAAGGAAGTGAC
TTTCGAAAACTTCAAAGTGGGTTTTTCTCGTAAAATGAAACCGAAGCCTGTTCAGGTACCGGGTG
GCGTAGTGCTGGTTGATGACACTTTTACTATCAAATAA

SEQ ID NO: 14
Nucleotide sequence of of Φ29-derived DNA polymerase mutant 587P ATGAAACACATGCCACGTAAAATGTATTCCTGCGACTTTGAGACTACCACCAAGGTTGAAGATTG
CCGCGTATGGGCATACGGTTACATGAACATCGAAGACCACTCCGAGTATAAGATTGGTAACTCCC
TGGATGAATTTATGGCTTGGGTTCTGAAAGTTCAGGCTGACCTGTACTTCCACGATCTGAAATTT
GATGGCGCATTCATCATCAACTGGCTGGAACGTAACGGTTTTAAATGGTCCGCAGATGGTCTGCC
AAATACCTACAACACCATCATTTCTCGCATGGGCCAGTGGTATATGATTGATATTTGCCTGGGTT
ACAAGGGTAAACGCAAGATCCACACCGTGATCTACGACTCTCTGAAGAAACTGCCGTTTCCGGTT
AAGAAAATTGCGAAAGACTTTAAGCTGACGGTACTGAAAGGCGACATCGACTATCATAAGGAGCG
CCCGGTCGGTTACAAAATCACCCCGGAAGAATATGCCTACATTAAAAACGATATTCAGATTATCG
CAGAAGCTCTGCTGATCCAGTTCAAGCAGGGTCTGGATCGTATGACGGCAGGTTCTGACTCTCTG
AAAGGCTTCAAAGACATTATCACCACCAAGAAGTTTAAAAAGGTTTTCCCGACCCTGAGCCTGGG
TCTGGACAAGGAAGTTCGTTATGCCTACCGTGGTGGTTTCACCTGGCTGAATGACCGTTTTAAAG
AAAAAGAGATCGGCGAAGGTATGGTTTTTGATGTTAATTCCCTGTACCCAGCGCAAATGTACTCT
CGCCTGCTGCCGTACGGCGAGCCGATCGTATTCGAGGGTAAATACGTCTGGGACGAGGACTACCC
TCTGCACATTCAGCACATTCGTTGTGAATTTGAACTGAAGGAAGGCTACATCCCGACCATCCAGA
TCAAGCGTTCCCGTTTCTACAAGGGTAACGAATACCTGAAATCTTCCGGCGGTGAAATTGCTGAC

Fig. 6 cont'd

```
CTGTGGCTGTCTAATGTTGATCTGGAACTGATGAAAGAGCACTACGACCTGTACAATGTTGAATA
TATCTCTGGTCTGAAGTTCAAAGCAACCACTGGCCTGTTCAAGGACTTTATCGACAAATGGACGT
ATATCAAAACTACCTCTGAAGGCGCCATCAAACAGCTGGCGAAGCTGATGCTGAACAGCCTGTAC
GGTAAATTCGCGTCCAACCCGGACGTTACCGGTAAAGTGCCATACCTGAAAGAGAACGGTGCTCT
GGGTTTTCGTCTGGGTGAGGAGGAAACGAAAGACCCTGTATATACCCCGATGGGTGTCTTTATCA
CGGCCTGGGCACGCTATACGACCATCACGGCAGCGCAGGCTTGTTATGATCGTATTATCTACTGC
GATACCGATTCTATTCACCTGACTGGTACTGAAATTCCGGACGTTATCAAAGACATCGTAGACCC
GAAGAAACTGGGCTACAGCGCGCACGAATCCACTTTTAAGCGTGCAAAATATCTGCGTCAGAAAA
CCTACATCCAGGATATTTACATGAAAGAAGTAGACGGCAAACTGGTAGAGGGCTCTCCTGACGAC
TACACTGACATCAAGTTCTCTGTGAAATGCGCAGGCATGACGGACAAAATCAAAAAGGAAGTGAC
TTTCGAAAACTTCAAAGTGGGTTTTTCTCGTAAAATGAAACCGAAGCCTGTTCAGGTACCGGGTG
GCGTAGTGCTGGTTGATGACACTTTTACTATCAAATAA
```

SEQ ID NO: 15
Nucleotide sequence of of Φ29-derived DNA polymerase mutant 596P

```
ATGAAACACATGCCACGTAAAATGTATTCCTGCGACTTTGAGACTACCACCAAGGTTGAAGATTG
CCGCGTATGGGCATACGGTTACATGAACATCGAAGACTACTCCGAGTATAAGATTGGTAACTCCC
TGGATGAATTTATGGCTTGGGTTCTGAAAGTTCAGGCTGACCTGTACTTCCACGATCTGAAATTT
GATGGCGCATTCATCATCAACTGGCTGGAACGTAACGGTTTTAAATGGTCCGCAGATGGTCTGCC
AAATACCTACAACACCATCATTTCTCGCATGGGCCAGTGGTATATGATTGATATTTGCCTGGGTT
ACAAGGGTAAACGCAAGATCCACACCGTGATCTACGACTCTCTGAAGAAACTGCCGTTTCCGGTT
AAGAAAATTGCGAAAGACTTTAAGCTGACGGTACTGAAAGGCGACATCGACTATCATAAGGAGCG
CCCGGTCGGTTACAAAATCACCCCGGAAGAATATGCCTACATTAAAAACGATATTCAGATTATCG
CAGAAGCTCTGCTGATCCAGTTCAAGCAGGGTCTGGATCGTATGACGGCAGGTTCTGACTCTCTG
AAAGGCTTCAAAGACATTATCACCACCAAGAAGTTTAAAAAGGTTTTCCCGACCCTGAGCCTGGG
TCTGGACAAGGAAGTTCGTTATGCCTACCGTGGTGGTTTCACCTGGCTGAATGACCGTTTTAAAG
AAAAAGAGATCGGCGAAGGTATGGTTTTTGATGTTAATTCCCTGTACCCAGCGCAAATGTACTCT
CGCCTGCTGCCGTACGGCGAGCCGATCGTATTCGAGGGTAAATACGTCTGGGACGAGGACTACCC
TCTGCACATTCAGCACATTCGTTGTGAATTTGAACTGAAGGAAGGCTACATCCCGACCATCCAGA
TCAAGCGTTCCCGTTTCTACAAGGGTAACGAATACCTGAAATCTTCCGGCGGTGAAATTGCTGAC
CTGTGGCTGTCTAATGTTGATCTGGAACTGATGAAAGAGCACTACGACCTGTACAATGTTGAATA
TATCTCTGGTCTGAAGTTCAAAGCAACCACTGGCCTGTTCAAGGACTTTATCGACAAATGGACGT
ATATCAAAACTACCTCTGAAGGCGCCATCAAACAGCTGGCGAAGCTGATGCTGAACAGCCTGTAC
GGTAAATTCGCGTCCAACCCGGACGTTACCGGTAAAGTGCCATACCTGAAAGAGAACGGTGCTCT
GGGTTTTCGTCTGGGTGAGGAGGAAACGAAAGACCCTGTATATACCCCGATGGGTGTCTTTATCA
CGGCCTGGGCACGCTATACGACCATCACGGCAGCGCAGGCTTGTTATGATCGTATTATCTACTGC
GATACCGATTCTATTCACCTGACTGGTACTGAAATTCCGGACGTTATCAAAGACATCGTAGACCC
GAAGAAACTGGGCTACTGGGCGCACGAATCCACTTTTAAGCGTGCAAAATATCTGCGTCAGAAAA
CCTACATCCAGGATATTTACATGAAAGAAGTAGACGGCAAACTGGTAGAGGGCTCTCCTGACGAC
TACACTGACATCAAGCTGTCTGTGAAATGCGCAGGCATGACGGACAAAATCAAAAAGGAAGTGAC
TTTCGAAAACTTCAAAGTGGGTTTTTCTCGTAAAATGAAACCGAAGCCTGTTCAGGTACCGGGTG
GCGTAGTGCTGGTTGATGACACTTTTACTATCAAATAA
```

SEQ ID NO: 16
Nucleotide sequence of of Φ29-derived DNA polymerase mutant 604P ATGAAACACATGCCACGTAAAATGTATTCCTGCGACTTTGAGACTACCACCAAGGTTGAAGATTG
CCGCGTATGGGCATACGGTTACATGAACATCGAAGACCACTCCGAGTATAAGATTGGTAACTCCC
TGGATGAATTTATGGCTTGGGTTCTGAAAGTTCAGGCTGACCTGTACTTCCACGATCTGAAATTT
GATGGCGCATTCATCATCAACTGGCTGGAACGTAACGGTTTTAAATGGTCCGCAGATGGTCTGCC
AAATACCTACAACACCATCATTTCTCGCATGGGCCAGTGGTATATGATTGATATTTGCCTGGGTT
ACAAGGGTAAACGCAAGATCCACACCGTGATCTACGACTCTCTGAAGAAACTGCCGTTTCCGGTT
AAGAAAATTGCGAAAGACTTTCAGCTGCCACTGCTGAAAGGCGACATCGACTATCATGCTGAGCG
CCCGGTCGGTCATGAGATCACCCCGGAAGAATATGAATACATTAAAAACGATATTGAAATTATCG
CACGCGCTCTGGACATCCAGTTCAAGCAGGGTCTGGATCGTATGACGGCAGGTTCTGACTCTCTG
AAAGGCTTCAAAGACATTCTGTCTACCAAGAAGTTTAACAAAGTTTTCCCGAAACTGAGCCTGCC
GATGGACAAGGAAATCCGTCGTGCCTACCGTGGTGGTTTCACCTGGCTGAATGACAAATACAAAG
AAAAAGAGATCGGCGAAGGTATGGTTTTTGATGTTAATTCCATGTACCCAGCGATGATGAAAAAC
AAACTGCTGCCGTACGGCGAGCCGGTAATGTTCAAAGGCGAGTACAAGAAAAACGTCGAGTACCC
TCTGTACATTCAGCAGGTGCGTTGTTTCTTTGAACTGAAGAAAGACAAGATCCCGTGCATCCAGA
TCAAGGGCAACGCACGTTTCGGTCAAAACGAATACCTGTCTACCTCCGGCGACGAATACGTGGAC
CTGTACGTGACTAATGTTGATTGGGAACTGATCAAGAAACACTACGACATTTTCGAAGAAGAGTT
CATCGGCGGTTTTATGTTCAAGGGCTTCATTGGCTTCTTCGACGAATACATCGACCGTTTCATGG
AAATCAAAAACTCTCCAGACTCCTCTGCTGAACAGAGCCTGCAAGCGAAGCTGATGCTGAACAGC
CTGTACGGTAAATTCGCGACCAACCCGGACGTTACCGGTAAAGTGCCATACCTGAAAGAGAACGG
TGCTCTGGGTTTTCGTCTGGGTGAGGAGGAAACGAAAGACCCTGTATATACCCCGATGGGTGTCT
TTATCACGGCCTGGGCACGCTTCACGACCATCACGGCAGCGCAGGCTTGTTATGATCGTATTATC
TACTGCGATACCGATTCTATTCACCTGACTGGTACTGAGGTTCCGGAAATTATCAAAGACATCGT
AGACCCGAAGAAACTGGGCTACTGGGCGCACGAATCCACTTTTAAGCGTGCAAAATATCTGCGTC
AGAAAACCTACATCCAGGATATTTACGTTAAAGAAGTAGACGGCAAACTGAAAGAGTGTTCTCCT
GACGAAGCTACCACTACTAAGTTCTCTGTGAAATGCGCAGGCATGACGGACACCATCAAAAAGAA
GGTGACTTTCGACAACTTCCGTGTGGGTTTTTCCTCTACTGGCAAACCGAAGCCTGTTCAGGTAA
ACGGTGGCGTAGTGCTGGTTGATTCTGTTTTACTATCAAATAA

SEQ ID NO: 17
Nucleotide sequence of of Φ29-derived DNA polymerase mutant 605P ATGGCACGTTCTGTTTATGTATGCGACTTTGAGACTACCACCGATCCGGAAGATTGCCGCCTGTG
GGCATGGGGTTGGATGGATATCTACAACACTGACAAATGGTCCTACGGTGAGGACATTGACTCCT
TTATGGAGTGGGCTCTGAATAGCAATTCCGACATTTACTTCCACGATCTGAAATTTGATGGCGCA
TTCATCATCAACTGGCTGGAACGTAACGGTTTTAAATGGTCCGCAGATGGTCTGCCAAATACCTA
CAACACCATCATTTCTCGCATGGGCCAGTGGTATATGATTGATATTTGCCTGGGTTACAAGGGTA
AACGCAAGATCCACACCGTGATCTACGACTCTCTGAAGAAACTGCCGTTTAAAGTTGAGCAGATT
GCGAAAGGTTTTGGCCTGCCAGTACTGAAAGGCGACATCGACTATAAAAGTACCGCCCGGTCGG
TTACGTTATGGATGATAACGAAATCGAATATCTGAAACACGATCTGCTGATTGTTGCACTGGCTC
TGCGTAGCATGTTCGACAACGATTTCACTTCTATGACGGTTGGTTCTGACGCTCTGAACACCTAC
AAAGAAATGCTGGGCGTTAAACAGTGGGAAAAGTACTTTCCGGTTCTGAGCCTGAAGGTTAACTC
CGAAATCCGTAAAGCCTACAAAGGTGGTTTCACCTGGGTAAATCCGAAATATCAGGGTGAAACTG
TATATGGCGGTATGGTTTTTGATGTTAATTCCCTGTACCCAGCGCAAATGTACTCTCGCCTGCTG
CCGTACGGCGAGCCGATCGTATTCGAGGGTAAATACGTCTGGGACGAGGACTACCCTCTGCACAT
TCAGCACATTCGTTGTGAATTTGAACTGAAGGAAGGCTACATCCCGACCATCCAGATCAAGCGTT

Fig. 6 cont'd

CCCGTTTCTACAAGGGTAACGAATACCTGAAATCTTCCGGCGGTGAAATTGCTGACCTGTGGCTG
TCTAATGTTGATCTGGAACTGATGAAAGAGCACTACGACCTGTACAATGTTGAATATATCTCTGG
TCTGAAGTTCAAAGCAACCACTGGCCTGTTCAAGGACTTTATCGACAAATGGACGTATATCAAAA
CTACCTCTGAAGGCGCCATCAAACAGCTGGCGAAGCTGATGCTGAACAGCCTGTACGGTAAATTC
GCGTCCAACCCGGACGTTACCGGTAAAGTGCCATACCTGAAAGAGGATGGTTCCCTGGGTTTTCG
TGTTGGTGATGAGGAGTACAAAGACCCTGTATATACCCCGATGGGTGTCTTTATCACGGCCTGGG
CACGGCTTCACGACCATCACGGCAGCGCAGGCTTGTTATGATCGTATTATCTACTGCGATACCGAT
TCTATTCACCTGACTGGTACTGAAGTGCCGGAAATTATCAAAGACATCGTAGACCCGAAGAAACT
GGGCTACTGGGCGCACGAATCCACTTTTAAGCGTGCAAAATATCTGCGTCAGAAAACCTACATCC
AGGATATTTACGCCAAAGAAGTAGACGGCAAACTGATTGAGTGTTCTCCTGACGAAGCGACGACC
ACTAAGTTCTCTGTGAAATGCGCAGGCATGACGGACACCATCAAAAAGAAGGTGACTTTCGACAA
CTTCCGTGTGGGTTTTTCCTCTACTGGCAAACCGAAGCCTGTTCAGGTAAACGGTGGCGTAGTGC
TGGTTGATTCTGTTTTACTATCAAATAA

SEQ ID NO: 18
Nucleotide sequence of of Φ29-derived DNA polymerase mutant 1093P ATGAAACACATGCCACGTAAAATGTATTCCTGCGACTTTGAGACTACCACCAAGGTTGAAGATTG
CCGCGTATGGGCATACGGTTACATGAACATCGAAGACCACTCCGAGTATAAGATTGGTAACTCCC
TGGATGAATTTATGGCTTGGGTTCTGAAAGTTCAGGCTGACCTGTACTTCCACGATCTGAAATTT
GATGGCGCATTCATCATCAACTGGCTGGAACGTAACGGTTTTAAATGGTCCGCAGATGGTCTGCC
AAATACCTACAACACCATCATTTCTCGCATGGGCCAGTGGTATATGATTGATATTTGCCTGGGTT
ACAAGGGTAAACGCAAGATCCACACCGTGATCTACGACTCTCTGAAGAAACTGCCGTTTCCGGTT
AAGAAAATTGCGAAAGACTTTCAGCTGCCACTGCTGAAAGGCGACATCGACTATCATGCTGAGCG
CCCGGTCGGTCATGAGATCACCCCGGAAGAATATGAATACATTAAAAACGATATTGAAATTATCG
CACGCGCTCTGGACATCCAGTTCAAGCAGGGTCTGGATCGTATGACGGCAGGTTCTGACTCTCTG
AAAGGCTTCAAAGACATTCTGTCTACCAAGAAGTTTAACAAAGTTTTCCCGAAACTGAGCCTGCC
GATGGACAAGGAAATCCGTCGTGCCTACCGTGGTGGTTTCACCTGGCTGAATGACAAATACAAAG
AAAAAGAGATCGGCGAAGGTATGGTTTTTGATGTTAATTCCATGTACCCAGCGATGATGAAAAAC
AAACTGCTGCCGTACGGCGAGCCGGTAATGTTCAAAGGCGAGTACAAGAAAAACGTCGAGTACCC
TCTGTACATTCAGCAGGTGCGTTGTTTCTTTGAACTGAAGAAAGACAAGATCCCGTGCATCCAGA
TCAAGGGCAACGCACGTTTCGGTCAAAACGAATACCTGTCTACCTCCGGCGACGAATACGTGGAC
CTGTACGTGACTAATGTTGATTGGGAACTGATCAAGAAACACTACGACATTTTCGAAGAAGAGTT
CATCGGCGGTTTTATGTTCAAGGGCTTCATTGGCTTCTTCGACGAATACATCGACCGTTTCTTCG
AAATCAAAAACTCTCCATATTCCTCTGCTAAGCAGAGCCTGCAAGCGAAGCTGATGCTGAACAGC
CTGTACGGTAAATTCGCGACCAACCCGGACGTTACCGGTAAAGTGCCATACCTGAAAGAGAACGG
TGCTCTGGGTTTTCGTCTGGGTGAGGAGGAAACGAAAGACCCTGTATATACCCCGATGGGTGTCT
TTATCACGGCCTGGGCACGCTTCACGACCATCACGGCAGCGCAGGCTTGTTATGATCGTATTATC
TACTGCGATACCGATTCTATTCACCTGACTGGTACTGAGGTTCCGGAAATTATCAAAGACATCGT
AGACCCGAAGAAACTGGGCTACTGGGCGCACGAATCCACTTTTAAGCGTGCAAAATATCTGCGTC
AGAAAACCTACATCCAGGATATTTACGTTAAAGAAGTAGACGGCTACCTGAAAGAGTGTTCTCCT
GACGAAGCTACCACTACTAAGTTCTCTGTGAAATGCGCAGGCATGACGGACACCATCAAAAAGAA
GGTGACTTTCGACAACTTCCGTGTGGGTTTTTCCTCTACTGGCAAACCGAAGCCTGTTCAGGTAA
ACGGTGGCGTAGTGCTGGTTGATTCTGTTTTACTATCAAATAA

SEQ ID NO: 19
Nucleotide sequence of of Φ29-derived DNA polymerase mutant I094P

```
ATGAAACACATGCCACGTAAAATGTATTCCTGCGACTTTGAGACTACCACCAAGGTTGAAGATTG
CCGCGTATGGGCATACGGTTACATGAACATCGAAGACCACTCCGAGTATAAGATTGGTAACTCCC
TGGATGAATTTATGGCTTGGGTTCTGAAAGTTCAGGCTGACCTGTACTTCCACGATCTGAAATTT
GATGGCGCATTCATCATCAACTGGCTGGAACGTAACGGTTTTAAATGGTCCGCAGATGGTCTGCC
AAATACCTACAACACCATCATTTCTCGCATGGGCCAGTGGTATATGATTGATATTTGCCTGGGTT
ACAAGGGTAAACGCAAGATCCACACCGTGATCTACGACTCTCTGAAGAAACTGCCGTTTCCGGTT
AAGAAAATTGCGAAAGACTTTCAGCTGCCACTGCTGAAAGGCGACATCGACTATCATGCTGAGCG
CCCGGTCGGTCATGAGATCACCCCGGAAGAATATGAATACATTAAAAACGATATTGAAATTATCG
CACGCGCTCTGGACATCCAGTTCAAGCAGGGTCTGGATCGTATGACGGCAGGTTCTGACTCTCTG
AAAGGCTTCAAAGACATTCTGTCTACCAAGAAGTTTAACAAAGTTTTCCCGAAACTGAGCCTGCC
GATGGACAAGGAAATCCGTCGTGCCTACCGTGGTGGTTTCACCTGGCTGAATGACAAATACAAAG
AAAAAGAGATCGGCGAAGGTATGGTTTTTGATGTTAATTCCATGTACCCAGCGATGATGAAAAAC
AAACTGCTGCCGTACGGCGAGCCGGTAATGTTCAAAGGCGAGTACAAGAAAAACGTCGAGTACCC
TCTGTACATTCAGCAGGTGCGTTGTTTCTTTGAACTGAAGAAAGACAAGATCCCGTGCATCCAGA
TCAAGGGCAACGCACGTTTCGGTCAAAACGAATACCTGTCTACCTCCGGCGACGAATACGTGGAC
CTGTACGTGACTAATGTTGATTGGGAACTGATCAAGAAACACTACGACATTTTCGAAGAAGAGTT
CATCGGCGGTTTTATGTTCAAGGGCTTCATTGGCTTCTTCGACGAATACATCGACCGTTTCTTCG
AAATCAAAAACTCTCCATATTCCTCTGCTAAGCAGCTGGCGAAGCTGATGCTGAACAGCCTGTAC
GGTAAATTCGCGACCAACCCGGACGTTACCGGTAAAGTGCCATACCTGAAAGAGAACGGTGCTCT
GGGTTTTCGTCTGGGTGAGGAGGAAACGAAAGACCCTGTATATACCCCGATGGGTGTCTTTATCA
CGGCCTGGGCACGCTTCACGACCATCACGGCAGCGCAGGCTTGTTATGATCGTATTATCTACTGC
GATACCGATTCTATTCACCTGACTGGTACTGAGGTTCCGGAAATTATCAAAGACATCGTAGACCC
GAAGAAACTGGGCTACTGGGCGCACGAATCCACTTTTAAGCGTGCAAAATATCTGCGTCAGAAAA
CCTACATCCAGGATATTTACGTTAAAGAAGTAGACGGCTACCTGAAAGAGTGTTCTCCTGACGAA
GCTACCACTACTAAGTTCTCTGTGAAATGCGCAGGCATGACGGACACCATCAAAAAGAAGGTGAC
TTTCGACAACTTCCGTGTGGGTTTTTCCTCTACTGGCAAACCGAAGCCTGTTCAGGTAAACGGTG
GCGTAGTGCTGGTTGATTCTGTTTTTACTATCAAATAA
```

SEQ ID NO: 20
Amino acid sequence of Φ29-derived DNA polymerase mutant 520P, which comprises the following substitution mutations: N62D, T368F, E375Y, and K512Y

```
MKHMPRKMYSCDFETTTKVEDCRVWAYGYMNIEDHSEYKIGNSLDEFMAWVLKVQADLYPHDLKF
DGAFIINWLERNGFKWSADGLPNTYNTIISRMGQWYMIDICLGYKGKRKIHTVIYDSLKKLPFPV
KKIAKDFKLTVLKGDIDYHKERPVGYKITPEEYAYIKNDIQIIAEALLIQFKQGLDRMTAGSDSL
KGFKDIITTKKFKKVFPTLSLGLDKEVRYAYRGGFTWLNDRFKEKEIGEGMVFDVNSLYPAQMYS
RLLPYGEPIVFEGKYVWDEDYPLHIQHIRCEFELKEGYIPTIQIKRSRFYKGNEYLKSSGGEIAD
LWLSNVDLELMKEHYDLYNVEYISGLKFKATTGLFKDFIDKWFYIKTTSYGAIKQLAKLMLNSLY
GKFASNPDVTGKVPYLKENGALGFRLGEEETKDPVYTPMGVFITAWARYTTITAAQACYDRIIYC
DTDSIHLTGTEIPDVIKDIVDPKKLGYWAHESTFKRAKYLRQKTYIQDIYMKEVDGYLVEGSPDD
YTDIKFSVKCAGMTDKIKKEVTFENFKVGFSRKMKPKPVQVPGGVVLVDDTFTIK
```

ENZYMES RESISTANT TO PHOTODAMAGE

CROSS-REFERENCE TO RELATED APPLICATIONS

This application is a divisional of U.S. patent application Ser. No. 12/384,110, filed Mar. 30, 2009, entitled, "ENZYMES RESISTANT TO PHOTODAMAGE," by Bjornson, Clark, Park, and Christians, which claims priority to and benefit of U.S. Provisional Patent Application No. 61/072,643, filed Mar. 31, 2008, entitled, "ENZYMES RESISTANT TO PHOTODAMAGE," by Bjornson, Clark, Park, and Christians. Each of these applications is incorporated herein by reference in its entirety for all purposes.

FIELD OF THE INVENTION

The invention is in the field of enzyme stability. The invention relates to methods of producing enzymes, e.g., DNA polymerases, having improved photodamage resistance and compositions comprising such enzymes, e.g., for use in single-molecule analyses.

BACKGROUND OF THE INVENTION

Detecting the products of enzymatic reactions, e.g., DNA polymerase reactions, ligase reactions, kinase reactions, phosphatase reactions, and others, is central to molecular and cell biology, genomic analysis, diagnostic medicine, pharmaceutical research, and many other fields of science and medicine. By linking a highly visible signal to a component in an enzymatic reaction, one can better monitor the production, consumption, and/or conversion of reactants and/or products. This strategy can also assist one in identifying any potential effectors or inhibitor of the reaction. Optical labels (e.g., labels having moieties with high quantum yields, such as fluorescent or luminescent moieties) predominate as analytical tools. The widespread adoption of optical labeling methodologies is attributable to their sensitivity and ease of detection, their relative handling safety, and the ease with which they can be integrated with available detection systems (e.g., using microscopes, cameras, photomultipliers, CCD arrays and combinations thereof). For example, high-throughput analysis systems in which optical labels are frequently used include DNA sequencers, array readout systems, cell analysis and sorting systems, and the like. For a brief overview of optical labels, fluorescent products, and technologies see, e.g., Sullivan (ed) (2007) *Fluorescent Proteins*, Volume 85, Second Edition (Methods in Cell Biology) ISBN-10: 0123725585; Hof et al. (eds) (2005) *Fluorescence Spectroscopy in Biology: Advanced Methods and their Applications to Membranes, Proteins, DNA, and Cells* (Springer Series on Fluorescence) ISBN-10: 354022338X; Haughland (2005) *Handbook of Fluorescent Probes and Research Products,* 10th Edition (Invitrogen, Inc./Molecular Probes); *BioProbes Handbook,* (2002) from Molecular Probes, Inc.; and Valeur (2001) *Molecular Fluorescence: Principles and Applications* Wiley ISBN-10: 352729919X.

The detection of optical labels in an enzymatic reaction generally entails directing an excitation radiation source at the reaction mixture to excite the labeling group present in the mixture, which is then separately detectable. However, prolonged exposure of chemical and biochemical reactants to radiation (e.g., light) energy during the excitation and detection of optical labels can damage e.g., enzymes, proteins, substrates, or the like, in the reaction mixture. For example, it has been observed that in template-directed synthesis of nucleic acids comprising fluorescently labeled nucleotides or nucleotide analogs, sustained exposure of the DNA polymerase to excitation radiation used in the detection of the relevant label (e.g., fluorophore) reduces the enzyme's processivity and polymerase activity. Typically, illuminated reactions proceed under conditions wherein the reactants (e.g., enzyme molecules, etc.) are present in excess, such that any adverse effects of photodamage on, e.g., any single enzyme molecule in the reaction mix, do not, in general, affect the operation of the assay.

An increasing number of analyses that entail the use of optical labels are performed with reactants at very low concentrations. For example, polymerases can be used to synthesize DNAs that comprise fluorescently labeled nucleotide analogs in microfluidic or nanofluidic reaction vessels or channels, or in single molecule analyses, e.g., in optically confined reaction volumes, e.g., in a zero-mode waveguide (ZMW) or ZMW array. Analysis of small, single-analyte reaction volumes is becoming increasingly important in high-throughput applications, e.g., in DNA sequencing. However, in such reactant-limited analyses, any degradation of a critical reagent, e.g., an enzyme molecule, due to photodamage, can dramatically interfere with the analysis, e.g., a single-molecule sequencing reaction, by further limiting the reagent.

Enzymes, e.g., DNA polymerases, that exhibit decreased sensitivity to photodamage are desirable for use in a variety of single- or low-number enzyme analyses, including, e.g., DNA sequencing, nucleic acid amplification, labeling reactions, analyte detection assays, kinase assays, phosphatase assays, and others. What are needed in the art are enzymes that exhibit improved tolerance to fluorescence-generated reactive species. What are also needed are methods of making and using such enzymes. The invention described herein fulfills these and other needs, as will be apparent upon review of the following.

SUMMARY OF THE INVENTION

The use of optically detectable labels in enzymatic reactions is ubiquitous throughout cell biology, biochemistry, and molecular medicine. However, the biochemical reactants in reaction mixtures that comprise components are typically damaged and/or inactivated by prolonged exposure to light energy during label detection. The invention is generally directed to modified or engineered enzymes, e.g., DNA polymerases, which are characterized by decreased oxidation and/or by increased resistance to light-generated reactive species. Individually or in combination, these modifications can mitigate the photodamage sustained by enzymes, e.g., DNA polymerases, in reactions that comprise photosensitizers, e.g., fluorescently labeled nucleotides and/or nucleotide analogs in single-molecule sequencing reactions. The invention also provides methods for making enzymes that exhibit increased resistance to photodamage and methods of using polymerases, e.g., produced by the methods, to sequence or make a DNA, e.g., in a zero-mode waveguide (ZMW).

In a first aspect, the invention provides compositions that include a modified recombinant DNA polymerase that comprises at least a first amino acid substitution relative to a parental polymerase, e.g., a wild type or an exonuclease-deficient Φ29 type polymerase. The first substitution replaces a first phenylalanine, tyrosine, tryptophan, histidine, cysteine, or methionine residue in the parental polymerase with a residue less susceptible to oxidation, e.g., an unnatural amino acid, a rare amino acid, or any of the 20 naturally occurring amino acids other than phenylalanine, tyrosine, tryptophan, histidine, cysteine, or methionine. The first replaced residue is, e.g., within 20 Å of a fluorophore that is linked, e.g., covalently attached, to a nucleotide or nucleotide analog in the polymerase active site of the polymerase.

Optionally, the first amino acid substitution is other than a Y369R, a Y369H, or a Y369E substitution, wherein the numbering of amino acid positions is relative to wild-type Φ29 polymerase. The at least first amino acid substitution optionally mitigates photodamage of the modified recombinant polymerase, as compared to the parental polymerase. The amino acid substitution can optionally be a conservative substitution.

The modified recombinant polymerase optionally comprises at least a second amino acid substitution relative to the parental polymerase, which second substitution replaces a second phenylalanine, tyrosine, tryptophan, histidine, cysteine, or methionine residue in the parental polymerase with a residue less susceptible to oxidation, e.g., those described above. The second amino acid substitution is independent of and at a position in the polymerase different from that of the first amino acid substitution. Similarly, the modified recombinant polymerase optionally includes third, fourth, fifth, etc. such substitutions, including replacement of up to all chromophoric or readily oxidized residues in the parental polymerase.

The compositions can optionally include any of a variety of modified recombinant polymerases. For example, the modified recombinant polymerase of the compositions can be a Φ29-type DNA polymerase, e.g., a modified recombinant Φ29, B103, GA-1, PZA, Φ15, BS32, M2Y, Nf, G1, Cp-1, PRD1, PZE, SF5, Cp-5, Cp-7, PR4, PR5, PR722, or L17 polymerase.

The modified recombinant polymerase can optionally comprise an at least first substitution, or combination of substitutions, at position 128, position 137, position 230, position 232, position 246, position 248, position 254, position 300, position 315, position 363, position 367, position 369, position 378, position 385, position 454, position 461, position 482, position 483, position 485, position 489, position 494, position 500, position 505, position 506, position 521, and position 526, wherein numbering of positions is relative to SEQ ID NO: 1. Such substitutions can optionally include M246L, F248L, W367S, Y369V, Y482V, W483S, W483F, W483L, W483V, W483I, W483P, W483Q, H485G, H485N, H485K, H485R, H485A, H485E, H485S, H485I, H485P, H485Q, H485T, H485F, H485G, H485L, Y505V, M506L, Y521V, and F526L. For example, the modified recombinant polymerase of the compositions can optionally be a modified recombinant Φ29 polymerase comprising at least one amino acid substitution or combination of substitutions selected from: M246L, F248L, W367S, Y369V, Y482V, W483S, W483F, W483L, W483V, W483I, W483P, W483Q, H485G, H485N, H485K, H485R, H485A, H485E, H485S, H485I, H485P, H485Q, H485T, H485F, H485G, H485L, Y505V, M506L, Y521V, F526L, M246L and F248L, W367S and Y369V, Y482V and W483S, Y482V and H485G, W483S and H485G, Y505V and M506L, and Y521V and F526L.

The modified recombinant polymerase can optionally be a chimeric polymerase that comprises segments derived from any two or more polymerases, e.g., a B103 polymerase, a GA-1 polymerase, a PZA polymerase, a Φ15 polymerase, a BS32 polymerase, a M2Y polymerase, an Nf polymerase, a G1 polymerase, a Cp-1 polymerase, a PRD1 polymerase, a PZE polymerase, an SF5 polymerase, a Cp-5 polymerase, a Cp-7 polymerase, a PR4 polymerase, a PR5 polymerase, a PR722 polymerase, an L17 polymerase, and/or a F21 polymerase. The chimeric polymerase can optionally include an N62D amino acid substitution, wherein numbering of positions is relative to SEQ ID NO: 1. Optionally, the chimeric polymerase can further include one or two amino acid substitutions selected from the group consisting of: W483F, W483L, W483V, W483I, W483P, W483Q, H485N, H485K, H485A, H485E, H485S, H485I, H485P, H485Q, H485T, H485F, H485G, H485L and H485R.

The invention also provides compositions that include a chimeric polymerase that comprises segments derived from any two or more polymerases, e.g., a B103 polymerase, a GA-1 polymerase, a PZA polymerase, a Φ15 polymerase, a BS32 polymerase, a M2Y polymerase, an Nf polymerase, a G1 polymerase, a Cp-1 polymerase, a PRD1 polymerase, a PZE polymerase, an SF5 polymerase, a Cp-5 polymerase, a Cp-7 polymerase, a PR4 polymerase, a PR5 polymerase, a PR722 polymerase, an L17 polymerase, and/or a F21 polymerase. Optionally, the chimeric polymerases can further comprise an N62D amino acid substitution, wherein numbering of positions is relative to SEQ ID NO: 1.

The invention also provides compositions that include a modified recombinant polymerase that comprises one or two amino acid substitutions selected from: W483F, W483L, W483V, W483I, W483P, W483Q, H485N, H485K, H485A, H485E, H485S, H485I, H485P, H485Q, H485T, H485F, H485G, H485L and H485R, wherein numbering of positions is relative to SEQ ID NO: 1.

The compositions optionally include a nucleotide analog that comprises a covalently bound fluorophore, e.g., a phosphate-labeled nucleotide analog that comprises, e.g., from 3-7 phosphate groups. The compositions can also optionally include both a nucleotide analog, e.g., those described above, and a DNA template, wherein the modified recombinant polymerase incorporates the nucleotide analog into a copy nucleic acid in response to the DNA template. Accordingly, the compositions described above are optionally present in a DNA sequencing system, e.g., a zero-mode waveguide (ZMW). Any of the modified recombinant polymerases described herein can optionally be immobilized on a surface, e.g., in a ZMW, in an optical confinement, in an observation volume, or the like.

The invention also provides compositions comprising a modified recombinant DNA polymerase, which modified recombinant polymerase comprises one or more amino acid substitutions relative to a parental polymerase, which one or more substitutions independently replace one or more phenylalanine, tyrosine, tryptophan, histidine, cysteine, or methionine residues in the parental polymerase with a residue or residues less susceptible to oxidation, e.g., those described above, and which amino acid substitutions mitigate photodamage of the modified recombinant polymerase as compared to the parental polymerase. The modified recombinant polymerase of the compositions can optionally comprise two or more independent substitutions, three or more independent substitutions, etc., that mitigate photodamage of the modified recombinant polymerase. Optionally, the one or more amino acid substitutions is other than a Y369R, Y369H, or Y369E substitution, wherein numbering of positions is relative to SEQ ID NO: 1. Optionally, the one or more amino acid substitutions is within 20 Å of the polymerization active site of the polymerase.

The invention also provides compositions that include a modified recombinant polymerase comprising an amino acid sequence selected from the group of amino acid sequences set forth in SEQ ID NOs: 2, 7, 8, 9, 10, 11, and 12, and conservative variations thereof.

The invention also provides libraries of polymerase mutants comprising two amino acid substitutions. For example, the invention provides a library of polymerase mutants that comprise a first substituted residue at position 483 and a second substituted position at 485. A second library provided by the invention comprises polymerase mutants that comprise a first substituted residue at position 494 and a second substituted position at 500. A third library provided by the invention comprises polymerase mutants that comprise a first substituted residue at position 137 and a second substituted position at 378. Another library provided by the invention comprises polymerase mutants that comprise a first substituted residue at position 230 and a second substituted position at 232. In addition, the invention provides library of polymerase mutants that comprise a first substituted residue at position 300 and a second substituted position at 315. The numbering of positions is relative to SEQ ID NO: 1. The first and second substituted residues in any of the libraries described above can be any amino acid other than tryptophan, tyrosine, methionine, histidine, and cytosine.

The invention also provides a library of polymerase mutants comprising three amino acid substitutions. The polymerase mutants of the library comprise a first substituted residue at position 505, a second substituted residue at position 506, and a third substituted residue at position and 521, wherein numbering of amino acid positions is relative to SEQ ID NO: 1. The first substituted residue can be a glycine, an isoleucine, a leucine, a valine, a tyrosine, an asparagine, a glutamine, a serine, a threonine, a lysine, an aspartic acid, or a glutamic acid. The second substituted residue can be an alanine, an isoleucine, a methionine, a valine, a glutamine, an aspartic acid, or a leucine. The third substituted residue can be an alanine, a tyrosine, a phenylalanine, an isoleucine, a leucine or a threonine.

Additional compositions provided by the invention include any of the polymerase mutants described above further comprising one or more substitution mutations selected from the group consisting of N62D, T368F, E375Y, K512Y, wherein numbering of positions is relative to SEQ ID NO: 1. A composition of the invention can comprise a modified recombinant DNA polymerase that itself comprises a first substitution consisting of N62D, a second substitution consisting of T368F, a third substitution consisting of E375Y, a fourth substitution consisting of K512Y, a fifth substitution at position 483 and a sixth substitution at position 485, wherein numbering of positions is relative to SEQ ID NO: 1.

Essentially all of the features noted for the compositions above apply to these compositions as well, as relevant, for example, with respect to amino acid substitutions, inclusion of analogs, and use in methods, e.g., sequencing a DNA, e.g., in a ZMW, and making a DNA.

In a related aspect, the invention provides methods of sequencing a DNA template. The methods include providing a reaction mixture that comprises a DNA template, a replication-initiating moiety that complexes with or is integral to the template, and one or more nucleotides and/or nucleotide analogs, e.g., any of the nucleotide analogs described above. The reaction mixture also includes any of the recombinant modified polymerases described above, where the polymerase is capable of replicating at least a portion of the template using the moiety in a template-dependent polymerization reaction.

In addition, the invention provides compositions comprising a modified recombinant DNA polymerase that comprises two or more amino acid substitutions relative to a parental polymerase. The substitutions independently replace two or more phenylalanine, tyrosine, tryptophan, histidine, cysteine, or methionine residues in the parental polymerase with a residue or residues less susceptible to oxidation, e.g., those residues described above. Essentially all of the features described for the previous compositions, including their use in methods, e.g., sequencing a DNA, e.g., in a ZMW, and making a DNA, optionally apply to these compositions, as well.

The methods of sequencing a DNA include subjecting the reaction mixture to a polymerization reaction in which the modified recombinant polymerase replicates at least a portion of the template in a template-dependent manner, e.g., whereby the one or more nucleotides and/or nucleotide analogs are incorporated into the resulting DNA; and identifying a time sequence of incorporation of the one or more nucleotides and/or nucleotide analogs into the resulting DNA. For example, different nucleotide analogs can comprise different labels, e.g., fluorophores, which can be distinguished from each other during the identifying step. Subjecting the reaction mixture to a polymerization reaction and identifying a time sequence of incorporation of the nucleotides or nucleotide analogs can optionally be performed in a ZMW.

The invention also provides related methods of making a DNA. Methods of making a DNA include providing a reaction mixture which comprises a template, a replication initiating moiety that complexes with or is integral to the template, one or more nucleotides and/or nucleotide analogs, and any of the modified recombinant polymerases mentioned above, where the polymerase is capable of replicating at least a portion of the template using the moiety in a template-dependent polymerase reaction. These methods include reacting the mixture such that the polymerase replicates at least a portion of the template in a template-dependent manner, whereby the one or more nucleotides and/or nucleotide analogs are incorporated into the resulting DNA. The methods of making a DNA can optionally be performed in a ZMW and can further comprise detecting the incorporation of one or more nucleotide analogs.

Polynucleotides are also a feature of the invention. For example, the invention provides polynucleotides encoding any one of the polymerase comprising an amino acid sequence selected from the group of amino acid sequences set forth in SEQ ID NOs: 2, 7, 8, 9, 10, 11, and 12. In addition, the invention provides compositions that comprise a nucleotide sequence selected from the group of nucleotide sequences set forth in SEQ ID NOs: 13, 14, 15, 16, 17, 18, and 19.

In another aspect, the invention provides methods of increasing a polypeptide's, e.g., an enzyme's, resistance to photodamage. The method includes identifying at least a first amino acid residue position in a parental enzyme as a target for mutation and mutating the enzyme at at least the first position to replace the amino acid residue at the first position in the parental enzyme with a residue less susceptible to oxidation, e.g., as described above, to produce a modified recombinant enzyme. The methods include determining whether the resulting modified recombinant enzyme displays increased resistance to photodamage as compared to the parental enzyme in a reaction mixture comprising a photosensitizer, e.g., a fluorophore or a fluorescently labeled substrate or a fluorogenic substrate for the enzyme.

The amino acid residue at the first position in the parental enzyme that is identified as a target for mutation can optionally include phenylalanine, tyrosine, tryptophan, histidine, cysteine, and methionine. Identifying at least a first target amino acid as a target for mutation can optionally include structurally modeling the parental enzyme, e.g., via rotamer modeling, via homology modeling, or by modeling a derivative of the parental enzyme that comprises conservative amino acid substitutions.

Optionally, the identifying step can include structurally modeling the parental enzyme with a substrate in its active site and identifying one or more residue positions that are within a selected distance from the substrate, e.g., on the surface of the enzyme, or in or near the enzyme active site. For example, one or more residues within 20 Å from a fluorophore that is covalently attached to, e.g., a nucleotide analog in the active site of a polymerase can be identified. The substrate is optionally a fluorescently labeled substrate or a fluorogenic substrate. Optionally the parental enzyme can be modeled with a product in its active site, e.g., a fluorescently labeled product, and the identifying step can include identifying one or more target amino acid residues that are within a selected distance from the product, e.g., as described above.

Optionally, determining whether the resulting modified recombinant enzyme displays increased resistance to photodamage comprises performing parallel reactions, e.g., as described elsewhere herein, e.g., in a ZMW, in an optical confinement, or in an observation volume, using the parental and the modified recombinant polymerases.

The parental enzyme and the recombinant modified enzyme of the methods are optionally DNA polymerases, e.g., Φ29 or Φ29-type DNA polymerases, and the photosensitizer used in the methods is optionally a fluorescently-labeled or fluorogenic nucleotide analog. The first amino acid residue position that is identified as a target for mutation can be, e.g., position 128, position 137, position 230, position 232, position 246, position 248, position 254, position 300, position 315, position 363, position 367, position 369, position 378, position 385, position 454, position 461, position 482, position 483, position 485, position 489, position 494, position 500, position 505, position 506, position 521, and position 526, wherein numbering of positions is relative to SEQ ID NO: 1. For example, the resulting modified recombinant polymerase can comprise one or more of: M246L, F248L, W367S, Y369V, Y482V, W483S, W483F, W483L, W483V, W483I, W483P, W483Q, H485G, H485N, H485K, H485R, H485A, H485E, H485S, H485I, H485P, H485Q, H485T, H485F, H485G, H485L, Y505V, M506L, Y521V, and F526L substitutions. Optionally, the modified recombinant polymerase is a modified recombinant Φ29 polymerase that comprises at least one substitution or combination of substitutions selected from: M246L, F248L, W367S, Y369V, Y482V, W483S, W483F, W483L, W483V, W483I, W483P, W483Q, H485G, H485N, H485K, H485R, H485A, H485E, H485S, H485I, H485P, H485Q, H485T, H485F, H485G, H485L, Y505V, M506L, Y521V, F526L, M246L and F248L, W367S and Y369V, Y482V and W483S, Y482V and H485G, W483S and H485G, Y505V and M506L, and Y521V and F526L, wherein numbering of positions is relative to SEQ ID NO: 1.

Identifying at least a first amino acid residue position in a parental enzyme as a target for mutation can optionally include identifying two or more amino acid residue positions in the parental enzyme as targets for mutation. Accordingly, mutating the enzyme at least at the first position can thus include mutating the enzyme at the two or more amino acid residue positions to independently replace the amino acid residues in the parental enzyme with a residue or residues less susceptible to oxidation. The methods of increasing an enzyme's resistance to photodamage can optionally include making a library of modified recombinant enzymes, with a plurality of members of the library comprising one or more mutations at one or more positions. The library can optionally be screened to identify at least one member exhibiting increased resistance to photodamage as compared to the parental enzyme in a reaction mixture comprising a photosensitizer. The screening step can optionally be used to screen the double and triple substitution mutant libraries described above.

The invention also provides methods of increasing an enzyme's resistance to photodamage that include identifying least two parental enzymes, generating a chimeric enzyme from the at least two parental enzymes, and determining whether the chimeric enzyme displays increased resistance to photodamage as compared to the parental enzymes in a reaction mixture comprising a photosensitizer. Optionally, the enzyme can be a polymerase. Optionally, the method can further comprise mutating one or more residues in the chimeric polymerase selected from the group consisting of: position 128, position 137, position 230, position 232, position 246, position 248, position 254, position 300, position 315, position 363, position 367, position 369, position 378, position 385, position 454, position 461, position 482, position 483, position 485, position 489, position 494, position 500, position 505, position 506, position 521, and position 526, wherein numbering of positions is relative to SEQ ID NO: 1. Optionally, the mutated residues are within 20 Å of an active site.

Essentially all of the features noted for the substitution methods of increasing an enzyme's resistance to photodamage above apply to the chimera methods as well, as relevant, for example, with respect to the photosensitizer used in the methods, where the determining step is performed, etc. These features are also apply to methods of increasing an enzyme's resistance to photodamage that entail introducing the binding site for a triplet state quencher into the parental polypeptide.

In another aspect, the invention provides compositions that include a triplet state quencher, a fluorophore, e.g., other than an amino acid residue, and a polypeptide with which the triplet state quencher and the fluorophore are covalently or noncovalently associated, wherein the triplet state quencher serves as an acceptor for the excited triplet state of the fluorophore. The triplet state quencher can be covalently or non-covalently bound to the polypeptide independent of the manner in which the fluorophore is bound to the polypeptide. Conversely, the fluorophore can be either covalently bound or non-covalently bound to the polypeptide independent of the manner by which the triplet state quencher is bound to the polypeptide.

The fluorophore is intended to comprise a fluorophore exogenous to the peptide sequence, e.g., a moiety other than a natural amino acid in the primary sequence of a polypeptide, which might happen to fluoresce at low levels, e.g., tryptophan. Similarly, the quencher is also intended to comprise a moiety exogenous to the peptide sequence. Optionally, the triplet state quencher can be a trivalent lanthanide ion (e.g., $Eu^{3+}$, $Tb^{3+}$, $Dy^{3+}$, $Gd^{3+}$, or $Sm^{3+}$), 3-carboxy-Proxyl, m-nitrobenzyl alcohol, trimethylsulfonium iodide, N-(2,4-dinitrophenyl) taurine sodium salt, N-(2,4-dinitrophenyl)-sarcosine, M-nitrobenzoic acid, or 4-carboxy-TEMPO.

The polypeptide in the compositions is optionally an enzyme, and the substrate of the enzyme optionally comprises the fluorophore. As just one example, the enzyme can be a DNA polymerase and the substrate a fluorescently labeled nucleotide analog.

In one aspect, the polypeptide comprises a first moiety to which the triplet state quencher is covalently attached, e.g., an unnatural amino acid to which the quencher is bound. In a related aspect, the polypeptide comprises a first moiety to which is covalently attached a second moiety that noncovalently binds the triplet state quencher (e.g., the first moiety can be a cysteine residue to which a chelator for a $Ln^{3+}$ quencher is covalently bound). In another aspect, the polypeptide is a modified recombinant polypeptide that comprises an engineered binding site to which the triplet state quencher can non-covalently bind. Optionally, the engineered binding site can comprise a binding site for a trivalent lanthanide ion, e.g., $Eu^{3+}$ or $Tb^{3+}$. Such an engineered binding site can optionally be produced by mutation of a binding site for one or more divalent metal cations, e.g., in a parental polymerase, nuclease, or phosphatase. As another example, the engineered binding site can comprise an EF hand motif altered to bind $Tb^{3+}$.

The invention also provides compositions that include a triplet state quencher, a fluorescently labeled or fluorogenic nucleotide analog, and a modified recombinant DNA polymerase to which the triplet state quencher is covalently or non-covalently bound. The nucleotide analog of these compositions serves as a substrate for the polymerase, and the triplet state quencher of these compositions serves as an acceptor for the excited triplet state of the fluorescently labeled analog or of the fluorogenic analog's product. The modified recombinant polymerase of the compositions can optionally comprise one or more mutations relative to a parental polymerase that increase the affinity of the recombinant polymerase's exonuclease domain for a trivalent lanthanide ion, e.g., $Eu^{3+}$ or $Tb^{3+}$, relative to the parental polymerase, wherein the lanthanide ion is the triplet state quencher of the composition. The mutations of the modified recombinant polymerase can optionally increase the affinity of the recombinant polymerase's exonuclease domain for a trivalent lanthanide ion by at least 100 fold relative to the parental polymerase, while maintaining the polymerase's polymerase activity.

The modified recombinant polymerase of the compositions can optionally be a modified recombinant Φ29-type DNA polymerase, e.g., a modified recombinant Φ29, B103, GA-1, PZA, Φ15, BS32, M2Y, Nf, G1, Cp-1, PRD1, PZE, SF5, Cp-5, Cp-7, PR4, PR5, PR722, or L17 polymerase. Optionally, the polymerase is exonuclease deficient.

The compositions can optionally include a DNA template, wherein the modified recombinant polymerase incorporates the nucleotide analog into a copy nucleic acid in response to the DNA template. Any of the above-described compositions can optionally be present in a DNA sequencing system, e.g., a ZMW, an optical confinement, or an observation volume. Optionally, the polymerase of any of the compositions described above can be immobilized on a surface, e.g., of a ZMW, an optical confinement, or an observation volume.

The invention provides methods of sequencing a DNA template in which the compositions described above can be used. The methods include providing a reaction mixture comprising a DNA template, a replication initiating moiety that complexes with or is integral to the template, and any one of the compositions described above, wherein the modified recombinant polymerase of the composition is capable of replicating at least a portion of the template using the moiety in a template-dependent polymerization reaction. The reaction mixture can optionally include one or more nucleotides and/or additional nucleotide analogs. The methods of sequencing a DNA include subjecting the reaction mixture to a polymerization reaction in which the modified recombinant polymerase replicates at least a portion of the template in a template-dependent manner, whereby the nucleotides and/or nucleotide analogs are incorporated into the resulting DNA. The methods also include identifying a time sequence of incorporation of the nucleotides and/or nucleotide analogs into the resulting DNA.

The one or more nucleotide analogs that can be included in the reaction mixture can optionally comprise different labels, e.g. fluorophores, e.g., covalently-bound fluorophores, that can be distinguished from one another during the identifying step. Optionally, the subjecting and identifying steps of the methods of sequencing a DNA can be performed in, e.g., a zero mode waveguide, an optical confinement, or an observation volume.

The invention also provides methods of making a DNA, using the compositions described above. The methods include providing a reaction mixture that comprises a template, a replication initiating moiety that complexes with or is integral to the template, any one of the compositions described above, wherein the modified recombinant polymerase is capable of replicating at least a portion of the template using the moiety in a template-dependent polymerase reaction, and optionally one or more nucleotides and/or additional nucleotide analogs. The methods include reacting the mixture such that the polymerase replicates at least a portion of the template in a template-dependent manner, whereby the nucleotides and/or nucleotide analogs are incorporated into the resulting DNA. The methods can optionally be performed in, e.g., a ZMW, an optical confinement, or an observation volume. The methods can optionally further comprise an additional step in which the fluorescently labeled or fluorogenic nucleotide is detected upon incorporation into the resulting DNA. The one or more nucleotide analogs that can be included in the reaction mixture can optionally comprise different labels, e.g. fluorophores, e.g., covalently-bound fluorophores, that can be distinguished from one another during the identifying step. Optionally, the one or more nucleotide analogs that can be included in the reaction mixture can be phosphate-labeled nucleotide analogs, e.g., having from 3-7 phosphate groups.

Another aspect of the invention provides methods of decreasing photosensitivity, e.g., of a modified polypeptide. The methods include introducing a binding site for a triplet state quencher into a parental polypeptide to produce a modified polypeptide and binding the triplet state quencher to the modified polypeptide. The methods also include determining whether, in a mixture comprising a fluorophore and the modified polypeptide with bound quencher, the fluorophore and/or the modified polypeptide display increased resistance to photodamage, as compared to the fluorophore and/or the parental polypeptide in a mixture comprising the fluorophore and the parental polypeptide. The determining step is optionally performed in, e.g., a zero mode waveguide, an optical confinement, or an observation volume.

Introducing the binding site for the quencher into the parental polypeptide can optionally comprise introducing one or more amino acid substitutions, insertions, and/or deletions into the parental polypeptide to produce the modified polypeptide. The triplet state quencher can optionally be covalently attached, e.g., chemically conjugated, to the polypeptide, or it can be non-covalently bound to the modified polypeptide. For example, a binding site for the quencher can be covalently bound to the polypeptide; e.g., an engineered EF hand can be fused with the polypeptide, or a thiol-reactive metal chelator can be conjugated to the polypeptide at a Cys residue.

As another example, the parental polypeptide can optionally comprise a parental polymerase that comprises an exonuclease domain, and the modified polypeptide can optionally comprise a modified recombinant polymerase that comprises an exonuclease domain that exhibits a higher affinity for a trivalent lanthanide ion, e.g., $Eu^{3+}$ or $Tb^3$, than the parental polymerase's exonuclease domain, wherein the trivalent lanthanide ion is the triplet state quencher. Introducing the binding site for the quencher into the parental polypeptide can comprises mutating one or more amino acid residues in the parental polypeptide to result in increased affinity for the trivalent lanthanide ion. Other parental polypeptides that include divalent metal binding sites, such as a parental nuclease or phosphatase, can be similarly engineered to bind a lanthanide ion quencher.

Optionally, the parental and modified polypeptides are enzymes, and the substrate for the modified enzyme optionally comprises the fluorophore. For example, the parental and modified polypeptides can comprise parental and modified DNA polymerases, and a fluorescently or fluorogenically labeled nucleotide analog can comprise the fluorophore. In a preferred embodiment, the modified and parental polymerases are Φ29-type DNA polymerases, e.g., Φ29, B103, GA-1, PZA, Φ15, BS32, M2Y, Nf, G1, Cp-1, PRD1, PZE, SF5, Cp-5, Cp-7, PR4, PR5, PR722, or L17 polymerases.

Those of skill in the art will appreciate that that the methods provided by the invention for modifying an enzyme, e.g., a DNA polymerase, to improve photostability can be used alone or in combination. DNA sequencing systems that include any of the modified polymerases described herein are also a feature of the invention. Such systems can optionally include detectors, array readers, excitation light sources, and the like.

The present invention also provides kits that incorporate the polymerases of the invention, optionally with additional useful reagents such as one or more nucleotide analogs, e.g., for sequencing, nucleic acid amplification, or the like. Such kits can include a polymerase of the invention packaged in a fashion to enable use of the polymerase, a set of different nucleotide analogs of the invention, e.g., those that are analogous to A, T, G, and C, e.g., where one or more of the analogs comprise a detectable moiety, to permit identification in the presence of the analogs. Depending upon the desired application, the kits of the invention optionally include additional reagents, such as natural nucleotides, a control template, and other reagents, such as buffer solutions and/or salt solutions, including, e.g., divalent metal ions, i.e., $Mg^{++}$, $Mn^{++}$, $Ca^{++}$, and/or $Fe^{++}$, standard solutions, e.g., dye standards for detector calibration, etc. Such kits also typically include instructions for use of the compounds and other reagents in accordance with the desired application methods, e.g., nucleic acid sequencing, amplification and the like.

BRIEF DESCRIPTION OF THE DRAWINGS

FIG. 6 provides the nucleic acid and amino acid sequences that find use with the invention.

FIG. 7 provides an alignment of the amino acid sequences of four DNA polymerase chimeras (SEQ ID NOs: 9-12) that exhibit increased resistance to photodamage and the protein sequences of the five parental bacteriophage polymerases (SEQ ID NOs: 2-6) from which they are derived.

DETAILED DESCRIPTION

Overview

Figure 1A:
FIG. 1A shows the nucleotide analog A488dA4P modeled within the active site of a wild type Φ29 polymerase.

The use of optical labels is widespread in many fields of biology and medicine. As used herein, an "optical label" refers to any molecular label, e.g., a fluorescent, a luminescent, a fluorogenic, a chemiluminescent, a chromophoric, or a chromogenic label, that becomes detectable upon absorption of excitation radiation from an illumination source. By linking an optical label to a component in an enzymatic reaction, one can easily monitor the production, consumption, and/or conversion of reactants and/or products. In addition, this strategy can also be used to identify potential effectors and inhibitors of an enzymatic reaction. However, prolonged exposure of chemical and biochemical reactants to illumination during the excitation and detection of optical labels can damage, e.g., enzymes, proteins, substrates, or the like, that are present in the reaction mix. In addition, it has recently been demonstrated that tryptophan residues can facilitate long-range electron transfer between distant metal redox centers in a folded protein (Shih, et al. (2008) "Tryptophan-Accelerated Flow of Electrons through Proteins" *Science* 320: 1760-1762), and this phenomenon can also contribute enzymatic degradation, e.g., via the transmission of energy released by an electronically excited optical label through the protein. Typically, illuminated reactions proceed under conditions wherein the reactants (e.g., enzyme molecules) are present in excess, such that any photodamage sustained by, e.g., any single enzyme molecule in the reaction mix, does not, in general, affect the rate of the reaction. As used herein, an "illuminated reaction" refers to an enzymatic reaction that is exposed to an optical energy source, e.g., light. As used herein, "photodamage" refers generally to any direct or indirect impact of illumination on one or more reagents in an enzymatic reaction, which results in a negative impact upon that reaction. Photodamage includes undesired changes in a reagent that are caused by interaction with, e.g., singlet oxygen generated during the excitation of an optical label.

An increasing number of analyses, e.g., in which optical labels are used, are performed with reactants at very low concentrations. In such reactant-limited analyses, any degradation of a critical reagent, e.g., an enzyme molecule, due to photodamage, can dramatically interfere with the analysis, e.g., a single-molecule sequencing reaction, by further limiting the reagent. In certain photodamage mitigation methods, photoprotective agents can be added to a reaction, e.g., in far excess of the reactants, in order to ensure that the photoprotective effects of the added agents extend to all molecules in the reaction. However, in small volume reactions (e.g., microfluidic, nanofluidic, or "single-molecule" analyses), an excess of photoprotective agents can potentially interfere with the ability of an enzyme to perform its function.

The present invention is generally directed to methods of producing modified enzymes that are characterized by decreased susceptibility to oxidation and/or light-generated reactive species, e.g., relative to the parental enzymes from which they are derived. Two basic approaches to enzyme modification are provided herein. In the first approach, an enzyme of interest is mutated to change photodamage sensitive residues, such as phenylalanine, tyrosine, tryptophan, histidine, cysteine, or methionine, into less sensitive residues. This is particularly useful when the photodamage sensitive residues are proximal to a label, e.g., when a labeled reactant is proximal to the active site of the enzyme. For example, photodamage sensitive amino acid residues proximal to an active site of the enzyme, e.g., a site where a labeled reactant is brought into proximity to the photodamage sensitive residues during an enzymatic reaction using a native enzyme, are preferred targets for modification. In the second approach, a photodamage protective agent is linked to the enzyme, e.g., by recombinant modification of the enzyme to include a binding site for the protective agent, or by incorporating a reactive site into the protein to which the photodamage protective agent can be coupled. For example, the exonuclease site of a polymerase (which is extraneous to many in vitro reactions, such as nucleic acid sequencing) can be modified to bind a triplet state quencher such as a lanthanide; this results in reduced photodamage to the polymerase. As used herein, a "triplet state quencher" is a photoprotective agent that can prevent the formation of triplet state fluorophores, which are often produced in illuminated reactions via photoionization. Triplet state fluorophores are desirably quenched in illuminated reactions because they typically generate highly reactive singlet oxygen species that can damage, e.g., oxidize, enzymes and other reagents in the reaction.

The half-life of an enzyme, e.g., modified according to the methods of the invention, that has been exposed to a known amount of optical energy is, desirably, up to 25% longer, up to 50% longer, up to 100% longer, or, most preferably, more than 100% longer than the half-life of the parental enzyme lacking the photodamage-protective modifications, e.g., after exposure of the parental enzyme to the same amount of optical energy. For example, a DNA polymerase produced by the methods herein can exhibit a half-life, e.g., in the presence of an optical label, that is increased by, e.g., tens of seconds, to, e.g., tens of minutes, or more than tens of minutes, relative to the parental polymerase from which was derived. As used herein, a "parental polymerase" (or "parental enzyme") refers to, e.g., the polymerase (or enzyme) that was modified, e.g., according to the invention, to produce the polymerase mutant (or enzyme mutant) that exhibits increased resistance to photodamage.

While the modified enzymes produced by the methods described herein can be used in any of a variety of assays/analyses that entail the illumination of optical (or photoactivatable) labels, they are of particularly beneficial use in reactant-limited analyses. Enzymes that can particularly benefit from the methods of the invention are DNA polymerases. Modified polymerases provided by the invention are particularly well suited to DNA amplification and/or sequencing applications, particularly sequencing protocols that include detection in real time of the incorporation (e.g., time sequence of incorporation) of fluorescently labeled or fluorogenic nucleotides (and/or nucleotide analogs) into DNA amplicons. (Nucleotide analogs are discussed in further detain hereinbelow.) The invention is particularly advantageous for use in, e.g., single molecule sequencing (SMS). SMS, e.g., using zero-mode waveguide (ZMW) technology, is described in WO 2007/076057 and PCT/US2007/022459, as well as in e.g., U.S. Patent Application Publication No. 2003/0044781, and U.S. Pat. No. 6,917,726, each of which is incorporated herein by reference in its entirety for all purposes. See also Levene et al. (2003) "Zero-mode waveguides for single-molecule analysis at high concentrations" Science 299:682-686 and U.S. Pat. Nos. 7,056,676, 7,056,661, 7,052,847, and 7,033,764, the full disclosures of which are incorporated herein by reference in their entirety for all purposes. The polymerases' decreased susceptibilities to photodamage can permit signal detection of, e.g., fluorescent or fluorogenic labeling groups in, e.g., single molecule reaction volumes, while minimizing the impact of optical energy of the biochemical reactants, e.g., in a sequencing reaction. Increases in a polymerase's tolerance to oxidation and/or photodamage can prolong a polymerase's activity in a reaction mixture, which can in turn maintain the length and accuracy of sequence reads that would otherwise be reduced by damage to or inactivation of the polymerase, e.g., by undesirable side reactions resulting from excitation of a fluorescent label.

The mutations and mutational strategies noted herein can be combined with each other and/or with other photodamage mitigation strategies, e.g., those taught in, e.g., MITIGATION OF PHOTODAMAGE IN ANALYTICAL REACTIONS by Eid et al., WO/2007/064905. It will also be appreciated by those of skill in the art that enzymes modified according to the methods of the invention can optionally be used in reactions that comprise additional photodamage mitigating agents including, but not limited to those described in, e.g., and U.S. patent application Ser. No. 12/367,411, entitled, "CIS REACTIVE OXYGEN QUENCHERS INTEGRATED INTO LINKERS," by Otto, et al., filed Feb. 6, 2009.

The mutations and mutational strategies provided by the invention can also be combined with mutational strategies that provide other desirable features to the enzyme of interest. For example, polymerase enzymes of the invention can include mutations that reduce susceptibility to photodamage, in combination with mutations that permit the enzyme to be bound to a surface (see, e.g., WO 2007/075987 ACTIVE SURFACE COUPLED POLYMERASES by Hanzel et al., and WO 2007/076057 PROTEIN ENGINEERING STRATEGIES TO OPTIMIZE ACTIVITY OF SURFACE ATTACHED PROTEINS by Hanzel et al.), or that display improved activity using various nucleotide analogs useful for various sequencing reaction formats (e.g., WO 2007/076057 POLYMERASES FOR NUCLEOTIDE ANALOG INCORPORATION by Hanzel et al., and PCT/US2007/022459 POLYMERASE ENZYMES AND REAGENTS FOR ENHANCED NUCLEIC ACID SEQUENCING by Rank et al.) or that reduce branching fraction, improve complex stability, or the like, e.g., as taught in U.S. Provisional Patent Application No. 61/072,645 GENERATION OF POLYMERASES WITH IMPROVED CLOSED COMPLEX STABILITY AND BRANCHING RATE, by Clark et al., filed Mar. 31, 2008.

The detailed description is organized to first elaborate the methods provided by the invention for the production of enzymes with increased photostability. Next, details regarding applications in which enzymes, particularly DNA polymerases, are beneficially used are described. Generally applicable methods of modifying enzymes, screening enzymes, particularly DNA polymerases, and making and isolating recombinant enzymes are described thereafter.

Enzymes

An enzyme is a molecule that catalyzes a reaction of interest. Typically, an enzyme is or comprises a polypeptide. A variety of polypeptide enzymes are known, e.g., polymerases (e.g., DNA polymerases, RNA polymerases, reverse transcriptases, terminal transferases), helicases, kinases, caspases, phosphatases, terminal transferases, endonucleases, exonucleases, dehydrogenases, proteases, beta-lactamase, beta-galactosidases, luciferases, etc. Any enzyme can benefit from the methods of reducing photodamage sensitivity provided by the invention. For example, enzymes can be modified by substituting photodamage-sensitive residues, such as phenylalanine, tyrosine, tryptophan, histidine, cysteine, or methionine, with residues less susceptible to oxidation, e.g., by highly reactive singlet oxygen species that can be produced by excitation of an optical label. Residues less susceptible to oxidation can include, e.g., one of the 20 naturally occurring amino acids other than phenylalanine, tyrosine, tryptophan, histidine, cysteine, or methionine, or, e.g., an unnatural or rare amino acid that is not chromophoric and/or that does not contain a sulfur moiety. Alternatively or additionally, enzymes can be modified to comprise a binding site for a triplet state quencher, such as a trivalent lanthanide ion such as $Eu^{3+}$ or $Tb^{3+}$, or any one of a variety of triplet state quenchers, including, but not limited to, e.g., 3-carboxy-proxyl, m-nitrobenzyl alcohol, trimethylsulfonium iodide, N-(2,4-dinitrophenyl) taurine sodium salt, N-(2,4-dinitrophenyl)-sarcosine, M-nitrobenzoic acid, or 4-carboxy-TEMPO.

Methods of making enzymes that display decreased susceptibility to photodamage, and enzymes selected by the methods, are features of the invention.

Known polypeptide enzymes have been grouped into six classes (and a number of subclasses and sub-subclasses) under the Enzyme Commission classification scheme (see, e.g. the Nomenclature Committee of the International Union of Biochemistry and Molecular Biology enzyme nomenclature pages, on the world wide web at www(dot)chem(dot)qmul(dot)ac(dot)uk/iubmb/enzyme), namely, oxidoreductase, transferase, hydrolase, lyase, ligase, and isomerase. Any of these general classes of enzymes can be mutated to display decreased susceptibility to photodamage using the various strategies herein.

Accordingly, the enzyme to be modified according to the methods herein to display enhanced photodamage resistance can be essentially any enzyme. For example, the enzyme can be an oxidoreductase from any one of EC subclasses 1.1-1.21 or 1.97, a transferase from any one of EC subclasses 2.1-2.9 (e.g., a nucleotidyltransferase from sub-subclass 2.7.7, e.g., a DNA-directed DNA polymerase from 2.7.7.7), a hydrolase from any one of EC subclasses 3.1-3.13, a lyase from any one of EC subclasses 4.1-4.6 or 4.99, an isomerase from any one of EC subclasses 5.1-5.5 or 5.99, or a ligase from any one of EC subclasses 6.1-6.6.

In a most preferred aspect, nucleic acid enzymes, such as polymerases, ligases, nucleases, and the like, are preferred classes of enzymes, with polymerases being most preferred. Notwithstanding the foregoing, a wide variety of pharmaceutically relevant enzyme types are of significant interest in conjunction with the present invention, as improved resistance to photodamage in the context of reactions that use only one molecule, or a few molecules, of the enzyme per reaction provide readily analyzable formats for screening for inhibitors, modulators and effectors to such enzyme systems. Such enzymes include kinases, phosphatases, proteases, as well as the aforementioned nucleic acid enzymes.

DNA Polymerases

DNA polymerases are a preferred target for modifications that improve photostability. A wide variety of polymerases that can be modified according to the methods of invention are generally available. DNA polymerases are sometimes classified into six main groups based upon various phylogenetic relationships, e.g., with *E. coli* Pol I (class A), *E. coli* Pol II (class B), *E. coli* Pol III (class C), Euryarchaeotic Pol II (class D), human Pol beta (class X), and *E. coli* UmuC/DinB and eukaryotic RAD30/xeroderma pigmentosum variant (class Y). For a review of recent nomenclature, see, e.g., Burgers et al. (2001) "Eukaryotic DNA polymerases: proposal for a revised nomenclature" *J Biol Chem* 276: 43487-90. For a review of polymerases, see, e.g., Hübscher et al. (2002) "Eukaryotic DNA Polymerases" *Annual Review of Biochemistry* 71: 133-163; Alba (2001) "Protein Family Review: Replicative DNA Polymerases" *Genome Biology* 2: reviews 3002.1-3002.4; and Steitz (1999) "DNA polymerases: structural diversity and common mechanisms" *J Biol Chem* 274: 17395-17398. The basic mechanisms of action for many polymerases have been determined. The sequences of literally hundreds of polymerases are publicly available, and the crystal structures for many of these have been determined, or can be inferred based upon similarity to solved crystal structures for homologous polymerases. For example, the crystal structure of Φ29, a preferred type of parental enzyme to be modified according to the invention, is available. (See, e.g., Berman et al. (2007) "Structures of phi29 DNA polymerase complexed with substrate: the mechanism of translocation in B-family polymerases." *EMBO J* 26: 3494-3505; Kamtekar et al. (2006) "The phi29 DNA polymerase: protein-primer structure suggests a model for the initiation to elongation transition." *EMBO J* 25: 1335-1343; and Kamtekar et al. (2004) "Insights into strand displacement and processivity from the crystal structure of the protein-primed DNA polymerase of bacteriophage phi29." *Mol Cell* 16: 609-618.) Structure/function analysis has revealed that most DNA polymerases comprise a separate exonuclease domain, which, as described elsewhere herein, can be modified to bind a photodamage protective agent, e.g., a trivalent lanthanide ion.

Available DNA polymerase enzymes have also been modified in any of a variety of ways, e.g., to reduce or eliminate exonuclease activities (many native DNA polymerases have a proof-reading exonuclease function that interferes with, e.g., sequencing applications), to simplify production by making protease digested enzyme fragments such as the Klenow fragment recombinant, etc. As noted, polymerases have also been modified to confer improvements in specificity, processivity, and improved retention time of labeled nucleotides in polymerase-DNA-nucleotide complexes (e.g., WO 2007/076057 POLYMERASES FOR NUCLEOTIDE ANALOG INCORPORATION by Hanzel et al., and PCT/US2007/022459 POLYMERASE ENZYMES AND REAGENTS FOR ENHANCED NUCLEIC ACID SEQUENCING by Rank et al.) and to improve surface-immobilized enzyme activities (e.g., WO 2007/075987 ACTIVE SURFACE COUPLED POLYMERASES by Hanzel et al., and WO 2007/076057 PROTEIN ENGINEERING STRATEGIES TO OPTIMIZE ACTIVITY OF SURFACE ATTACHED PROTEINS by Hanzel et al.). Any of these available polymerases can be modified in accordance with the invention to improve photostability (e.g., reduce the photosensitivity) of the polymerase.

Many such polymerases that are suitable for modification are available, e.g., for use in sequencing, labeling and amplification technologies. For example, Human DNA Polymerase Beta is available from R&D systems. DNA polymerase I is available from Epicenter, GE Health Care, Invitrogen, New England Biolabs, Promega, Roche Applied Science, Sigma Aldrich and many others. The Klenow fragment of DNA Polymerase I is available in both recombinant and protease digested versions, from, e.g., Ambion, Chimerx, eEnzyme LLC, GE Health Care, Invitrogen, New England Biolabs, Promega, Roche Applied Science, Sigma Aldrich and many others. Φ29 DNA polymerase is available from e.g., Epicentre. Poly A polymerase, reverse transcriptase, Sequenase, SP6 DNA polymerase, T4 DNA polymerase, T7 DNA polymerase, and a variety of thermostable DNA polymerases (Taq, hot start, titanium Taq, etc.) are available from a variety of these and other sources. Recent commercial DNA polymerases include Phusion™ High-Fidelity DNA Polymerase, available from New England Biolabs; GoTaq® Flexi DNA Polymerase, available from Promega; RepliPHI™ Φ29 DNA Polymerase, available from Epicentre Biotechnologies; PfuUltra™ Hotstart DNA Polymerase, available from Stratagene; KOD HiFi DNA Polymerase, available from Novagen; and many others. Biocompare(dot)com provides comparisons of many different commercially available polymerases.

DNA polymerases that are preferred substrates for mutation to increase photostability include Taq polymerases, exonuclease deficient Taq polymerases, E. coli DNA Polymerase 1, Klenow fragment, reverse transcriptases, Φ29 related polymerases including wild type Φ29 polymerase and derivatives of such polymerases such as exonuclease deficient forms, T7 DNA polymerase, T5 DNA polymerase, an RB69 polymerase, etc.

In one aspect, the polymerase that is modified to have increased photostability is a Φ29-type DNA polymerase. For example, the modified recombinant DNA polymerase can be homologous to a wild-type or exonuclease deficient Φ29 DNA polymerase, e.g., as described in U.S. Pat. Nos. 5,001,050, 5,198,543, or 5,576,204. Alternately, the modified recombinant DNA polymerase can be homologous to other Φ29-type DNA polymerases, such as B103, GA-1, PZA, Φ15, BS32, M2Y, Nf, G1, Cp-1, PRD1, PZE, SF5, Cp-5, Cp-7, PR4, PR5, PR722, L17, D21, or the like. For nomenclature, see also, Meijer et al. (2001) "Φ29 Family of Phages" Microbiology and Molecular Biology Reviews, 65(2):261-287.

Figure 7:
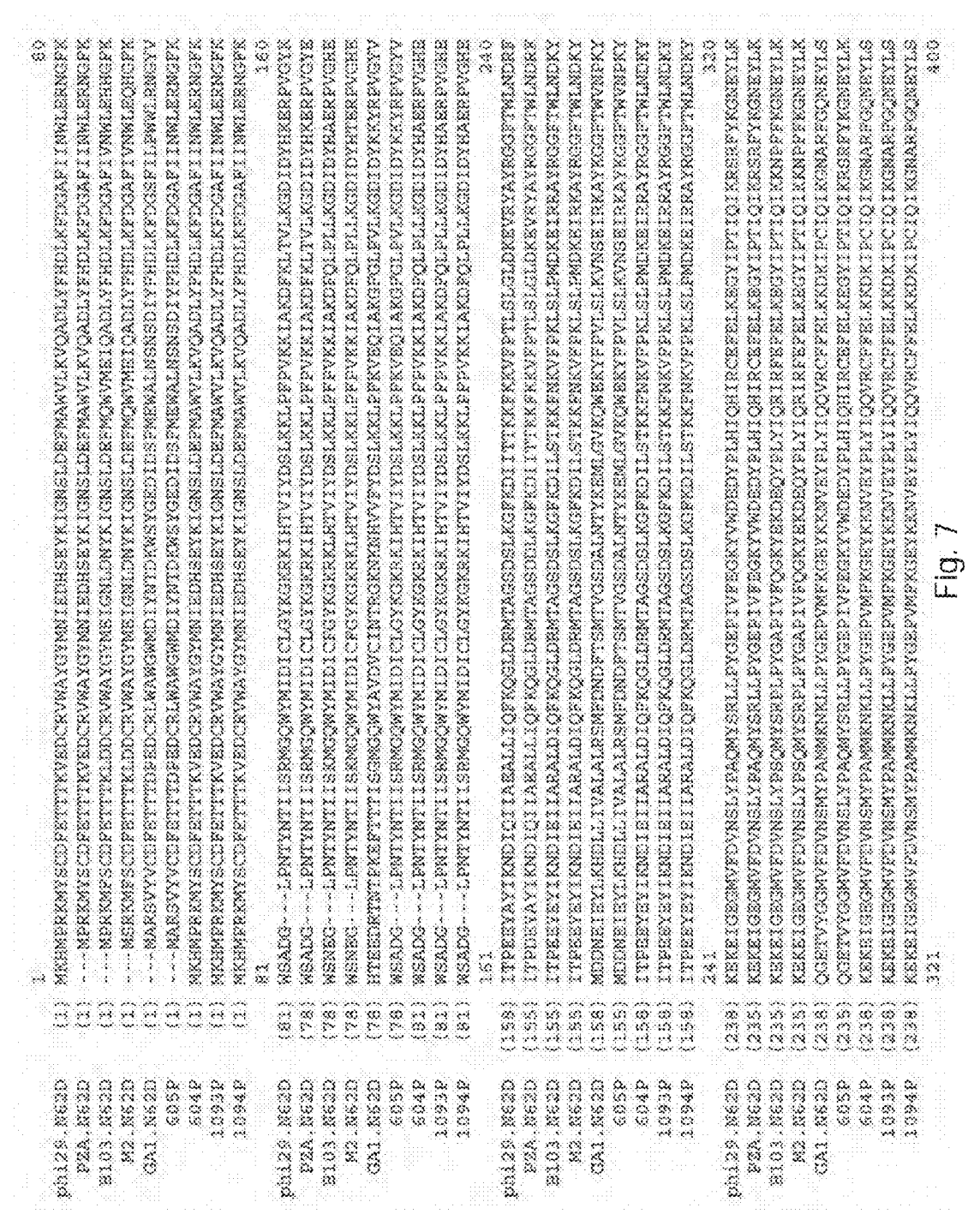
Figure 7:
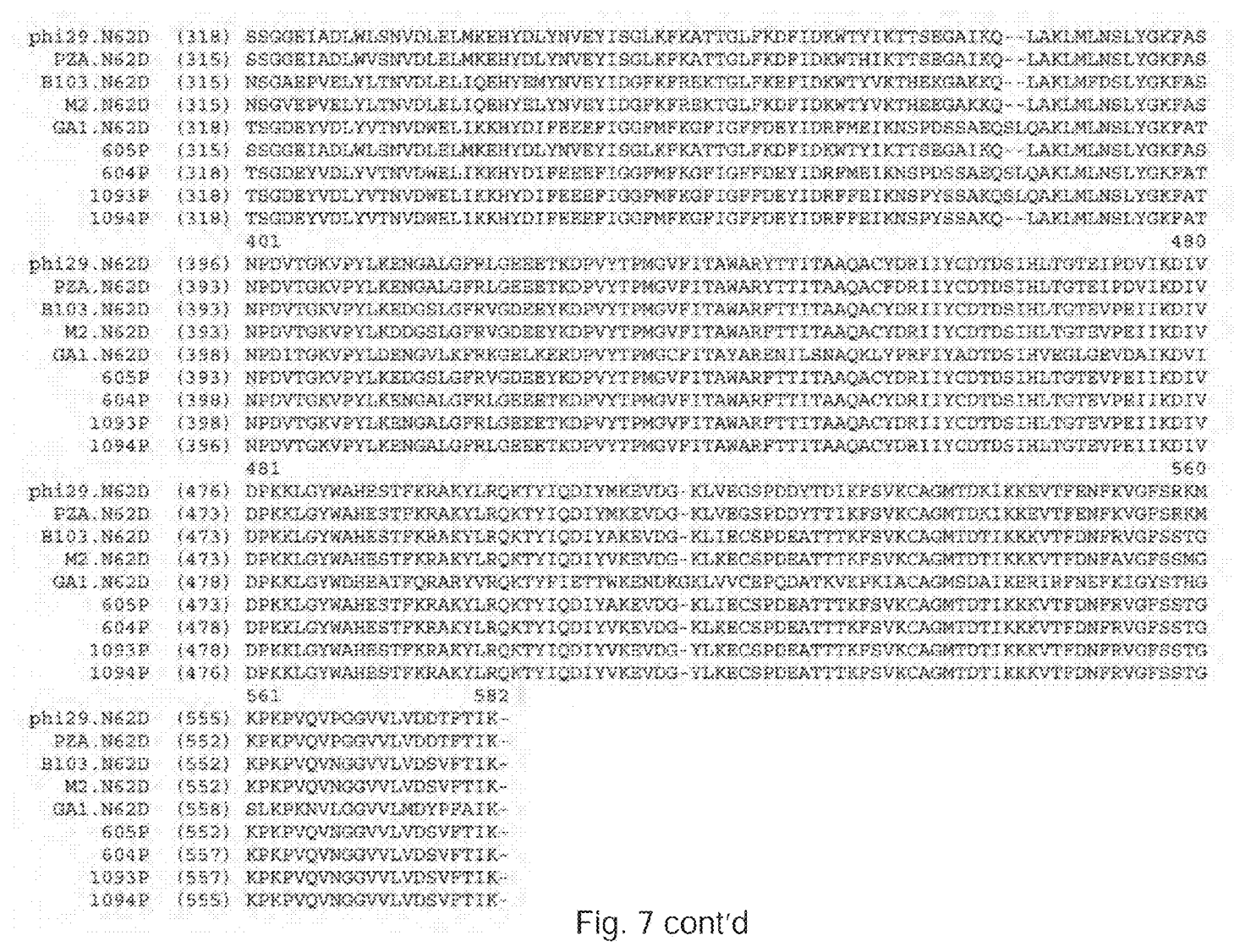

In addition to wild-type polymerases, chimeric polymerases made from a mosaic of different sources can be used. For example, chimeric polymerases made by taking sequences from more than one parental polymerase into account can be used as a starting point for mutation to produce the polymerases of the invention. This can done, e.g., using consideration of similarity regions between the polymerases to define consensus sequences that are used in the chimera, or using gene shuffling technologies in which multiple Φ29-related polymerases are randomly or semi-randomly shuffled via available gene shuffling techniques (e.g., via "family gene shuffling"; see Crameri et al. (1998) "DNA shuffling of a family of genes from diverse species accelerates directed evolution" Nature 391: 288-291; Clackson et al. (1991) "Making antibody fragments using phage display libraries" Nature 352: 624-628; Gibbs et al. (2001) "Degenerate oligonucleotide gene shuffling (DOGS): a method for enhancing the frequency of recombination with family shuffling" Gene 271: 13-20; and Hiraga and Arnold (2003) "General method for sequence-independent site-directed chimeragenesis." J Mol Biol 330: 287-296). In these methods, the recombination points can be predetermined such that the gene fragments assemble in the correct order. However, the combinations, e.g., chimeras, can be formed at random. Using the methods described above, a chimeric polymerase, e.g., comprising segments of, e.g., a B103 polymerase, a GA-1 polymerase, a PZA polymerase, a Φ15 polymerase, a BS32 polymerase, a M2Y polymerase, an Nf polymerase, a G1 polymerase, a Cp-1 polymerase, a PRD1 polymerase, a PZE polymerase, an SF5 polymerase, a Cp-5 polymerase, a Cp-7 polymerase, a PR4 polymerase, a PR5 polymerase, a PR722 polymerase, an L17 polymerase, and/or an F21 polymerase, that exhibits increased resistance to photodamage can be generated. As used herein, a "segment" refers to a contiguous sequence of amino acids derived from, e.g., a parental polymerase, that appears in the same order in, e.g., a chimeric polymerase. FIG. 7 provides an alignment of the protein sequences of four DNA polymerase chimeras, 604P, 605P, 1093P and 1094P (e.g., SEQ ID NOs: 9-12) that exhibit increase resistance to photodamage and the protein sequences of the five parental bacteriophage polymerases (e.g., SEQ ID NOs: 2-6) from which they are derived. In addition to combining segments from different parental enzymes, chimeric polymerases of the invention can also comprise any one or more of the mutations described herein.

Mutations that Modify Photosensitive Amino Acid Residues

The invention provides methods for generating recombinant polymerases that comprise modifications that increase the resistance of the polymerase active site to oxidation, e.g., due to extended exposure to optical energy emitted by an excitation light source and/or to reactive species resulting from collision with an excited fluorescently labeled nucleotide or nucleotide analog. For example, an optical label tethered to a nucleotide positioned within a small distance, e.g., 50 Å, 20 Å, 10 Å, or less than 10 Å of the active site of the protein can create a reactive species, e.g., singlet oxygen, that will diffuse to and interact with sensitive residues, e.g., chromophoric or oxidizable residues, within and near the binding pocket. In certain embodiments of the invention, replacing at least one such spatially susceptible chromophoric or oxidizable amino acid with an amino acid residue that is less susceptible to oxidation, e.g., one of the 20 naturally occurring amino acids other than phenylalanine, tyrosine, tryptophan, histidine, cysteine, or methionine, or, e.g., an unnatural or rare amino acid that is not chromophoric and/or that does not contain a sulfur moiety, can produce a protein that is more stable in the presence of optic energy.

Modification of a polymerase, e.g., any of the polymerases described herein, including chimeras, or polymerases homologous to those described herein, by using this strategy, or any combination of the strategies described herein, can increase a polymerase's tolerance to oxidation, e.g., as a result of exposure to singlet oxygen that can be produced by excitation of a fluorescent label. Modified recombinant polymerases that exhibit increased resistance to photodamage and/or oxidation, e.g., a reduced rate of inactivation, can comprise at least one amino acid substitution or a combination of amino acid substitutions relative to the parental polymerase, wherein a phenylalanine, tyrosine, tryptophan, histidine, cysteine, or methionine, e.g., within 50 Å, within 20 Å, within 15 Å, within 10 Å, or within 5 Å of a fluorophore linked to a nucleotide or a nucleotide analog that occupies the polymerase active site, is replaced by a less sensitive residue, e.g., those described above. Φ29 polymerases (and homologs thereof) that include a Y369R, Y369H, or Y369E mutation, or any combination thereof, have been described previously WO 2007/076057 POLYMERASES FOR NUCLEOTIDE ANALOG INCORPORATION, by Hanzel et al. Thus, substitutions that can improve the photostability of polymerases optionally comprise first substitutions other than those that correspond to Y369R, Y369H, or Y369E in a wild-type Φ29 polymerase, although the modified polymerases can comprise the aforementioned mutations in combination with other substitutions.

Figure 1B:
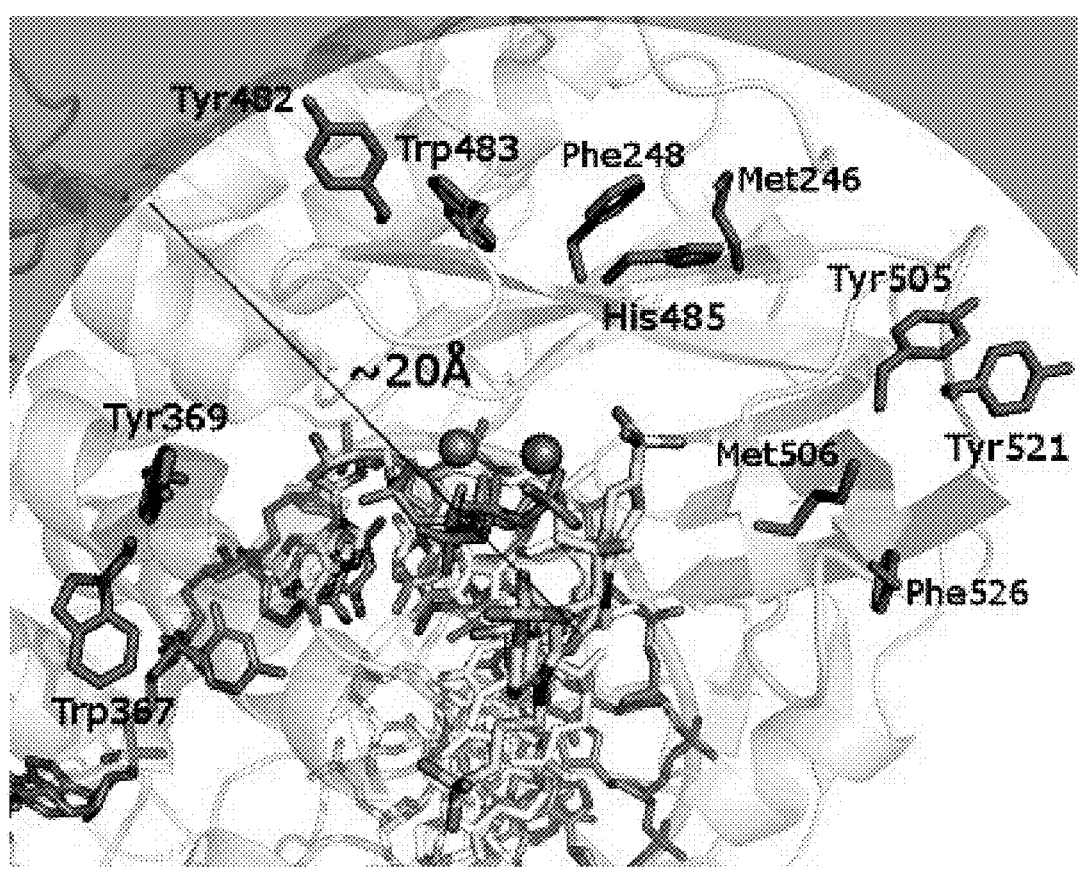
FIGS. 1B and 1C show the crystal structure of a wild type Φ29 polymerase complexed with the nucleotide analog A555dG6P viewed from two different angles.
Figure 1C:
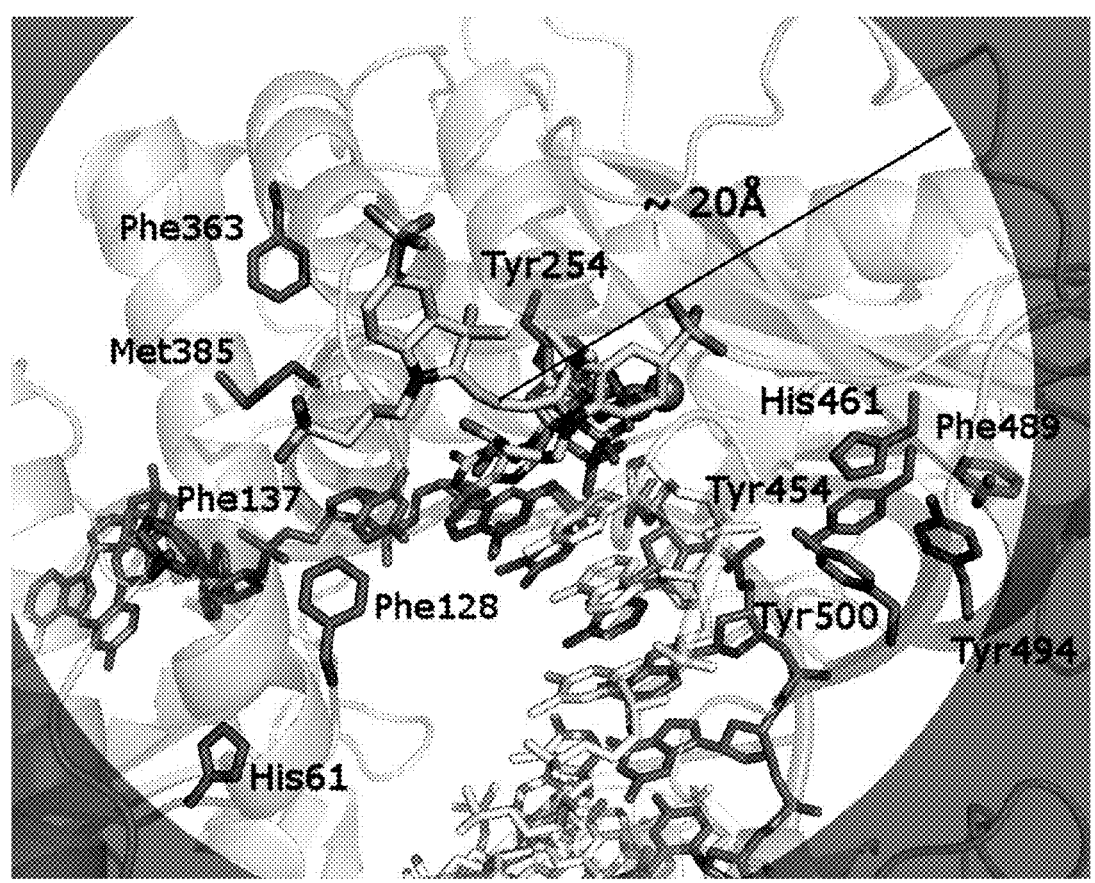
Figure 1D:
FIG. 1D shows a crystal structure of a Φ29 polymerase mutant comprising the substitution mutations D12A, D66A, T386F, E375Y, K512Y complexed with the nucleotide analog A555dG6P.

Structure/function modeling, e.g., as described herein below, can be used to identify residues for replacement, for example, by identifying residues that are within a fixed diffusional distance between, e.g., the photosensitizer and susceptible residues in, e.g., a polymerase nucleotide binding pocket or on the surface of the enzyme. As used herein, a "photosensitizer" is a moiety, such as an optical label, that can cause photodamage. For example, FIG. 1A shows the nucleotide analog A488dA4P modeled within the active site of a wild type Φ29 polymerase. The active site of the polymerase is represented in FIG. 1A in ribbon model format, and the nucleotide analog is represented in FIG. 1A in stick format. FIGS. 1B and 1C show a crystal structure of a wild type Φ29 polymerase complexed with the nucleotide analog A555dG6P viewed from two different angles. The amino acids in the active site of the polymerase that are within a 20 Å radius of the fluorophore A555 are labeled. These amino acids are possible mutation targets. FIG. 1D shows a crystal structure of a Φ29 polymerase mutant comprising the substitution mutations D12A, D66A, T386F, E375Y, K512Y complexed with the nucleotide analog A555dG6P. The amino acids in the active site of the polymerase mutant that are within a 20 Å radius of the fluorophore are indicated in light gray. Nucleotides or nucleotide analogs that are "complexed with" a polymerase typically occupy the polymerase's active site.

Residue(s) identified as targets for replacement can be replaced with a residue or residues selected using, e.g., energy minimization modeling, rotamer databases, homology modeling, and/or conservative amino acid substitutions to determine best case selections derived from known best substitution tables. Such strategies are well known in the art and are also described hereinbelow; see also, e.g., Bordo, et al., (1991) "Suggestions for "Safe" Residue Substitutions in Site-Directed Mutagenesis." *J Mol Biol* 217: 721-729. These strategies can be used to generate a library of mutants with desired substitutions, which can then be assayed for photostability relative to a parental polymerase, as described elsewhere herein. Generation of libraries is similarly well described in the art; see, e.g., Hayes, et al. (2002) "Combining computational and experimental screening for rapid optimization of protein properties." *Proc Natl Acad Sci, USA* 99: 15926-15931.

A number of specific examples are described herein. For example, relative to a wild-type Φ29 DNA polymerase, these modifications, in addition to those described above, e.g., within 20-50 Å of an optical label, can include any one or any combination of substitutions including, but not limited to: an amino acid substitution at position 128, 137, 230, 232, 246, 248, 254, 300, 315, 363, 367, 369, 378, 385, 454, 461, 482, 483, 485, 489, 494, 500, 505, 506, 521, and/or 526. The at least first substitution or combination of substitutions in a polymerase that can increase a polymerase's resistance to photodamage can include: M246L, F248L, W367S, Y369V, Y482V, W483S, W483F, W483L, W483V, W483I, W483P, W483Q, H485G, H485N, H485K, H485R, H485A, H485E, H485S, H485I, H485P, H485Q, H485T, H485F, H485G, H485L, Y505V, M506L, Y521V, F526L, M246L and F248L, W367S and Y369V, Y482V and W483S, Y482V and H485G, W483S and H485G, Y505V and M506L, and Y521V and F526L. (See Tables 1 and 2.) Additional conservative substitutions can also be made. Optionally, any amino acid, e.g., natural, unnatural, or rare amino acid that is not chromophoric and/or that does not contain a sulfur moiety can be substituted at amino acid position 485, e.g., wherein the numbering of positions is relative to a wild-type Φ29 polymerase (e.g., SEQ ID NO: 1). Useful libraries of double substitution mutants and triple substitution mutants are provided in Tables 3 and 4 hereinbelow. Any number of these mutations can be combined with others, e.g., mutations to improve enzyme kinetics. In addition, these mutations can be used in chimeric polymerases, e.g., wherein the numbering of positions is relative to a wild-type Φ29 polymerase (e.g., SEQ ID NO: 1), to provide further improvement in photoresistance.

Modifying Domains to Bind Photodamage Protective Agents

In other embodiments of the invention, enzymes can be modified to comprise domains that bind photoprotective agents, e.g., triplet state quenchers, which can mitigate the degree of photodamage sustained by an enzyme e.g., by quenching the triplet excited state of a fluorophore and thereby preventing or decreasing formation of reactive species that can damage the enzyme. As used herein, a "photoprotective agent" refers to an agent that can prevent or mitigate the damages caused by illumination. In one implementation, an existing domain of an enzyme, e.g., a domain not related to the activity or function of interest, e.g., synthesizing a DNA, can be modified, e.g., by any one or combination of mutational strategies described elsewhere herein, e.g., without altering the enzyme's activity or function of interest, to exhibit an increased affinity for binding, e.g., noncovalent binding, of a photoprotective agent, e.g., a trivalent lanthanide ion such as $Eu^{3+}$, $Tb^{3+}$, $Dy^{3+}$, $Gd^{3+}$, or $Sm^{3+}$, which, via energy transfer (preferably, e.g., radiationless energy transfer) or collisional mechanisms, can effectively in shorten the triplet state lifespan of, e.g., a fluorophore in the enzyme's active site.

In one example of interest, a DNA polymerase's exonuclease active site can be exploited to prolong the polymerase activity of a polymerase in the presence of, e.g., an excited fluorophore. Most DNA polymerases comprise distinct exonuclease domains to which divalent metal cations, e.g., $Mg^{2+}$, $Mn^{2+}$, $zn^{2+}$, or $Co^{2+}$, bind and serve in the exonuclease-catalyzed hydrolysis of DNA. Other metal ions, e.g., trivalent lanthanides such as $Eu^{3+}$ and $Tb^{3+}$, can bind the exonuclease active site with reduced affinity, and this binding concomitantly inhibits exonuclease activity (Frey, et al. (1996) "Elucidation of the metal-binding properties of the Klenow fragment of *Escherichia coli* polymerase I and bacteriophage T4 DNA polymerase by lanthanide (III) luminescence spectroscopy." *Chemistry and Biology* 3: 393-403; Brautigam, et al, (1999) "Structural elucidation of the binding and inhibitory properties of lanthanide (III) ions at the 3'-5' exonucleolytic active site of the Klenow fragment." *Chemistry and Biology* 6: 901-908). The exonuclease site can be modified, e.g., using molecular evolution strategies, rational design, and/or other mutational strategies described elsewhere herein, to preferentially bind a lanthanide ion while maintaining a high affinity for $Mg^{2+}$ or $Mn^{2+}$ in the polymerase active site. Such modifications can include enlarging the metal binding site in the polymerase exonuclease domain, e.g., to better accommodate the lanthanide ion, or mutating amino acid residues to coordinate with the lanthanide metal. Most desirably, a polymerase's exonuclease domain's affinity for a lanthanide ion can be increased by more than 100-fold, preferably more than 1000-fold. A bound lanthanide such as europium or terbium can serve as an efficient acceptor moiety for the excited triplet state of, e.g., a fluorescently labeled nucleotide or nucleotide analog occupying the nucleotide binding pocket In another implementation, a domain that, e.g., non-covalently binds a photoprotective agent, e.g., a triplet state quencher, can be covalently linked to an enzyme of interest at a defined position and can thereby increase the enzyme's photostability, e.g., by minimizing the generation of reactive singlet oxygen by a triplet state fluorophore. For example, an EF-hand motif derivative that binds $Tb^{3+}$ can be engineered at a defined location of an enzyme of interest where it can protect photosensitive residues, e.g., within a defined diffusional distance from a source of optical energy, e.g., by quenching the triplet state of, e.g., a fluorophore. A useful EF-hand motif has been described in Vazquez-Ibar (2002) "Engineering a terbium-binding site into an integral membrane protein for luminescence energy transfer." *Proc Natl Acad Sci USA* 99: 3487-3492.

In addition, the strategy of providing a triplet state quencher bound to the enzyme can also mitigate photobleaching, which can occur as a result of triplet state excitation (Widengren, et al. (2007) "Strategies to Improve Photostabilities in Ultrasensitive Fluorescence Spectroscopy." *J Phys Chem* 111: 429-440). Those of skill in the art will appreciate that such modifications most beneficially preserve the enzyme's activity or function of interest.

Linking Photoprotective Groups Directly to Enzymes

Enzymes can be modified to include residues that provide for convenient coupling of photodamage protective agents (e.g., lanthanide ions such as $Eu^{3+}$ or $Tb^{3+}$, or other triplet state quenchers such as a 3-carboxy-Proxyl, m-nitrobenzyl alcohols, trimethylsulfonium iodide, N-(2,4-dinitrophenyl) taurine sodium salt, N-(2,4-dinitrophenyl)-sarcosine, M-nitrobenzoic acid, 4-carboxy-TEMPO, ascorbic acid, dithiothreitol (DTT), mercaptoethylamine (MEA), beta-mercaptoethanol (BME), n-propyl gallate, p-phenylenediamine (PPD), hydroquinone, sodium azide ($NaN_3$), diazobicyclooctane (DABCO), cyclooctatetraene (COT), and 3-nitrobenzoic acid (NBA), as well as commercially available anti fade agents, such as Fluoroguard (available from Bio-Rad Laboratories, Inc., Hercules, Calif.), Citifluor antifadants (Citifluor, Ltd., London, UK), ProLong, SlowFade, and SlowFade Light (Invitrogen/Molecular Probes, Eugene, Oreg.) or the like). These can include the incorporation of reactive natural or unnatural amino acids into the protein (if a suitable reactive residue is not already available), followed by standard chemical linkage of the photodamage protective agents to the reactive amino acid. Suitable coupling chemistries for such linkage are well known in the art; see, e.g., CIS REACTIVE OXYGEN QUENCHERS INTEGRATED INTO LINKERS, by Otto, et al, filed Feb. 7, 2008.

In one implementation, reactive sites are incorporated into the enzymes, e.g., by site-specifically incorporating unnatural amino acids into the relevant enzyme (e.g., within 20 angstroms of a label moiety when the label is in the active site of the enzyme). Technology for the site-specific incorporation of unnatural amino acids is available, e.g., using systems of orthogonal expression elements, e.g., as reviewed in Wang et al., (2006) "Expanding the Genetic Code." *Annu Rev Biophys Biomol Struct* 35: 225-24; Wang and Schultz, (2005) "Expanding the Genetic Code." *Angewandte Chemie Int Ed* 44: 34-66; Xie and Schultz, (2005) "An Expanding Genetic Code." *Methods* 36: 227-238; Xie and Schultz, (2005) "Adding Amino Acids to the Genetic Repertoire." *Curr Opinion in Chemical Biology* 9: 548-554; and United States Patent Application Publications Nos. 2006/0068478, 2005/0227318, and 2006/0073507. As another example, a thiol-reactive chelator for $Tb^{3+}$ (e.g., Cha, et al. (1999) "Atomic scale movement of the voltage-sensing region in a potassium channel measured via spectroscopy." *Nature* 402: 809-813; Xiao, et al. (1998) "Conformational changes between the active-site and regulatory light chain of myosin as determined by luminescence resonance energy transfer: the effect of nucleotides and actin." *Proc Natl Acad Sci USA* 95: 15309-15314; Getz, et al. (1998) "Luminescence resonance energy transfer measurements in myosin." *Biophys J* 74: 2451-2458; Heyduk (2001) "Luminescence resonance energy transfer analysis of RNA polymerase complexes." *Methods* 25: 44-53; Root (1997) "In situ molecular association of dystrophin with actin revealed by sensitized emission immuno-resonance energy transfer." *Proc Natl Acad Sci USA* 94: 5685-5690) can be reacted with a cysteine or other thiol-containing residue in the enzyme. The covalent linking of a triplet state quencher to an enzyme of interest can also mitigate photobleaching, which can result from triplet state excitation.

While the above methods for improving enzyme photostability are described in the context of improving DNA polymerase photostability, it will be appreciated that the invention can find utility with any enzyme that is desirably modified to exhibit increased resistance to photodamage. It will also be appreciated by those of skill in the art that the modifications described above can be used alone or in combination to produce enzymes, e.g., polymerases that are useful in a variety of illuminated analyses, e.g., DNA sequencing, PCR amplification, and others, including, e.g., low-reactant or "single molecule" applications, such as single-molecule sequencing. Such applications are described in further detail below.

Further Details Regarding Applications for Modified DNA Polymerases and Other Enzymes Exhibiting Increased Photostability Polymerases of the invention, e.g., modified recombinant polymerases, are optionally used in combination with nucleotides and/or nucleotide analogs, and nucleic acid templates (DNA or RNA) to copy template nucleic acids, e.g., to replicate a nucleic acid molecule to generate a new nucleic acid that comprises a sequence complementary to that of the original. That is, a mixture of the polymerase, nucleotides/analogs, the template and a replication initiating moiety (e.g., a primer or the like), and optionally other appropriate reagents, is reacted such that the polymerase synthesizes nucleic acid (e.g., extends the primer) in a template-dependent manner, e.g., produces a DNA that comprises a sequence complementary to that of the template. The replication initiating moiety can be a standard oligonucleotide primer, or, alternatively, a component of the template, e.g., the template can be a self-priming single stranded DNA, a nicked double stranded DNA, or the like. Similarly, a terminal protein can serve as a initiating moiety. At least one nucleotide analog can be incorporated into the DNA. The template DNA can be a linear or circular DNA, and in certain applications, is desirably a circular template (e.g., for rolling circle replication or for sequencing of circular templates). Optionally, the composition can be present in an automated DNA replication and/or sequencing system.

Incorporation of labeled nucleotide analogs into a DNA by the polymerases of the invention is particularly useful in a variety of different nucleic acid analyses, including real-time monitoring of DNA polymerization, e.g., during a sequencing reaction, during PCR amplification, etc. The label can itself be incorporated, or more preferably, can be released during incorporation of the analog. For example, analog incorporation can be monitored in real-time by observing label release during incorporation of the analog into, e.g., a nascent and growing DNA strand, by the polymerase. The portion of the analog that is incorporated can optionally be the same as a natural nucleotide, or it can include features of the analog that differ from a natural nucleotide.

In general, label incorporation or release can be used to indicate the presence and composition of a growing nucleic acid strand, e.g., providing evidence of template replication/amplification and/or sequence of the template. Signaling from the incorporation can be the result of detecting labeling groups that are liberated from the incorporated analog, e.g., in a solid phase assay, or can arise upon the incorporation reaction. For example, in the case of FRET labels where a bound label is quenched and a free label is not, release of a label group from the incorporated analog can give rise to a fluorescent signal. Alternatively, the enzyme may be labeled with one member of a FRET pair proximal to the active site, and incorporation of an analog bearing the other member will allow energy transfer upon incorporation. The use of enzyme bound FRET components in nucleic acid sequencing applications is described, e.g., in United States Patent Application Publication No. 2003/0044781, incorporated herein by reference.

In one example reaction of interest, a polymerase reaction can be isolated within an extremely small observation volume that effectively provides observation of individual polymerase molecules. As a result, the incorporation event provides observation of an incorporating nucleotide analog that is readily distinguishable from non-incorporated nucleotide analogs. In a preferred aspect, such small observation volumes are provided by immobilizing the polymerase enzyme within an optical confinement, such as a Zero Mode Waveguide (ZMW). For a description of ZMWs and their application in single molecule analyses, and particularly nucleic acid sequencing, see, e.g., United States. Patent Application Publication No. 2003/0044781, and U.S. Pat. No. 6,917,726, each of which is incorporated herein by reference in its entirety for all purposes. See also, e.g., Levene et al. (2003) "Zero-mode waveguides for single-molecule analysis at high concentrations" Science 299:682-686; Eid, et al. (2009) "Real-Time DNA Sequencing from Single Polymerase Molecules." *Science* 323:133-138, and U.S. Pat. Nos. 7,056,676, 7,056,661, 7,052,847, and 7,033,764, the full disclosures of which are incorporated herein by reference in their entirety for all purposes.

In a template replication reaction, e.g., a sequencing reaction or a nucleic acid amplification reaction, a polymerase enzyme is generally complexed with the template strand in the presence of one or more nucleotides and/or one or more nucleotide analogs. For example, in certain embodiments, optically labeled analogs, e.g., such as fluorescently labeled analogs, are present representing analogous compounds to each of the four natural nucleotides, A, T, G and C, e.g., in separate polymerase reactions, as in classical Sanger sequencing, or multiplexed together, e.g., in a single reaction, as in multiplexed sequencing approaches. When a particular base in the template strand is encountered by the polymerase during the polymerization reaction, it complexes with an available analog that is complementary to such template nucleotide. The complementary analog is incorporated into the nascent and growing nucleic acid strand by the polymerase. In one aspect, incorporation can result in a label being released, e.g., in polyphosphate analogs, cleaving between the $\alpha$ and $\beta$ phosphorus atoms in the analog, and, consequently, releasing the labeling group (or a portion thereof). The incorporation event is detected, either by virtue of a longer presence of the analog and, thus, the label, in the complex, or by virtue of release of the label group into the surrounding medium. Where different labeling groups are used for each of the types of analogs, e.g., A, T, G or C, identification of a label of an incorporated analog allows identification of that analog and consequently, determination of the complementary nucleotide in the template strand being processed at that time. Sequential reaction and monitoring permits real-time monitoring of the polymerization reaction and determination of the sequence of the template nucleic acid. As noted above, in particularly preferred aspects, the polymerase enzyme/template complex is provided immobilized within an optical confinement that permits observation of an individual complex, e.g., a zero mode waveguide.

In addition to their use in sequencing, the polymerases of the invention are also useful in a variety of other genotyping analyses, e.g., SNP genotyping using single base extension methods, real time monitoring of amplification, e.g., RT-PCR and LCR methods, methods the include optically labeled molecular beacons, and the like. Further details regarding sequencing and nucleic acid amplification can be found, e.g., in Sambrook, Ausubel, and Innis, all infra. Those of skill in the art are familiar with a variety of applications in which polymerases of the invention can be beneficially used. Those listed above are not to be taken as limiting.

Improved Nucleic Acid Sequencing

DNA polymerases can be used to synthesize DNAs using fluorescently labeled nucleotide analogs in microfluidic or nanofluidic reaction vessels or channels, or in single molecule analyses, e.g., in optically confined reaction volumes, e.g., in a zero-mode waveguide (ZMW) or ZMW array. Analysis of small single-analyte molecule reaction volumes are becoming increasingly important in high throughput applications, e.g., in DNA sequencing. However, when reactions with a few or even just a single template or polymerase enzyme are present in a reaction volume, damage to the DNA polymerase by exposure to optical energy during fluorescent or chemiluminescent detection can have a detrimental effect on the real time analysis of e.g., a single-molecule sequencing reaction. Polymerases that exhibit increased photostability, e.g., in the presence of optically (e.g., fluorescently) labeled nucleotides or nucleotide analogs are desirable in such reactions because they can provide more reliable sequencing data and increased read lengths compared to the parental polymerases, e.g., photosensitive polymerases, from which they have been derived. As will be appreciated, the length of contiguous reads of sequence directly impacts the ability to assemble genomic information from segments of sequenced genomic DNA.

Other Applications for Enzymes that Exhibit Increased Photostability

In another embodiment, caspase proteases play an essential role in apoptosis. The caspases convey the apoptotic signal in a proteolytic cascade, with caspases cleaving and activating other caspases that then degrade other cellular targets, e.g., specific structural, regulatory, and DNA repair proteins, that lead to cell death (Lazebnik, et al. (1994) "Cleavage of poly(ADP-ribose) polymerase by a proteinase with properties like ICE." *Nature* 371: 346-347; Casciola-Rosen, et al. (1994) "Specific cleavage of the 70-kDa protein component of the U1 small nuclear ribonucleoprotein is a characteristic biochemical feature of apoptotic cell death." *J Biol Chem* 269: 30757-30760). Caspases or caspase sensors exhibiting improved photostability, e.g., that are generated using the methods provided by the invention, can be useful in increasing the sensitivity and reliability of various caspase activation assays, e.g., wherein the cleavage of the caspase sensor, e.g., a fluorescently labeled substrate, is typically monitored by a change in fluorescence emissions, such as in FRET. In addition, such an improved reagent can be useful in increasing the accuracy of screening for caspase inhibitors, e.g., in drug screens.

Because of the key role that aberrant regulation of protein phosphorylation plays in diseases such as cancer, diabetes and hypertension, kinases and phosphatases are significant targets in screens for drug effects. Fluorescent readout of protein kinase or protein phosphatase activity provides a means by which to identify and characterize inhibitory agents, assess structure-function relationships, and correlate enzyme activity with cellular behavior. Kinases, phosphatases, and/or peptide-based fluorescent kinase sensors or phosphatase sensors with improved photostability can be of beneficial use in FRET analyses to provide more accurate readouts of kinase or phosphatase activity, e.g., because of the reduced probability that the enzyme or sensor will degrade due to light-generated reactive species.

In addition, the accuracy and reliability of results obtained from ligase-mediated mutation detection techniques, e.g., ligase chain reaction (LCR) and/or ligase detection reactions (LDR), can be improved by using ligases that exhibit increased resistance to photodamage. These detection methods can typically include the use of fluorescently labeled oligonucleotide primers, which can reduce the activity of a photosensitive ligase.

Those of skill in the art will appreciate that modifications to the aforementioned enzymes that confer increased photostability most beneficially preserve the enzyme's activity or function of interest.

Modifying DNA Polymerases and Other Enzymes to Improve Photostability

Structure-Based Design of Recombinant Enzymes

Structural data for a polymerase or other enzyme can be used to conveniently identify amino acid residues as candidates for mutagenesis to create recombinant enzymes, e.g., by targeting photosensitive residues such as phenylalanine, tyrosine, tryptophan, histidine, cysteine, or methionine, into less sensitive residues, e.g., any of the other naturally occurring amino acids, or even unnatural amino acids that display reduced photosensitivity.

For example, analysis of the three-dimensional structure of a polymerase such as Φ29 can identify photosensitive residues that are proximal to the active polymerization site of the enzyme, e.g., residues that are within about 20 angstroms of the active site, or within about 20 angstroms of a label moiety when the label is present in the active site (e.g., within about 20 angstroms of a fluorophore moiety on a nucleotide analog). Depending on the application, residues further from the fluorophore moiety, e.g., about 30, about 40, or about 50 angstroms can be modified, as can residues closer to the moiety, e.g., 15 angstroms or less, 10 angstroms or less, or 5 angstroms or less. These include residues at positions position 128, 137, 230, 232, 246, 248, 254, 300, 315, 363, 367, 369, 378, 385, 454, 461, 482, 483, 485, 489, 494, 500, 505, 506, 521, and/or 526, with numbering of positions being relative to a wild-type Φ29 polymerase (e.g., SEQ ID NO: 1).

The three-dimensional structures of a large number of DNA polymerases and other enzymes have been determined by x-ray crystallography and nuclear magnetic resonance (NMR) spectroscopy, including the structures of polymerases with bound templates, nucleotides, and/or nucleotide analogs. Many such structures are freely available for download from the Protein Data Bank, at (www(dot)rcsb (dot)org/pdb. Structures, along with domain and homology information, are also freely available for search and download from the National Center for Biotechnology Information's Molecular Modeling DataBase, at www(dot)ncbi(dot) nlm(dot)nih(dot)gov/Structure/MMDB/mmdb(dot)shtml.

The structures of additional polymerases and other enzymes can be modeled, for example, based on homology of the polymerases or other enzymes with polymerases or other enzymes whose structures have already been determined. Alternatively, the structure of a given polymerase or other enzyme, optionally complexed with reactants or substrates such as a template and/or nucleotide analog, or the like, can be determined. (See FIG. 1 and corresponding description.)

Techniques for crystal structure determination of enzymes are well known. See, for example, McPherson (1999) *Crystallization of Biological Macromolecules* Cold Spring Harbor Laboratory; Bergfors (1999) *Protein Crystallization* International University Line; Mullin (1993) *Crystallization* Butterwoth-Heinemann; Stout and Jensen (1989) *X-ray structure determination: a practical guide,* 2nd Edition Wiley Publishers, New York; Ladd and Palmer (1993) *Structure determination by X-ray crystallography,* 3rd Edition Plenum Press, New York; Blundell and Johnson (1976) *Protein Crystallography* Academic Press, New York; Glusker and Trueblood (1985) *Crystal structure analysis: A primer,* 2nd Ed. Oxford University Press, New York; *International Tables for Crystallography,* Vol. F. *Crystallography of Biological Macromolecules*; McPherson (2002) *Introduction to Macromolecular Crystallography* Wiley-Liss; McRee and David (1999) *Practical Protein Crystallography,* Second Edition Academic Press; Drenth (1999) *Principles of Protein X-Ray Crystallography* (Springer Advanced Texts in Chemistry) Springer-Verlag; Fanchon and Hendrickson (1991) Chapter 15 of *Crystallographic Computing,* Volume 5 IUCr/Oxford University Press; Murthy (1996) Chapter 5 of *Crystallographic Methods and Protocols* Humana Press; Dauter et al. (2000) "Novel approach to phasing proteins: derivatization by short cryo-soaking with halides" *Acta Cryst* D56: 232-237; Dauter (2002) "New approaches to high-throughput phasing" *Curr Opin Structural Biol* 12: 674-678; Chen et al. (1991) "Crystal structure of a bovine neurophysin-II dipeptide complex at 2.8 Å determined from the single-wavelength anomalous scattering signal of an incorporated iodine atom" *Proc Natl Acad Sci USA* 88: 4240-4244; and Gavira et al. (2002) "*Ab initio* crystallographic structure determination of insulin from protein to electron density without crystal handling" *Acta Cryst* D58: 1147-1154.

In addition, a variety of programs to facilitate data collection, phase determination, model building and refinement, and the like are publicly available. Examples include, but are not limited to, the HKL2000 package (Otwinowski and Minor (1997) "Processing of X-ray Diffraction Data Collected in Oscillation Mode" *Methods in Enzymology* 276: 307-326), the CCP4 package (Collaborative Computational Project (1994) "The CCP4 suite: programs for protein crystallography" *Acta Cryst* D50: 760-763), SOLVE and RESOLVE (Terwilliger and Berendzen (1999) *Acta Cryst* D55: 849-861), SHELXS and SHELXD (Schneider and Sheldrick (2002) "Substructure solution with SHELXD" *Acta Cryst* D58: 1772-1779), Refmac5 (Murshudov et al. (1997) "Refinement of Macromolecular Structures by the Maximum-Likelihood Method" *Acta Cryst* D53: 240-255), PRODRG (van Aalten et al. (1996) "PRODRG, a program for generating molecular topologies and unique molecular descriptors from coordinates of small molecules" *J Comput Aided Mol Des* 10: 255-262), and O (Jones et al. (1991) "Improved methods for building protein models in electron density maps and the location of errors in these models" Acta Cryst A47: 110-119).

Techniques for structure determination by NMR spectroscopy are similarly well described in the literature. See, e.g., Cavanagh et al. (1995) *Protein NMR Spectroscopy: Principles and Practice*, Academic Press; Levitt (2001) *Spin Dynamics: Basics of Nuclear Magnetic Resonance*, John Wiley & Sons; Evans (1995) *Biomolecular NMR Spectroscopy*, Oxford University Press; Wüthrich (1986) *NMR of Proteins and Nucleic Acids* (Baker Lecture Series), Kurt Wiley-Interscience; Neuhaus and Williamson (2000) *The Nuclear Overhauser Effect in Structural and Conformational Analysis,* 2nd Edition, Wiley-VCH; Macomber (1998) *A Complete Introduction to Modern NMR Spectroscopy*, Wiley-Interscience; Downing (2004) *Protein NMR Techniques* (Methods in Molecular Biology), 2nd edition, Humana Press; Clore and Gronenborn (1994) *NMR of Proteins* (Topics in Molecular and Structural Biology), CRC Press; Reid (1997) *Protein NMR Techniques*, Humana Press; Krishna and Berliner (2003) *Protein NMR for the Millenium* (Biological Magnetic Resonance), Kluwer Academic Publishers; Kiihne and De Groot (2001) *Perspectives on Solid State NMR in Biology* (Focus on Structural Biology, 1), Kluwer Academic Publishers; Jones et al. (1993) *Spectroscopic Methods and Analyses: NMR, Mass Spectrometry, and Related Techniques* (Methods in Molecular Biology, Vol. 17), Humana Press; Goto and Kay (2000) "New developments in isotope labeling strategies for protein solution NMR spectroscopy." *Curr Opin Struct Biol* 10: 585-592; Gardner and Kay (1998) "The use of $^2$H, $^{13}$C, $^{15}$N multidimensional NMR to study the structure and dynamics of proteins." *Annu Rev Biophys Biomol Struct* 27: 357-406; Wüthrich (2003) "NMR Studies of Structure and Function of Biological Macromolecules (Nobel Lecture)" Angewandte Chemie International Edition *Angew Chem Int Ed* 42: 3340-3363; Bax (1994) "Multidimensional nuclear magnetic resonance methods for protein studies." *Curr Opin Struct Biol* 4: 738-744; Pervushin et al. (1997) "Attenuated T$_2$ relaxation by mutual cancellation of dipole-dipole coupling and chemical shift anisotropy indicates an avenue to NMR structures of very large biological molecules in solution." *Proc Natl Acad Sci USA* 94: 12366-12371; Fiaux et al. (2002) "NMR analysis of a 900K GroEL-GroES complex." *Nature* 418: 207-211; Fernandez and Wider (2003) "TROSY in NMR studies of the structure and function of large biological macromolecules." *Curr Opin Struct Biol* 13: 570-580; Ellman et al. (1992) "Site-specific isotopic labeling of proteins for NMR studies." *J Am Chem Soc* 114: 7959-7961; Wider (2000) "Structure Determination of Biological Macromolecules in Solution Using NMR Spectroscopy." *BioTechniques* 29: 1278-1294; Pellecchia et al. (2002) "NMR in drug discovery." *Nature Rev Drug Discov* 1: 211-219; Arora and Tamm (2001) "Biophysical approaches to membrane protein structure determination." *Curr Opin Struct Biol* 11: 540-547; and Pellecchia et al. (2001) "SEA-TROSY (Solvent Exposed Amides with TROSY): A Method to Resolve the Problem of Spectral Overlap in Very Large Proteins." *J Am Chem Soc* 123: 4633-4634.

The structure of an enzyme, e.g., a DNA polymerase, or an enzyme bound to a substrate or reactant, e.g., a DNA polymerase bound to a DNA and/or with a given nucleotide analog incorporated into the active site can, as noted, be directly determined, e.g., by x-ray crystallography or NMR spectroscopy, or the structure can be modeled based on the structure of the polymerase and/or a structure of a polymerase with a natural nucleotide or other relevant substrate/reactant bound. (See FIG. 1 and corresponding description.) The active site or other relevant domain of the enzyme can be identified, for example, by homology with other enzymes, e.g., other polymerases, examination of enzyme-substrate or enzyme-reactant co-complexes (e.g., polymerase-template or polymerase-nucleotide), biochemical analysis of mutant enzymes such as polymerases, and/or the like. The position of a labeled substrate/reactant (e.g., nucleotide analog), as opposed to an available structure for a natural substrate or reactant (e.g., natural nucleotide structure) in the active site can be modeled, for example, by projecting the location of non-natural features of the substrate or reactant (e.g., analog, e.g., additional phosphate or phosphonate groups in the phosphorus containing chain linked to the nucleotide, e.g., tetra, penta, hexa, or hepta phosphate groups, detectable labeling groups, e.g., fluorescent dyes, or the like) based on the previously determined location of, e.g., another reactant (e.g., nucleotide or nucleotide analog) in the active site.

Such modeling of the reactant or substrate (e.g., nucleotide analog or template or both) in the active site can involve simple visual inspection of a model of the enzyme (e.g., polymerase), for example, using molecular graphics software such as the PyMOL viewer (open source, freely available on the World Wide Web at www(dot)pymol(dot) org) or Insight II (commercially available from Accelrys at (www (dot) accelrys (dot) com/products/insight). Alternatively, modeling of the active site complex of the polymerase or a putative mutant polymerase, for example, can involve computer-assisted docking, molecular dynamics, free energy minimization, and/or like calculations. Such modeling techniques have been well described in the literature; see, e.g., Babine and Abdel-Meguid (eds.) (2004) *Protein Crystallography in Drug Design*, Wiley-VCH, Weinheim; Lyne (2002) "Structure-based virtual screening: An overview" *Drug Discov Today* 7: 1047-1055; Molecular Modeling for Beginners, at (www (dot) usm (dot) maine (dot) edu/~rhodes/SPVTut/index (dot) html; and Methods for Protein Simulations and Drug Design at (www (dot) dddc (dot) ac (dot) cn/embo04; and references therein. Software to facilitate such modeling is widely available, for example, the CHARMm simulation package, available academically from Harvard University or commercially from Accelrys (at www (dot) accelrys (dot) com), the Discover simulation package (included in Insight II, supra), and Dynama (available at (www(dot) cs (dot) gsu (dot) edu/~cscrwh/progs/progs (dot) html). See also an extensive list of modeling software at (www (dot) netsci (dot) org/Resources/Software/Modeling/MMMD/top (dot) html.

Visual inspection and/or computational analysis of a polymerase, e.g., complexed with a fluorescently-labeled or fluorescent nucleotide or nucleotide analog, or other enzyme model, e.g., complexed with a fluorescent or fluorescently labeled substrate or product, can identify relevant photodamage susceptibility features of the active site or other proximal domain, including, for example, photodamage sensitive amino acid residues in close proximity, e.g., about 15-30 Å, to a labeled reactant, labeled substrate, or labeled product. A residue can, for example, be deleted or replaced with a residue having a non-sensitive side chain.

For example, a model of an enzyme and a substrate or product comprising a photosensitizer can be examined to identify residues for mutation, e.g., within a selected distance between, e.g., the photosensitizer and susceptible residues in the active site of an enzyme of interest, e.g., a nucleotide binding pocket of a DNA polymerase, or between e.g., the photosensitizer and susceptible residues on the surface of an enzyme of interest. (See FIG. 1 and corresponding description.) Nevertheless, amino acids that are most beneficially replaced by residues less susceptible to photodamage need not be limited to either of these areas in an enzyme of interest. One, some, or all such residues identified can then be replaced with residues less susceptible to photodamage.

Residues identified as targets for replacement can be substituted with other residues chosen, e.g., using structure/function modeling. See, e.g., Hayes, et al. (2002) "Combining computational and experimental screening for rapid optimization of protein properties." *Proc Natl Acad Sci, USA* 99: 15926-15931. Similarly, substitutions can also be planned via, e.g., energy minimization modeling, e.g. using techniques such as steepest descent and/or conjugate gradient. Rotamer modeling using available libraries and databases (see, e.g., Jones, et al. (1991) "Improved methods for building protein models in electron density maps and the location of errors in these models." *Acta Cryst A* 47: 110-119; Ponder and Richards "Tertiary templates for proteins. Use of packing criteria in the enumeration of allowed sequences for different structural classes." (1987). *J Mol Biol* 193: 775-791; and Dunbrack (2002) "Rotamer libraries in the 21st century." *Curr Opin Struct Biol* 12: 431-40) can also be useful in modeling the structure of an enzyme by determining preferred combinations of amino acid side-chain torsion angles, which can assist in the identification of suitable substitutions. Homology modeling can also be employed, or substitutions can be made based on conservative, best substitution tables known in the art; see, e.g., Bordo, et al., (1991) "Suggestions for "Safe" Residue Substitutions in Site-Directed Mutagenesis." *J Mol Biol* 217: 721-729 and the section entitled "Conservative variations" hereinbelow. Any one or combination of these modeling strategies can be used alone or with the other methods described above to generate one or more mutants or a library of mutants, each comprising one or more desired substitutions, which can then be assayed for photostability relative to a parental polymerase, as described elsewhere herein.

As just one specific example of such structure-based design, inspection of a model of the Φ29 polymerase reveals that the exonuclease domain optimally binds two divalent cations. This domain can be altered, e.g., made larger, to accommodate a larger, trivalent lanthanide ion, e.g., $Eu^{3+}$ or $Tb^{3+}$. Additional mutations can be made to reposition the amino acid residues that coordinate with the divalent ions.

In another example, analysis of the three-dimensional structure of a polymerase such as Φ29 can identify photosensitive residues that are proximal to the active polymerization site of the enzyme, e.g., residues that are within about 20 angstroms of the active site, or within about 20 angstroms of a label moiety when the label is present in the active site (e.g., within about 20 angstroms of a fluorophore moiety on a nucleotide analog). Depending on the application, residues further from the fluorophore moiety, e.g., about 30, about 40, or about 50 angstroms can be modified, as can residues closer to the moiety, e.g., 15 angstroms or less, 10 angstroms or less, or 5 angstroms or less. These include, but are not limited to, residues at positions 128, 137, 230, 232, 246, 248, 254, 300, 315, 363, 367, 369, 378, 385, 454, 461, 482, 483, 485, 489, 494, 500, 505, 506, 521, and/or 526, with numbering being relative to a wild-type Φ29 polymerase. (See FIG. 1 and corresponding description.)

Relative to a wild-type Φ29 DNA polymerase, modifications to photosensitive residues can include any one or any combination of two or more substitutions (e.g., 2-10 substitutions, or more than 10 substitutions) including: an amino acid substitution at position 128, 137, 230, 232, 246, 248, 254, 300, 315, 363, 367, 369, 378, 385, 454, 461, 482, 483, 485, 489, 494, 500, 505, 506, 521, and/or 526, optionally other than Y369R, Y369H, or Y369E. Example substitutions to increase a polymerase's resistance to photodamage, include but are not limited to: M246L, F248L, W367S, Y369V, Y482V, W483S, W483F, W483L, W483V, W483I, W483P, W483Q, H485G, H485N, H485K, H485R, H485A, H485E, H485S, H485I, H485P, H485Q, H485T, H485F, H485G, H485L, Y505V, M506L, Y521V, F526L, M246L and F248L, W367S and Y369V, Y482V and W483S, Y482V and H485G, W483S and H485G, Y505V and M506L, and Y521V and F526L. (See Tables 1 and 2.) Additional conservative substitutions can also be made. Optionally, any amino acid, e.g., natural, unnatural, or rare amino acid that is not chromophoric and/or that does not contain a sulfur moiety can be substituted at amino acid position 485, e.g., wherein the numbering of positions is relative to a wild-type Φ29 polymerase (e.g., SEQ ID NO: 1). Useful libraries of double substitution mutants and triple substitution mutants are provided in Tables 3 and 4 hereinbelow. In addition to the above mutations, preferred polymerases can also comprise the following mutations: N62D, T368F, E375Y, and/or K512K. Particular preferred embodiments include all four of these mutations in addition to the pairs of mutations listed in Table 6, e.g., wherein the numbering of positions is relative to a wild-type Φ29 polymerase, e.g., SEQ ID NO: 1.

Thus, in addition to methods of using the polymerases and other compositions herein, the present invention also includes methods of making the polymerases. As described, methods of making a recombinant DNA polymerase can include structurally modeling a first polymerase, e.g., using any available crystal structure and molecular modeling software or system. Based on the modeling, one or more feature affecting photostability near or within the active site region is identified, e.g., a photosensitive amino acid such as phenylalanine, tyrosine, tryptophan, histidine, cysteine, or methionine. These residues can be, e.g., in the active site, or a proximal domain or interdomain region. The DNA polymerase is mutated to include photostable residues, e.g., a non-oxidizable and/or non-chromophoric rare amino acid, a non-oxidizable and/or non-chromophoric unnatural amino acid, or any natural amino acid that is not tryptophan, histidine, methionine, cysteine, tyrosine, or phenylalanine, at such positions, and then screened for an activity of interest.

Mutating Enzymes

Various types of mutagenesis are optionally used in the present invention, e.g., to modify enzymes such as polymerases to produce enzyme variants, e.g., in accordance with structural models and model predictions as discussed above, or by using random or semi-random mutational approaches. In general, any available mutagenesis procedure can be used for making polymerase or other enzyme mutants. Such mutagenesis procedures optionally include selection of mutant nucleic acids and polypeptides for one or more activity of interest, e.g., during exposure to light, to assess photostability of the enzyme. Procedures that can be used include, but are not limited to: site-directed point mutagenesis, random point mutagenesis, in vitro or in vivo homologous recombination (DNA shuffling and combinatorial overlap PCR), mutagenesis using uracil containing templates, oligonucleotide-directed mutagenesis, phosphorothioate-modified DNA mutagenesis, mutagenesis using gapped duplex DNA, point mismatch repair, mutagenesis using repair-deficient host strains, restriction-selection and restriction-purification, deletion mutagenesis, mutagenesis by total gene synthesis, degenerate PCR, double-strand break repair, and many others known to persons of skill. The starting polymerase for mutation can be any of those noted herein, including available polymerase mutants such as those identified e.g., in WO 2007/076057 POLYMERASES FOR NUCLEOTIDE ANALOG INCORPORATION by Hanzel et al.; PCT/US2007/022459 POLYMERASE ENZYMES AND REAGENTS FOR ENHANCED NUCLEIC ACID SEQUENCING; Hanzel et al. WO 2007/075987 ACTIVE SURFACE COUPLED POLYMERASES; and Hanzel et al. WO 2007/076057.

Optionally, mutagenesis can be guided by known information from a naturally occurring polymerase molecule, or of a known altered or mutated polymerase (e.g., using an existing mutant polymerase as noted in the preceding references), e.g., sequence, sequence comparisons, physical properties, crystal structure and/or the like as discussed above. However, in another class of embodiments, modification can be semi-random (e.g., as in classical or "family" DNA shuffling, see, e.g., Crameri et al. (1998) "DNA shuffling of a family of genes from diverse species accelerates directed evolution" *Nature* 391: 288-291).

In addition to being well known to those of skill in the art, information on mutation formats is found in: Sambrook et al., *Molecular Cloning-A Laboratory Manual* (3rd Ed.), Vol. 1-3, Cold Spring Harbor Laboratory, Cold Spring Harbor, N.Y., 2000 ("Sambrook"); *Current Protocols in Molecular Biology*, F. M. Ausubel et al., eds., Current Protocols, a joint venture between Greene Publishing Associates, Inc. and John Wiley & Sons, Inc., (supplemented through 2008) ("Ausubel")); and *PCR Protocols A Guide to Methods and Applications* (Innis et al. eds) Academic Press Inc. San Diego, Calif. (1990) (Innis). The following publications and references cited within provide additional detail on mutation formats: Arnold (1993) "*Protein engineering for unusual environments.*" *Current Opinion in Biotechnology* 4: 450-455; Bass et al. (1988) "*Mutant Trp repressors with new DNA-binding specificities.*" *Science* 242: 240-245; Bordo and Argos (1991) "Suggestions for 'safe' Residue Substitutions in Site-directed Mutagenesis." *J Mol Biol* 217: 721-729; Botstein & Shortie (1985) "Strategies and applications of in vitro mutagenesis." *Science* 229: 1193-1201; Carter et al. (1985) "*Improved oligonucleotide site-directed mutagenesis using M13 vectors.*" *Nucl Acids Res* 13: 4431-4443; Carter (1986) "*Site-directed mutagenesis.*" *Biochem J* 237: 1-7; Carter (1987) "Improved oligonucleotide-directed mutagenesis using M13 vectors." *Methods in Enzymol* 154: 382-403; Dale et al. (1996) "Oligonucleotide-directed random mutagenesis using the phosphorothioate method." *Methods Mol Biol* 57: 369-374; Eghtedarzadeh and Henikoff (1986) "Use of oligonucleotides to generate large deletions." *Nucl Acids Res* 14: 5115; Fritz et al. (1988) "Oligonucleotide-directed construction of mutations: a gapped duplex DNA procedure without enzymatic reactions in vitro." *Nucl Acids Res* 16: 6987-6999; Grundström et al. (1985) "Oligonucleotide-directed mutagenesis by microscale 'shot-gun' gene synthesis." *Nucl Acids Res* 13: 3305-3316; Hayes (2002) "Combining Computational and Experimental Screening for rapid Optimization of Protein Properties." *Proc Natl Acad Sci USA* 99: 15926-15931; Kunkel, "The efficiency of oligonucleotide directed mutagenesis." in Nucleic Acids & Molecular Biology (Eckstein, F. and Lilley, D. M. J. eds., Springer Verlag, Berlin)) (1987); Kunkel (1985) "Rapid and efficient site-specific mutagenesis without phenotypic selection." *Proc Natl Acad Sci USA* 82: 488-492; Kunkel et al. (1987) "Rapid and efficient site-specific mutagenesis without phenotypic selection." *Methods in Enzymol* 154: 367-382; Kramer et al. (1984) "*The gapped duplex DNA approach to oligonucleotide-directed mutation construction.*" *Nucl Acids Res* 12: 9441-9456; Kramer & Fritz (1987) "Oligonucleotide-directed construction of mutations via gapped duplex DNA." Methods in Enzymol 154: 350-367; Kramer et al. (1984) "Point Mismatch Repair." *Cell* 38: 879-887; Kramer et al., (1988) "Improved enzymatic in vitro reactions in the gapped duplex DNA approach to oligonucleotide-directed construction of mutations." *Nucl Acids Res* 16: 7207; Ling et al. (1997) "Approaches to DNA mutagenesis: an overview." *Anal Biochem* 254: 157-178; Lorimer and Pastan (1995) "Random recombination of antibody single chain Fv sequences after fragmentation with DNaseI in the presence of $Mn^{2+}$." *Nucl Acids Res* 23: 3067-3068; Mandecki (1986) "Oligonucleotide-directed double-strand break repair in plasmids of *Escherichia coli*: a method for site-specific mutagenesis." *Proc Natl Acad Sci USA* 83: 7177-7181; Nakamaye & Eckstein (1986) "Inhibition of restriction endonuclease NciI cleavage by phosphorothioate groups and its application to oligonucleotide-directed mutagenesis." *Nucl Acids Res* 14: 9679-9698; Nambiar et al., (1984) "Total synthesis and cloning of a gene coding for the ribonuclease S protein." *Science* 223: 1299-1301; Sakamar and Khorana (1988) "Total synthesis and expression of a gene for the a-subunit of bovine rod outer segment guanine nucleotide-binding protein (transducin)." *Nucl Acids Res* 14: 6361-6372; Sayers et al. (1988) "Y-T Exonucleases in phosphorothioate-based oligonucleotide-directed mutagenesis." *Nucl Acids Res* 16: 791-802; Sayers et al. (1988) "Strand specific cleavage of phosphorothioate-containing DNA by reaction with restriction endonucleases in the presence of ethidium bromide." *Nucl Acids Res* 16: 803-814; Sieber, et al. (2001) "Libraries of hybrid proteins from distantly related sequences." *Nature Biotechnology* 19: 456-460; Smith (1985) "In vitro mutagenesis." *Ann Rev Genet* 19: 423-462; Zoller and Smith (1983) "Oligonucleotide-directed mutagenesis of DNA fragments cloned into M13 vectors." *Methods in Enzymol* 100: 468-500; Zoller and Smith (1987) "Oligonucleotide-directed mutagenesis: A simple method using two oligonucleotide primers and a single-stranded DNA template." *Methods in Enzymol* 154: 329-350; Stemmer (1994) "Rapid evolution of a protein in vitro by DNA shuffling." *Nature* 370: 389-91; Taylor et al. (1985) "The use of phosphorothioate-modified DNA in restriction enzyme reactions to prepare nicked DNA." *Nucl Acids Res* 13: 8749-8764; Taylor et al. (1985) "The rapid generation of oligonucleotide-directed mutations at high frequency using phosphorothioate-modified DNA." *Nucl Acids Res* 13: 8765-8787; Wells et al. (1986) "Importance of hydrogen-bond formation in stabilizing the transition state of subtilisin." *Phil Trans R Soc Lond A* 317: 415-423; Wells et al. (1985) "Cassette mutagenesis: an efficient method for generation of multiple mutations at defined sites." *Gene* 34: 315-323; Zoller and Smith (1982) "Oligonucleotide-directed mutagenesis using M13-derived vectors: an efficient and general procedure for the production of point mutations in any DNA fragment." *Nucl Acids Res* 10: 6487-6500; Clackson et al. (1991) "Making antibody fragments using phage display libraries." *Nature* 352: 624-628; Gibbs et al. (2001) "Degenerate oligonucleotide gene shuffling (DOGS): a method for enhancing the frequency of recombination with family shuffling," *Gene* 271: 13-20; and Hiraga and Arnold (2003) "General method for sequence-independent site-directed chimeragenesis." *J Mol Biol* 330: 287-296. Additional details on many of the above methods can be found in *Methods in Enzymology* Volume 154, which also describes useful controls for trouble-shooting problems with various mutagenesis methods.

Screening Kinetic Parameters

The polymerases or other enzymes of the invention, e.g., which can include one or more mutations and/or triplet quencher for improved photostability, can be screened or otherwise tested to determine whether the enzyme is active, e.g., following exposure to light in the presence of a fluorophore (e.g., a labeled substrate or reactant), and/or how active the polymerase is following exposure to a photosensitizer for a given length of time. These metrics can be compared to the activity of the enzyme when not exposed to light energy and/or to control enzymes that are similar to the mutant enzyme, except lacking the mutation being screened. For example, $k_{cat}$, $K_m$, $V_{max}$, $k_{cat}/K_m$, $V_{max}/K_m$, $k_{pol}$, and/or $K_d$ of the mutant enzyme (e.g., recombinant modified or engineered DNA polymerase) for the reactant or substrate (e.g., nucleotide (or nucleotide analog) or template nucleic acid) can be determined. The enzyme perfection metric $k_{cat}/K_m$ is also a useful measure, e.g., for assessing activity. $k_{cat}/K_m$ is a measure of substrate binding that leads to product formation.

As is well known in the art, for enzymes obeying simple Michaelis-Menten kinetics, kinetic parameters are readily derived from rates of catalysis measured at different substrate/reactant concentrations. The Michaelis-Menten equation, $V=V_{max}[S](N+K_m)^{-1}$, relates the concentration of uncombined substrate ([S], approximated by the total substrate concentration), the maximal rate ($V_{max}$, attained when the enzyme is saturated with substrate), and the Michaelis constant ($K_m$, equal to the substrate concentration at which the reaction rate is half of its maximal value), to the reaction rate (V). In general, the dissociation rate can be measured in any manner that detects the enzyme/substrate (e.g., polymerase/DNA) complex over time. This includes stopped flow spectroscopy, or even simply by taking aliquots over time and testing for enzyme (e.g., polymerase) activity on the substrate (e.g., DNA) of interest. Free enzyme can be captured with an enzyme trap after dissociation, e.g., by incubation in the presence of a competitive binder (e.g., heparin or an excess of competitor DNA for a polymerase).

For many enzymes, $K_m$ is equal to the dissociation constant of the enzyme-substrate complex and is thus a measure of the strength of the enzyme-substrate complex. For such an enzyme, in a comparison of $K_m$s, a lower $K_m$ represents a complex with stronger binding, while a higher Km represents a complex with weaker binding. The ratio $k_{cat}/K_m$, sometimes called the specificity constant, represents the apparent rate constant for combination of substrate with free enzyme. The larger the specificity constant, the more efficient the enzyme is in binding the substrate and converting it to product.

$k_{cat}$ (also called the turnover number of the enzyme) can be determined if the total enzyme concentration ($[E_T]$, i.e., the concentration of active sites) is known, since $V_{max}=k_{cat}[E_T]$. For situations in which the total enzyme concentration is difficult to measure, the ratio $V_{max}/K_m$ is often used instead as a measure of efficiency. $K_m$ and $V_{max}$ can be determined, for example, from a Lineweaver-Burk plot of 1/V against 1/[S], where the y intercept represents $1/V_{max}$, the x intercept $-1/K_m$, and the slope $K_m/V_{max}$, or from an Eadie-Hofstee plot of V against V/[S], where the y intercept represents $V_{max}$, the x intercept $V_{max}/K_m$, and the slope $-K_m$. Software packages such as KinetAsyst™ or Enzfit (Biosoft, Cambridge, UK) can facilitate the determination of kinetic parameters from catalytic rate data.

For enzymes such as polymerases that have multiple substrates, varying the concentration of only one substrate while holding the others in suitable excess (e.g., effectively constant) concentration typically yields normal Michaelis-Menten kinetics. Useful polymerases modified according to the methods provided by the invention can exhibit a $k_{pol}$ that is, e.g., at least 1% or higher of the $k_{pol}$ of the parental polymerases from which they are derived, the same as the $k_{pol}$ of the parental polymerases from which they are derived or, preferably, better than the $k_{pol}$ of the parental polymerases from which they are derived.

In one embodiment, using pre-steady-state kinetics, the nucleotide concentration dependence of the rate $k_{obs}$ (the observed first-order rate constant for dNTP incorporation) provides an estimate of the $K_m$ for a ground state binding and the maximum rate of polymerization ($k_{pol}$). The $k_{obs}$ is measured using a burst assay. The results of the assay are fitted with the Burst equation; Product=A[1−exp(−$k_{obs}$*t)]+$k_{ss}$*t where A represents amplitude an estimate of the concentration of the enzyme active site*s, $k_{ss}$ is the observed steady-state rate constant and t is the reaction incubation time. The $K_m$ for dNTP binding to the polymerase-DNA complex and the $k_{pol}$ are calculated by fitting the dNTP concentration dependent change in the $k_{obs}$ using the equation $k_{obs}=(k_{pol}*[S])*(K_m+[S])-1$ where [S] is the substrate concentration. Results are optionally obtained from a rapid-quench experiment (also called a quench-flow measurement), for example, based on the methods described in Johnson (1986) "Rapid kinetic analysis of mechanochemical adenosinetriphosphatases" *Methods Enzymol* 134: 677-705; Patel et al. (1991) "Pre-steady-state kinetic analysis of processive DNA replication including complete characterization of an exonuclease-deficient mutant" *Biochemistry* 30: 511-25; and Tsai and Johnson (2006) "A new paradigm for DNA polymerase specificity" *Biochemistry* 45: 9675-87.

For a more thorough discussion of enzyme kinetics, see, e.g., Berg, Tymoczko, and Stryer (2002) *Biochemistry*, Fifth Edition, W. H. Freeman; Creighton (1984) *Proteins: Structures and Molecular Principles*, W. H. Freeman; and Fersht (1985) *Enzyme Structure and Mechanism, Second Edition*, W. H. Freeman.

Optionally, the polymerase also exhibits a $K_m$ for a labeled nucleotide analog that is less than a $K_m$ observed for a wild-type polymerase, to facilitate applications in which the polymerase incorporates the analog, e.g., during SMS. For example, the modified recombinant polymerase can exhibit a $K_m$ for the phosphate-labeled nucleotide analog that is less than less than 75%, 50%, 25% or less than that of wild-type or parental polymerase such as a wild type Φ29). In one specific class of examples, the polymerases of the invention have a $K_m$ of about 10 μM or less for a non-natural nucleotide analog such as a phosphate labeled analog. For information regarding appropriate polymerases that display increased nucleotide analog activity, see, e.g., WO 2007/076057 POLYMERASES FOR NUCLEOTIDE ANALOG INCORPORATION by Hanzel et al., and PCT/US2007/022459 POLYMERASE ENZYMES AND REAGENTS FOR ENHANCED NUCLEIC ACID SEQUENCING by Rank et al.

In one aspect, the improved activity of the enzymes of the invention is measured with reference to a model analog or analog set and compared with a given parental enzyme. For example, in the case of enzymes derived from a Φ29 parental enzyme, where the improvement being sought is an increase in photostability, an improved enzyme of the invention would have a decreased rate of activity loss over time in the presence of a fluorophore being exposed to light than the parental enzyme, e.g., a wild type Φ29. While the foregoing may be used as a characterization tool, it in no way is intended as a specifically limiting reaction of the invention.

In particular, the improved photostability of the enzymes of the invention can be measured by monitoring and comparing modified recombinant polymerases' activity half-lives ($T_{enz}/2$) to the activity half-lives of the parental polymerases from which they are derived (See a.) In general, enzymes, e.g., DNA polymerases, will exhibit an activity half-life in a given environment. Enzyme's activities decrease over time due to, e.g., proteolytic degradation, mechanical damage, oxidation, heat damage, changes in pH, and the like. Accordingly, exposure to, e.g., highly reactive singlet oxygen species that can be produced by excitation of an optical label, can increase the rate of overall enzymatic degradation in a particular system or reaction mixture further still. Consequently, the length of time during which, e.g., a DNA polymerase can accurately and reliably replicate a nucleic acid in a template-dependent manner, is shortened, thus shortening sequence read lengths. As will be appreciated, the length of a sequence read directly impacts the ability to assemble genomic information from segments of sequenced genomic DNA, e.g., shorter sequence reads less likely to overlap, and can thus complicate the alignment of multiple sequence reads in efforts to produce, e.g., the contiguous sequence of a genomic DNA.

The photostability of an enzyme, e.g., that had been modified according to the methods of the invention, can be measured by determining the ratio of a modified enzyme's activity after exposure to a known amount optical energy to the parental enzyme's activity after exposure to the same amount of optical energy, wherein the activity readout is the ordinary readout of the reaction in which the enzyme is being used, e.g., a sequencing reaction, a kinase reaction, a ligation reaction, and the like. For example, for a DNA polymerase, the activity readout can comprise the synthesis of a DNA. This ratio is dependent not only on the nature of the modifications or mutations in the more enzyme, but it can also vary with, e.g., the kind of enzyme assayed, the particular fluorophore in the reaction mixture, the wavelength of light the fluorophore emits, the wavelength of light emitted by the excitation radiation source, etc.

The half-life of an enzyme (or $T_{enz}/2$), e.g., modified according to the methods of the invention, that has been exposed to a known amount of optical energy is, desirably, up to 25% longer, up to 50% longer, up to 100% longer, or, most preferably, more than 100% longer than the $T_{enz}/2$ of the parental enzyme lacking the photodamage-protective modifications, e.g., after exposure of the parental enzyme to the same amount of optical energy. For example, a DNA polymerase produced by the methods can exhibit a half-life, e.g., in the presence of a photosensitizer, that is increased by, e.g., tens of seconds, to, e.g., tens of minutes, or more than tens of minutes, relative to the parental polymerase from which it was derived.

Improvements to the photostability of modified polymerases, e.g., derived from a wild type Φ29 polymerase, can be measured by comparing the accuracy of the sequence produced by the modified and the parental polymerases during a sequencing reaction performed with a particular set of fluorescent or fluorescently-labeled nucleotides or nucleotide analogs. Alternately, improvements in photostability can be measured by comparing the read lengths, e.g., the lengths of contiguous sequences produced in sequencing reactions, generated by modified and the parental polymerases during a given length of time or by comparing the total amount of product, e.g., replicated DNA, that modified and parental enzymes can produce during the sequencing reaction described above before the enzymes no longer exhibit activity. The modified polymerases of the invention can exhibit improvements in any one or combination of the aforementioned phenotypes. Additional parameters for which modified polymerases, e.g., produced by the methods of the invention, can optionally be screened are described in, e.g., U.S. patent application Ser. No. 12/315,844, filed Dec. 5, 2008, entitled, "SCREENING ASSAYS FOR POLYMERASE ENHANCEMENT," by Clark, Rey, Christians, and Korlach, the contents of which are incorporated herein by reference in their entirety for all purposes.

It has been observed that longer read lengths are generated in sequencing reactions performed under anaerobic conditions. Optionally, any of the aforementioned parameters can be assayed in the absence of $O_2$. Further details regarding methods for the maintenance of anaerobic conditions in, e.g., a DNA polymerization reaction, are described in, e.g., U.S. Provisional Patent Application No. 61/127,438, entitled "METHODS AND SYSTEMS FOR MITIGATING OXYGEN ENHANCED DAMAGE IN REAL-TIME ANALYTICAL OPERATIONS," by Dixon, et al., filed May 13, 2008.

Screening Enzymes

Screening or other protocols can be used to determine whether an enzyme comprising putative photostability features (e.g., mutant photostable residues, or enzyme-linked triplet state quenchers) displays modified photostability as compared to a homologous enzyme lacking the features. For example, $k_{off}$, $k_{cat}$, $K_m$, $V_{max}$, or $k_{cat}/K_m$ of a recombinant DNA polymerase for a template or nucleotide or analog can be determined as discussed above. Additionally, polymerases modified according to the methods of the invention can optionally be screened for improved features for use in single molecule sequencing. Methods of identifying polymerases with such improved features are described in further detail in, e.g., U.S. patent application Ser. No. 12/315,844, filed Dec. 5, 2008, entitled, "Screening Assays for Polymerase Enhancement," by Clark, Rey, Christians, and Korlach, previously incorporated herein by reference in its for all purposes.

In one desirable aspect, a library of recombinant enzyme variants, such as DNA polymerase variants, can be made and screened for specific properties, e.g., improved photostability. For example, a plurality of members in the library can be made to include one or more mutation that can improve photostability. The library members can be screened for increased tolerance to optical energy, and those that exhibit such a phenotype that can then be screened for other properties of interest (e.g., polymerization, kinase activity, or the like). In general, the library can be screened to identify at least one member comprising a modified activity of interest.

Libraries of polymerases can be either physical or logical in nature, e.g., they can be arrayed in a spatial or logical format. Moreover, any of a wide variety of library formats can be used. For example, polymerases or other enzymes can be fixed to solid surfaces in arrays of proteins. Similarly, liquid phase arrays of enzymes (e.g., in microwell plates) can be constructed for convenient high-throughput fluid manipulations of solutions comprising enzymes. Liquid, emulsion, or gel-phase libraries of cells that express recombinant enzymes can also be constructed, e.g., in microwell plates, or on agar plates. Phage display libraries of enzymes or enzyme domains (e.g., including an active site domain) can be produced. Instructions in making and using libraries can be found, e.g., in Sambrook, Ausubel and Berger, referenced herein.

For the generation of libraries involving fluid transfer to or from microtiter plates, a fluid handling station is optionally used. Several "off the shelf" fluid handling stations for performing such transfers are commercially available, including e.g., the Zymate systems from Caliper Life Sciences (Hopkinton, Mass.) and other stations which utilize automatic pipettors, e.g., in conjunction with the robotics for plate movement (e.g., the ORCA® robot, which is used in a variety of laboratory systems available, e.g., from Beckman Coulter, Inc. (Fullerton, Calif.).

In an alternate embodiment, fluid handling is performed in microchips, e.g., involving transfer of materials from microwell plates or other wells through microchannels on the chips to destination sites (microchannel regions, wells, chambers or the like). Commercially available microfluidic systems include those from Hewlett-Packard/Agilent Technologies (e.g., the HP2100 bioanalyzer) and the Caliper High Throughput Screening System. The Caliper High Throughput Screening System provides one example interface between standard microwell library formats and Labchip technologies. RainDance Technologies' nanodroplet platform provides another method for handling large numbers of spatially separated reactions. Furthermore, the patent and technical literature includes many examples of microfluidic systems that can interface directly with microwell plates for fluid handling.

Because longer read lengths are produced in sequencing reactions performed under anaerobic conditions, screens for polymerases that exhibit increased resistance to photodamage can optionally be performed in the absence of $O_2$. Further details regarding methods for the maintenance of anaerobic conditions in, e.g., a DNA polymerization reaction are described in, e.g., U.S. Provisional Patent Application No. 61/127,438, entitled "METHODS AND SYSTEMS FOR MITIGATING OXYGEN ENHANCED DAMAGE IN REAL-TIME ANALYTICAL OPERATIONS", by Dixon, et al., filed May 13, 2008.

Desirable Properties

The enzymes of the invention can include any of a variety of modifications, e.g., substitution mutations and/or modified domains, that increase their resistance to oxidative damage and/or photodamage in the presence of, e.g., fluorescent labels or other high quantum yield light sources, depending on the application. In a preferred embodiment, the invention provides photostable DNA polymerases, e.g., modified Φ29 DNA polymerases, that exhibit increased resistance to, e.g., light reactive species that are produced by fluorescent or fluorescently-labeled nucleotides or nucleotide analogs in a sequencing reaction mixture.

Increased photostability can be measured assessing a number of kinetic parameters. For example, $k_{cat}$, $K_m$, $V_{max}$, $K_{cat}/K_m$, $V_{max}/K_m$, $K_{pol}$, or $K_d$ of the modified polymerase for the nucleotide (or nucleotide analog), or template nucleic acid can be measured to in the presence of optical energy and compared to the measurements of the same kinetic parameters of the parental enzyme in the presence of the same, e.g., fluorophore. When measured over time, such kinetic metrics can show that the modified polymerase is more stable in the presence of a high quantum yield light source.

The improved photostability of the enzymes of the invention can also be measured by monitoring and comparing enzymes' activity half-lives ($T_{enz}/2$). Enzyme mutants with improved photostability can exhibit a decrease in the reduction of ($T_{enz})/2$ in the presence of, e.g., light generated reactive species. This can be measured by the ratio of a modified enzyme's half life in the presence of a given excitation radiation source to the parental enzyme's half life in the same environment, wherein the readout is the ordinary readout of the reaction, as described above. This ratio is dependent not only on the nature of the modifications or mutations in the more photostable enzyme, but it can also vary with, e.g., the kind of enzyme assayed, the particular fluorophore in the reaction mixture, the wavelength of light the fluorophore emits, the wavelength of light emitted by the excitation radiation source, etc. Desirably, the decrease in the reduction of ($T_{enz})/2$ for a given enzyme in the presence of a photosensitizer is up to 25% or more, up to 50% more, or, more preferably, up to 100% or more. A polymerase produced by the methods can exhibit a half-life, e.g., in the presence of a photosensitizer, that is increased by, e.g., tens of seconds, to, e.g., tens of minutes, relative to the parental polymerase from which it was derived.

For example, in the case of modified polymerases, e.g., derived from a wild type Φ29 polymerase, improvements in photostability can be measured by comparing the accuracy of the sequence produced by the modified and the parental polymerases during a sequencing reaction performed with a particular repertoire of fluorescent (or fluorescently-labeled) nucleotides or nucleotide analogs. Alternately, improvements in photostability can be measured by comparing the read lengths generated by modified and the parental polymerases during a given length of time or by comparing the total amount of product, e.g., replicated DNA, that modified and parental enzymes can produce during the sequencing reaction described above before the polymerases no longer exhibit activity.

Additional Example Details

A number of specific examples of modified polymerases are described herein. The fluorescent nucleotide analog A488dA4P modeled within the polymerase active site of a Φ29 polymerase is shown in FIG. 1A. FIGS. 1B and 1C show a crystal structure of a wild type Φ29 polymerase complexed with the nucleotide analog A555dG6P viewed from different angles. The amino acids in the active site of the polymerase that are within a 20 Å radius of the fluorophore A555 are labeled. The amino acids in the active site of the polymerase that are within a 20 Å radius of the fluorophore are labeled. FIG. 1D shows a crystal structure of a Φ29 polymerase mutant comprising the substitution mutations D12A, D66A, T386F, E375Y, K512Y complexed with the nucleotide analog A555dG6P. The amino acids in the active site of the polymerase mutant that are within a 20 Å radius of the fluorophore are indicated in the figure. Additional parental enzymes of interest comprise the following four mutations: N62D, T368F, E375Y, K512Y, e.g., wherein the numbering of positions is relative to wild-type Φ29 polymerase (e.g., SEQ ID NO: 1). The parental enzymes are then modified specifically for photodamage resistance as described herein.

A list of useful Φ29 mutants, e.g., in which one or more photosensitive amino acid residues within 20 Å of the fluorescent label have been replaced with residues less susceptible to photodamage, is provided in Tables 1 and 2 below.

TABLE 1

USEFUL SINGLE AMINO ACID SUBSTITUTION MUTATIONS*

| Amino Acid Position | From | To |
|---|---|---|
| 246 | Met | Leu |
| 248 | Phe | Leu |
| 367 | Trp | Ser |
| 369 | Tyr | Val |
| 482 | Tyr | Val |
| 483 | Trp | Ser, Phe, Leu, Val, Ile, Pro, or Gln |
| 485 | His | Gly, Asn, Lys, Arg, Ala, Glu, Ser, Ile, Pro, Gln, Thr, Phe, Gly, or Leu |
| 505 | Tyr | Val |
| 506 | Met | Leu |
| 521 | Tyr | Val |
| 526 | Phe | Leu |

*The numbering of the amino acid positions is relative to a wild-type Φ29 polymerase (e.g., SEQ ID NO: 1)

Optionally, any amino acid, e.g., natural, unnatural, or rare amino acid that is not chromophoric and/or that does not contain a sulfur moiety can be substituted at amino acid position 485, e.g., wherein the numbering of positions is relative to a wild-type Φ29 polymerase (e.g., SEQ ID NO: 1). The above mutations can optionally be introduced into a parental enzyme that already comprises any number of additional amino acid substitution mutations, e.g., while maintaining polymerase activity.

TABLE 2

USEFUL DOUBLE AMINO ACID SUBSTITUTION MUTATIONS*

| First Amino Acid Position | From | To | Second Amino Acid Position | From | To |
|---|---|---|---|---|---|
| 246 | Met | Leu | 248 | Phe | Leu |
| 367 | Trp | Ser | 369 | Tyr | Val |
| 482 | Tyr | Val | 483 | Trp | Ser |
| 482 | Tyr | Val | 485 | His | Gly |
| 483 | Trp | Ser | 485 | His | Gly |
| 505 | Tyr | Val | 506 | Met | Leu |
| 521 | Tyr | Val | 526 | Phe | Leu |

*The numbering of the amino acid positions is relative to a wild-type Φ29 polymerase (e.g., SEQ ID NO: 1)

The double mutations in Table 2 can optionally be introduced into a parental enzyme that already comprises any number of additional amino acid substitution mutations e.g., while maintaining polymerase activity.

Relative to a wild-type Φ29 DNA polymerase, modifications can include any one or any combination of substitutions including: an amino acid substitution at position 128, 137, 230, 232, 246, 248, 254, 300, 315, 363, 367, 369, 378, 385, 454, 461, 482, 483, 485, 489, 494, 500, 505, 506, 521, and/or 526, optionally other than Y369R, Y369H, or Y369E. (Φ29 polymerases (and homologs thereof) that include a Y369R, Y369H, or Y369E mutation, or any combination thereof, have been disclosed previously in WO 2007/076057 POLYMERASES FOR NUCLEOTIDE ANALOG INCORPORATION, by Hanzel et al.) Thus, substitutions that can improve the photostability of polymerases optionally comprise first substitutions other than those that correspond to Y369R, Y369H, or Y369E in a wild-type Φ29 polymerase, although the modified polymerases can comprise the aforementioned mutations in combination with other substitutions. The preferred substitutions in a polymerase that can increase a polymerase's resistance to photodamage include any one or combination of the following substitutions: M246L, F248L, W367S, Y369V, Y482V, W483S, W483F, W483L, W483V, W483I, W483P, W483Q, H485G, H485N, H485K, H485R, H485A, H485E, H485S, H485I, H485P, H485Q, H485T, H485F, H485G, H485L, Y505V, M506L, Y521V, F526L, M246L and F248L, W367S and Y369V, Y482V and W483S, Y482V and H485G, W483S and H485G, Y505V and M506L, and Y521V and F526L. Additional conservative substitutions can also be made. Optionally, any amino acid, e.g., natural, unnatural, or rare amino acid that is not chromophoric and/or that does not contain a sulfur moiety can be substituted at amino acid position 485, e.g., wherein the numbering of positions is relative to a wild-type Φ29 polymerase (e.g., SEQ ID NO: 1). Useful libraries of double substitution mutants and triple substitution mutants are provided in Table 3 below.

TABLE 3

USEFUL LIBRARIES OF DOUBLE SUBSTITUTION MUTANTS*

| Library ID | First Amino Acid Position | From | To | Second Amino Acid Position | From | To |
|---|---|---|---|---|---|---|
| Lib16 | 483 | Trp | Any amino acid other than Trp, Tyr, Met, His, or Cys | 485 | His | Any amino acid other than Trp, Tyr, Met, His, or Cys |
| Lib17 | 494 | Tyr | Any amino acid other than Trp, Tyr, Met, His, or Cys | 500 | Tyr | Any amino acid other than Trp, Tyr, Met, His, or Cys |
| Lib18 | 137 | Phe | Any amino acid other than Trp, Tyr, Met, His, or Cys | 378 | Ile | Any amino acid other than Trp, Tyr, Met, His, or Cys |
| Lib19 | 230 | Phe | Any amino acid other than Trp, Tyr, Met, His, or Cys | 232 | Trp | Any amino acid other than Trp, Tyr, Met, His, or Cys |
| Lib20 | 300 | Pro | Any amino acid other than Trp, Tyr, Met, His, or Cys | 315 | Tyr | Any amino acid other than Trp, Tyr, Met, His, or Cys |

*The numbering of the amino acid positions is relative to a wild-type Φ29 polymerase (e.g., SEQ ID NO: 1)

The amino acid substitutions at either position in any of the libraries above can include any natural, unnatural, or rare amino acid that is not chromophoric and/or that does not contain a sulfur moiety. The members of the libraries above can optionally comprise any additional amino acid substitution mutation(s) of the parental polymerases from which they are constructed. For example, a parental enzyme can contain mutations to increase polymerization kinetics, e.g., 520P (SEQ ID NO: 20). Preferably, the resulting enzymes will maintain polymerization activity after combining such mutations.

TABLE 4

Lib21
USEFUL LIBRARY OF TRIPLE SUBSTITUTION MUTANTS*

| First Amino Acid Position | Substitution | Second Amino Acid Position | Substitution | Third Amino Acid Position | Substitution |
|---|---|---|---|---|---|
| 505 | Gly, Ile, Leu, Val, Tyr, Asn, Gln, Ser, Thr, Lys, Asp, or Glu | 506 | Ala, Ile, Met, Val, Gln, Asp, or Leu | 521 | Ala, Tyr, Phe, Ile, Leu, or Thr |

*The numbering of the amino acid positions is relative to a wild-type Φ29 polymerase (e.g., SEQ ID NO: 1)

The members of the above library (Lib21) can optionally comprise any additional amino acid substitution mutation(s) of the parental polymerases from which they are constructed. For example, a parental enzyme can contain mutations to increase polymerization kinetics, e.g., 520P (SEQ ID NO: 20). Preferably, the resulting enzymes will maintain polymerization activity after combining such mutations.

The polymerase optionally further includes one or more mutations/deletions relative to the wild-type polymerase that provide additional properties of interest, including reducing or eliminating endogenous exonuclease activity, deletion or insertion of steric features near the active site that improve specificity for an unnatural nucleotide, or that improve surface bound activity of the protein, or the like. A variety of useful additional mutations that can be used in combination with the present invention are described, e.g., in WO 2007/076057 POLYMERASES FOR NUCLEOTIDE ANALOG INCORPORATION by Hanzel et al.; PCT/US2007/022459 POLYMERASE ENZYMES AND REAGENTS FOR ENHANCED NUCLEIC ACID SEQUENCING by Rank et al.; WO 2007/075987 ACTIVE SURFACE COUPLED POLYMERASES by Hanzel et al.; and WO 2007/076057 PROTEIN ENGINEERING STRATEGIES TO OPTIMIZE ACTIVITY OF SURFACE ATTACHED PROTEINS by Hanzel et al. For example, in particularly preferred embodiments, a parental polymerase comprising the mutations N62D, T368F, E375Y, and K512Y can be further modified to include the photoprotective mutations described herein. in addition to the pairs of mutations listed in Table 6.

As will be appreciated, numbering of amino acid residues is typically given with respect to a particular reference polymerase, such as the wild-type sequence of the Φ29 polymerase, e.g., SEQ ID NO: 1; actual position of a mutation within a molecule of the invention may vary based upon the nature of the various modifications that the enzyme includes relative to the wild type Φ29 enzyme, e.g., deletions and/or additions to the molecule, either at the termini or within the molecule itself.

Affinity Tags and Other Optional Polymerase Features

The recombinant enzymes of the invention optionally include additional features exogenous or heterologous to the enzyme. For example, the recombinant polymerase optionally includes one or more exogenous affinity tags, e.g., purification or substrate binding tags, such as a polyhistidine tag sequence, a 6 His tag sequence, a GST tag, an HA tag sequence, a plurality of 6 His tag sequences, a plurality of GST tags, a plurality of HA tag sequences, a SNAP-tag, a c-myc tag, a c-myc fusion, or the like. These and other features useful in the context of coupling an enzyme to a surface, or purifying the enzyme are optionally included, e.g., to orient and/or protect the enzyme's active site when the polymerase is bound to a surface. Other useful features include recombinant dimer domains of the enzyme, and, e.g., large extraneous polypeptide domains coupled to the polymerase distal to the active site. For example, for Φ29, the active site is in the C terminal region of the protein, and added surface binding elements (extra domains, His tags, etc.) are typically located in the N-terminal region to avoid interfering with the active site when the polymerase is coupled to a surface. For further details regarding these types of modifications, see, e.g., WO 2007/075987 ACTIVE SURFACE COUPLED POLYMERASES by Hanzel et al., and WO 2007/076057 PROTEIN ENGINEERING STRATEGIES TO OPTIMIZE ACTIVITY OF SURFACE ATTACHED PROTEINS by Hanzel et al.

In general, surface binding elements and purification tags that can be added to the enzymes (recombinantly or, e.g., chemically) include, e.g., polyhistidine tags, HIS-6 tags, biotin, avidin, GST sequences, modified GST sequences, e.g., that are less likely to form dimers, BiTag sequences, S tags, SNAP-tags, enterokinase sites, thrombin sites, antibodies or antibody domains, antibody fragments, antigens, receptors, receptor domains, receptor fragments, ligands, dyes, acceptors, quenchers, or combinations thereof.

Multiple surface binding domains can be added to orient the polypeptide relative to a surface and/or to increase binding of the polymerase to the surface. By binding a surface at two or more sites, through two or more separate tags, the polymerase is held in a relatively fixed orientation with respect to the surface. Additional details on fixing a polymerase to a surface, attaching tags, and the like are found in WO 2007/075987 ACTIVE SURFACE COUPLED POLYMERASES by Hanzel, et al., and WO 2007/076057 PROTEIN ENGINEERING STRATEGIES TO OPTIMIZE ACTIVITY OF SURFACE ATTACHED PROTEINS by Hanzel et al.

Making and Isolating Recombinant Enzymes

Generally, nucleic acids encoding a polymerase of the invention can be made by cloning, recombination, in vitro synthesis, in vitro amplification and/or other available methods. A variety of recombinant methods can be used for expressing an expression vector that encodes a polymerase or other enzyme of the invention, e.g., a mutant polymerase that displays enhanced photostability, or that can be coupled to an appropriate quencher to render it more photostable. Recombinant methods for making nucleic acids, expression and isolation of expressed products are well known and described in the art.

Useful references for mutation, recombinant and in vitro nucleic acid manipulation methods (including cloning, expression, PCR, and the like) include Berger and Kimmel, *Guide to Molecular Cloning Techniques, Methods in Enzymology* volume 152 Academic Press, Inc., San Diego, Calif.

(Berger); Kaufman et al. (2003) *Handbook of Molecular and Cellular Methods in Biology and Medicine Second Edition* Ceske (ed) CRC Press (Kaufman); and *The Nucleic Acid Protocols Handbook* Ralph Rapley (ed) (2000) Cold Spring Harbor, Humana Press Inc (Rapley); Chen et al. (ed) *PCR Cloning Protocols*, Second Edition (Methods in Molecular Biology, volume 192) Humana Press; and in Viljoen et al. (2005) *Molecular Diagnostic PCR Handbook* Springer, ISBN 1402034032.

In addition, a plethora of kits are commercially available for the purification of plasmids or other relevant nucleic acids from cells, (see, e.g., EasyPrep™, FlexiPrep™ both from Pharmacia Biotech; StrataClean™, from Stratagene; and, QIAprep™ from Qiagen). Any isolated and/or purified nucleic acid can be further manipulated to produce other nucleic acids, used to transfect cells, incorporated into related vectors to infect organisms for expression, and/or the like. Typical cloning vectors contain transcription and translation terminators, transcription and translation initiation sequences, and promoters useful for regulation of the expression of the particular target nucleic acid. The vectors optionally comprise generic expression cassettes containing at least one independent terminator sequence, sequences permitting replication of the cassette in eukaryotes, or prokaryotes, or both, (e.g., shuttle vectors) and selection markers for both prokaryotic and eukaryotic systems. Vectors are suitable for replication and integration in prokaryotes, eukaryotes, or both.

Other useful references, e.g. for cell isolation and culture (e.g., for subsequent nucleic acid isolation) include Freshney (1994) *Culture of Animal Cells, a Manual of Basic Technique*, Third edition, Wiley-Liss, New York and the references cited therein; Payne et al. (1992) *Plant Cell and Tissue Culture in Liquid Systems* John Wiley & Sons, Inc. New York, N.Y.; Gamborg and Phillips (eds) (1995) *Plant Cell, Tissue and Organ Culture*; Fundamental Methods Springer Lab Manual, Springer-Verlag (Berlin Heidelberg New York) and Atlas and Parks (eds) *The Handbook of Microbiological Media* (1993) CRC Press, Boca Raton, Fla.

A variety of protein isolation and detection methods are known and can be used to isolate polymerases, e.g., from recombinant cultures of cells expressing the recombinant polymerases and other enzymes of the invention. A variety of protein isolation and detection methods are well known in the art, including, e.g., those set forth in R. Scopes, *Protein Purification*, Springer-Verlag, N.Y. (1982); Deutscher, *Methods in Enzymology* Vol. 182: *Guide to Protein Purification*, Academic Press, Inc. N.Y. (1990); Sandana (1997) *Bioseparation of Proteins*, Academic Press, Inc.; Bollag et al. (1996) *Protein Methods*, $2^{nd}$ Edition Wiley-Liss, NY; Walker (1996) *The Protein Protocols Handbook* Humana Press, NJ, Harris and Angal (1990) *Protein Purification Applications: A Practical Approach* IRL Press at Oxford, Oxford, England; Harris and Angal *Protein Purification Methods: A Practical Approach* IRL Press at Oxford, Oxford, England; Scopes (1993) *Protein Purification: Principles and Practice* $3^{rd}$ Edition Springer Verlag, NY; Janson and Ryden (1998) *Protein Purification: Principles, High Resolution Methods and Applications*, Second Edition Wiley-VCH, NY; and Walker (1998) *Protein Protocols on CD-ROM* Humana Press, NJ; and the references cited therein. Additional details regarding protein purification and detection methods can be found in Satinder Ahuja ed., *Handbook of Bioseparations*, Academic Press (2000).

Kits

The present invention also provides kits that incorporate the polymerases of the invention, optionally with additional useful reagents such as one or more nucleotide analogs, e.g., for sequencing, nucleic acid amplification, or the like. Such kits can include the polymerase of the invention packaged in a fashion to enable use of the polymerase, a set of different nucleotide analogs of the invention, e.g., those that are analogous to A, T, G, and C, e.g., where one or more of the analogs comprise a detectable moiety, to permit identification in the presence of the analogs. Depending upon the desired application, the kits of the invention optionally include additional reagents, such as natural nucleotides, a control template, and other reagents, such as buffer solutions and/or salt solutions, including, e.g., divalent metal ions, i.e., $Mg^{++}$, $Mn^{++}$, $Ca^{++}$, and/or $Fe^{++}$, standard solutions, e.g., dye standards for detector calibration. Such kits also typically include instructions for use of the compounds and other reagents in accordance with the desired application methods, e.g., nucleic acid sequencing, amplification and the like.

Nucleic Acid and Polypeptide Sequence and Variants

As described herein, the invention provides polynucleotide sequences encoding, e.g., a polymerase as described herein. However, one of skill in the art will immediately appreciate that the invention is not limited to the specifically exemplified sequences. For example, one of skill will appreciate that the invention also provides, e.g., many related sequences with the functions described herein, e.g., polynucleotides and polypeptides encoding conservative variants of any of the novel polymerases described herein. Combinations of any of the mutations noted herein or combinations of any of the mutations herein in combination with those noted in other available references relating to improved polymerases, such as Hanzel et al. WO 2007/076057 POLYMERASES FOR NUCLEOTIDE ANALOG INCORPORATION; Rank et al. PCT/US2007/022459 POLYMERASE ENZYMES AND REAGENTS FOR ENHANCED NUCLEIC ACID SEQUENCING; Hanzel et al. WO 2007/075987 ACTIVE SURFACE COUPLED POLYMERASES; and Hanzel et al. WO 2007/076057 PROTEIN ENGINEERING STRATEGIES TO OPTIMIZE ACTIVITY OF SURFACE ATTACHED PROTEINS are also features of the invention.

Accordingly, the invention provides a variety of polypeptides (polymerases) and polynucleotides (nucleic acids that encode polymerases). Example polynucleotides of the invention include, e.g., a polynucleotide comprising a nucleotide sequence as set forth in FIG. 6, which sequences are SEQ ID NOs: 13-19, or a polynucleotide that is complementary to or that encodes a polynucleotide sequence thereof (e.g., where the given sequence is a DNA, an RNA is one example of a sequence that encodes the DNA, e.g., via reverse transcription). A polynucleotide of the invention also optionally includes any polynucleotide that encodes a novel polymerase described herein. Because of the degeneracy of the genetic code, many polynucleotides equivalently encode a given polymerase sequence. Similarly, an artificial or recombinant nucleic acid that hybridizes to a polynucleotide indicated above under highly stringent conditions over substantially the entire length of the nucleic acid (and is other than a naturally occurring polynucleotide) is a polynucleotide of the invention. In one embodiment, a composition includes a polypeptide of the invention and an excipient (e.g., buffer, water, pharmaceutically acceptable excipient, etc.). The invention also provides an antibody or antisera specifically immunoreactive with a polypeptide of the invention (e.g., that specifically recognizes a feature of the polymerase that confers increased photostability).

In certain embodiments, a vector (e.g., a plasmid, a cosmid, a phage, a virus, etc.) comprises a polynucleotide of the invention. In one embodiment, the vector is an expression vector. In another embodiment, the expression vector includes a promoter operably linked to one or more of the polynucleotides of the invention. In another embodiment, a cell comprises a vector that includes a polynucleotide of the invention.

One of skill will also appreciate that many variants of the disclosed sequences are included in the invention. For example, conservative variations of the disclosed sequences that yield a functionally similar sequence are included in the invention. Variants of the nucleic acid polynucleotide sequences, wherein the variants hybridize to at least one disclosed sequence, are considered to be included in the invention. Unique subsequences of the sequences disclosed herein, as determined by, e.g., standard sequence comparison techniques, are also included in the invention.

Conservative Variations

Owing to the degeneracy of the genetic code, "silent substitutions" (i.e., substitutions in a nucleic acid sequence which do not result in an alteration in an encoded polypeptide) are an implied feature of every nucleic acid sequence that encodes an amino acid sequence. Similarly, "conservative amino acid substitutions," where one or a limited number of amino acids in an amino acid sequence are substituted with different amino acids with highly similar properties, are also readily identified as being highly similar to a disclosed construct. Such conservative variations of each disclosed sequence are a feature of the present invention.

"Conservative variations" of a particular nucleic acid sequence refers to those nucleic acids that encode identical or essentially identical amino acid sequences, or, where the nucleic acid does not encode an amino acid sequence, to essentially identical sequences. One of skill will recognize that individual substitutions, deletions or additions which alter, add or delete a single amino acid or a small percentage of amino acids (typically less than 5%, more typically less than 4%, 2% or 1%) in an encoded sequence are "conservatively modified variations" where the alterations result in the deletion of an amino acid, addition of an amino acid, or substitution of an amino acid with a chemically similar amino acid, while retaining the relevant mutational feature (for example, the conservative substitution can be of a residue distal to the active site region, or distal to an interdomain stability region). Thus, "conservative variations" of a listed polypeptide sequence of the present invention include substitutions of a small percentage, typically less than 5%, more typically less than 2% or 1%, of the amino acids of the polypeptide sequence, with an amino acid of the same conservative substitution group. Finally, the addition of sequences that do not alter the encoded activity of a nucleic acid molecule, such as the addition of a non-functional or tagging sequence (introns in the nucleic acid, poly His or similar sequences in the encoded polypeptide, etc.), is a conservative variation of the basic nucleic acid or polypeptide.

Conservative substitution tables providing functionally similar amino acids are well known in the art, where one amino acid residue is substituted for another amino acid residue having similar chemical properties (e.g., aromatic side chains or positively charged side chains), and therefore does not substantially change the functional properties of the polypeptide molecule. The following sets forth example groups that contain natural amino acids of like chemical properties, where any substitution within a group is a "conservative substitution".

| Conservative Amino Acid Substitutions | | | | |
|---|---|---|---|---|
| Nonpolar and/or Aliphatic Side Chains | Polar, Uncharged Side Chains | Aromatic Side Chains | Positively Charged Side Chains | Negatively Charged Side Chains |
| Glycine | Serine | Phenylalanine | Lysine | Aspartate |
| Alanine | Threonine | Tyrosine | Arginine | Glutamate |
| Valine | Cysteine | Tryptophan | Histidine | |
| Leucine | Methionine | | | |
| Isoleucine | Asparagine | | | |
| Proline | Glutamine | | | |

Additional similar lists of conservative substitutions are available in the art. See, e.g., Bordo, et al., (1991) "Suggestions for "Safe" Residue Substitutions in Site-Directed Mutagenesis." *J Mol Biol* 217: 721-729.

Nucleic Acid Hybridization

Comparative hybridization can be used to identify nucleic acids of the invention, including conservative variations of nucleic acids of the invention. In addition, target nucleic acids which hybridize to a nucleic acid encoding one of the novel polymerases described herein under high, ultra-high and ultra-ultra high stringency conditions, where the nucleic acids encode mutations corresponding to those noted elsewhere herein are a feature of the invention. Examples of such nucleic acids include those with one or a few silent or conservative nucleic acid substitutions as compared to a given nucleic acid sequence encoding a novel polymerase described herein (or other exemplified polymerase), where any conservative substitutions are for residues other than those noted herein or elsewhere as being relevant to a feature of interest (e.g., improved photostability).

A test nucleic acid is said to specifically hybridize to a probe nucleic acid when it hybridizes at least 50% as well to the probe as to the perfectly matched complementary target, i.e., with a signal to noise ratio at least half as high as hybridization of the probe to the target under conditions in which the perfectly matched probe binds to the perfectly matched complementary target with a signal to noise ratio that is at least about 5×-10× as high as that observed for hybridization to any of the unmatched target nucleic acids.

Nucleic acids "hybridize" when they associate, typically in solution. Nucleic acids hybridize due to a variety of well-characterized physico-chemical forces, such as hydrogen bonding, solvent exclusion, base stacking and the like. An extensive guide to the hybridization of nucleic acids is found in Tijssen (1993) *Laboratory Techniques in Biochemistry and Molecular Biology—Hybridization with Nucleic Acid Probes* part I chapter 2, "Overview of principles of hybridization and the strategy of nucleic acid probe assays," (Elsevier, New York), as well as in *Current Protocols in Molecular Biology*, Ausubel et al., eds., *Current Protocols*, a joint venture between Greene Publishing Associates, Inc. and John Wiley & Sons, Inc., (supplemented through 2004) ("Ausubel"); Hames and Higgins (1995) *Gene Probes* 1 IRL Press at Oxford University Press, Oxford, England, (Hames and Higgins 1) and Hames and Higgins (1995) *Gene Probes* 2 IRL Press at Oxford University Press, Oxford, England (Hames and Higgins 2) provide details on the synthesis, labeling, detection and quantification of DNA and RNA, including oligonucleotides.

An example of stringent hybridization conditions for hybridization of complementary nucleic acids which have more than 100 complementary residues on a filter in a Southern or northern blot is 50% formalin with 1 mg of heparin at 42° C., with the hybridization being carried out overnight. An example of stringent wash conditions is a 0.2×SSC wash at 65° C. for 15 minutes (see, Sambrook, supra for a description of SSC buffer). Often the high stringency wash is preceded by a low stringency wash to remove background probe signal. An example low stringency wash is 2×SSC at 40° C. for 15 minutes. In general, a signal to noise ratio of 5× (or higher) than that observed for an unrelated probe in the particular hybridization assay indicates detection of a specific hybridization.

"Stringent hybridization wash conditions" in the context of nucleic acid hybridization experiments such as Southern and northern hybridizations are sequence dependent, and are different under different environmental parameters. An extensive guide to the hybridization of nucleic acids is found in Tijssen (1993), supra. and in Hames and Higgins, 1 and 2. Stringent hybridization and wash conditions can easily be determined empirically for any test nucleic acid. For example, in determining stringent hybridization and wash conditions, the hybridization and wash conditions are gradually increased (e.g., by increasing temperature, decreasing salt concentration, increasing detergent concentration and/or increasing the concentration of organic solvents such as formalin in the hybridization or wash), until a selected set of criteria are met. For example, in highly stringent hybridization and wash conditions, the hybridization and wash conditions are gradually increased until a probe binds to a perfectly matched complementary target with a signal to noise ratio that is at least 5× as high as that observed for hybridization of the probe to an unmatched target.

"Very stringent" conditions are selected to be equal to the thermal melting point ($T_m$) for a particular probe. The $T_m$ is the temperature (under defined ionic strength and pH) at which 50% of the test sequence hybridizes to a perfectly matched probe. For the purposes of the present invention, generally, "highly stringent" hybridization and wash conditions are selected to be about 5° C. lower than the $T_m$ for the specific sequence at a defined ionic strength and pH.

"Ultra high-stringency" hybridization and wash conditions are those in which the stringency of hybridization and wash conditions are increased until the signal to noise ratio for binding of the probe to the perfectly matched complementary target nucleic acid is at least 10× as high as that observed for hybridization to any of the unmatched target nucleic acids. A target nucleic acid which hybridizes to a probe under such conditions, with a signal to noise ratio of at least ½ that of the perfectly matched complementary target nucleic acid is said to bind to the probe under ultra-high stringency conditions.

Similarly, even higher levels of stringency can be determined by gradually increasing the hybridization and/or wash conditions of the relevant hybridization assay. For example, those in which the stringency of hybridization and wash conditions are increased until the signal to noise ratio for binding of the probe to the perfectly matched complementary target nucleic acid is at least 10×, 20×, 50×, 100×, or 500× or more as high as that observed for hybridization to any of the unmatched target nucleic acids. A target nucleic acid which hybridizes to a probe under such conditions, with a signal to noise ratio of at least ½ that of the perfectly matched complementary target nucleic acid is said to bind to the probe under ultra-ultra-high stringency conditions.

Nucleic acids that do not hybridize to each other under stringent conditions are still substantially identical if the polypeptides that they encode, e.g., photostable polymerases or other photostable enzymes, are substantially identical. This occurs, e.g., when a copy of a nucleic acid is created using the maximum codon degeneracy permitted by the genetic code.

Unique Subsequences

In some aspects, the invention provides a nucleic acid that comprises a unique subsequence in a nucleic acid that encodes one of the novel polymerases described herein. The unique subsequence may be unique as compared to a nucleic acid corresponding to, e.g., a wild type Φ29. Alignment can be performed using, e.g., BLAST set to default parameters. Any unique subsequence is useful, e.g., as a probe to identify the nucleic acids of the invention.

Similarly, the invention includes a polypeptide that comprises a unique subsequence of one of the novel polymerases described herein. Here, the unique subsequence is unique as compared to, e.g., wild type Φ29 or previously characterized mutation thereof.

The invention also provides for target nucleic acids which hybridize under stringent conditions to a unique coding oligonucleotide which encodes a unique subsequence in a polypeptide selected from the sequences of the novel polymerases described herein, wherein the unique subsequence is unique as compared to a polypeptide corresponding to wild type Φ29. Unique sequences are determined as noted above.

Sequence Comparison, Identity, and Homology

The terms "identical" or "percent identity," in the context of two or more nucleic acid or polypeptide sequences, refer to two or more sequences or subsequences that are the same or have a specified percentage of amino acid residues or nucleotides that are the same, when compared and aligned for maximum correspondence, as measured using one of the sequence comparison algorithms described below (or other algorithms available to persons of skill) or by visual inspection.

The phrase "substantially identical," in the context of two nucleic acids or polypeptides (e.g., DNAs encoding a polymerase, or the amino acid sequence of a polymerase) refers to two or more sequences or subsequences that have at least about 60%, about 80%, about 90-95%, about 98%, about 99% or more nucleotide or amino acid residue identity, when compared and aligned for maximum correspondence, as measured using a sequence comparison algorithm or by visual inspection. Such "substantially identical" sequences are typically considered to be "homologous," without reference to actual ancestry. Preferably, the "substantial identity" exists over a region of the sequences that is at least about 50 residues in length, more preferably over a region of at least about 100 residues, and most preferably, the sequences are substantially identical over at least about 150 residues, or over the full length of the two sequences to be compared. Specific sequences provided herein, e.g., amino acid sequences of photostable polymerase mutants and the nucleic acids that encode them, are an embodiment of the invention, as are sequences that are substantially identical to those provided herein.

Proteins and/or protein sequences are "homologous" when they are derived, naturally or artificially, from a common ancestral protein or protein sequence. Similarly, nucleic acids and/or nucleic acid sequences are homologous when they are derived, naturally or artificially, from a common ancestral nucleic acid or nucleic acid sequence. Homology is generally inferred from sequence similarity between two or more nucleic acids or proteins (or sequences thereof). The precise percentage of similarity between sequences that is useful in establishing homology varies with the nucleic acid and protein at issue, but as little as 25% sequence similarity over 50, 100, 150 or more residues is routinely used to establish homology. Higher levels of sequence similarity, e.g., 30%, 40%, 50%, 60%, 70%, 80%, 90%, 95%, or 99% or more, can also be used to establish homology. Methods for determining sequence similarity percentages (e.g., BLASTP and BLASTN using default parameters) are described herein and are generally available.

For sequence comparison and homology determination, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman (1981) ""Comparison of biosequences." *Adv Appl Math* 2: 482-489, by the homology alignment algorithm of Needleman & Wunsch (1970) "A general method applicable to the search for similarities in the amino acid sequence of two proteins." *J Mol Biol* 48: 443-453, by the search for similarity method of Pearson & Lipman (1988) "Improved tools for biological sequence comparison." *Proc Natl Acad Sci USA* 85: 2444-2448, by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally *Current Protocols in Molecular Biology*, Ausubel et al., eds., *Current Protocols*, a joint venture between Greene Publishing Associates, Inc. and John Wiley & Sons, Inc., supplemented through 2008).

One example of an algorithm that is suitable for determining percent sequence identity and sequence similarity is the BLAST algorithm, which is described in Altschul et al. (1990) "Basic local alignment search tool." *J Mol Biol* 215: 403-410. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff (1992) "Amino acid substitution matrices from protein blocks." *Proc Natl Acad Sci USA* 89: 10915-10919).

In addition to calculating percent sequence identity, the BLAST algorithm also performs a statistical analysis of the similarity between two sequences (see, e.g., Karlin & Altschul (1992) "Applications and statistics for multiple high-scoring segments in molecular sequences." *Proc Nat'l Acad Sci USA* 90: 5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

Nucleotide Analogs

As discussed, various polymerases of the invention can incorporate one or more nucleotide analogs into a growing oligonucleotide chain. Upon incorporation, the analog can leave a residue that is the same as or different than a natural nucleotide in the growing oligonucleotide (the polymerase can incorporate any non-standard moiety of the analog, or can cleave it off during incorporation into the oligonucleotide). As described herein "nucleotide analog" is a compound, that, in a particular application, functions in a manner similar or analogous to a naturally occurring nucleoside triphosphate (a "nucleotide"), and does not otherwise denote any particular structure. A nucleotide analog is an analog other than a standard naturally occurring nucleotide, i.e., other than A, G, C, T, or U, though upon incorporation into the oligonucleotide, the resulting residue in the oligonucleotide can be the same as (or different from) an A, G, C, T, or U residue.

In one useful aspect of the invention, nucleotide analogs can also be modified to achieve any of the improved properties desired. For example, various linkers or other substituents can be incorporated into analogs that have the effect of reducing photodamage, by moving the fluorophore away from a residue that is susceptible to damage.

Many nucleotide analogs are available and can be incorporated by the polymerases of the invention. These include analog structures with core similarity to naturally occurring nucleotides, such as those that comprise one or more substituent on a phosphate, sugar or base moiety of the nucleoside or nucleotide relative to a naturally occurring nucleoside or nucleotide. In one embodiment, the nucleotide analog includes three phosphate-containing groups; for example, the analog can be a labeled nucleoside triphosphate analog and/or an α-thiophosphate nucleotide analog having three phosphate groups. In one embodiment, a nucleotide analog can include one or more extra phosphate containing groups, relative to a nucleoside triphosphate, e.g., a nucleoside tetra-, penta-, hexa-, or heptaphosphate. For example, a variety of nucleotide analogs that comprise, e.g., from 4-6 or more phosphates are described in detail in U.S. patent application Ser. No. 11/241,809, filed Sep. 29, 2005, and incorporated herein by reference in its entirety for all purposes. Other exemplary useful analogs, including tetraphosphate and pentaphosphate analogs, are described in U.S. Pat. No. 7,041,812, incorporated herein by reference in its entirety for all purposes.

For example, the analog can include a labeled compound of the formula:

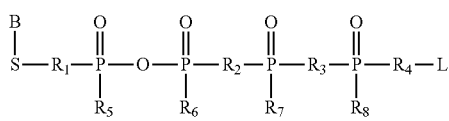

wherein B is a nucleobase (and optionally includes a label); S is selected from a sugar moiety, an acyclic moiety or a carbocyclic moiety (and optionally includes a label); L is an optional detectable label; $R_1$ is selected from O and S; $R_2$, $R_3$ and $R_4$ are independently selected from O, NH, S, methylene, substituted methylene, C(O), C(CH$_2$), CNH$_2$, CH$_2$CH$_2$, C(OH)CH$_2$R where R is 4-pyridine or 1-imidazole, provided that $R_4$ may additionally be selected from

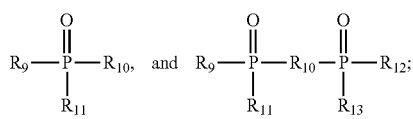

$R_5$, $R_6$, $R_7$, $R_8$, $R_{11}$ and $R_{13}$ are, when present, each independently selected from O, BH$_3$, and S; and $R_9$, $R_{10}$ and $R_{12}$ are independently selected from O, NH, S, methylene, substituted methylene, CNH$_2$, CH$_2$CH$_2$, C(OH)CH$_2$R where R is 4-pyridine or 1-imidazole. In some cases, phosphonate analogs may be employed as the analogs, e.g., where one of $R_2$, $R_3$, $R_4$, $R_9$, $R_{10}$ or $R_{12}$ are not O, e.g., they are methyl etc. See, e.g., U.S. patent application Ser. No. 11/241,809, previously incorporated herein by reference in its entirety for all purposes.

The base moiety incorporated into the analog is generally selected from any of the natural or non-natural nucleobases or nucleobase analogs, including, e.g., purine or pyrimidine bases that are routinely found in nucleic acids and available nucleic acid analogs, including adenine, thymine, guanine, cytidine, uracil, and in some cases, inosine. As noted, the base optionally includes a label moiety. For convenience, nucleotides and nucleotide analogs are generally referred to based upon their relative analogy to naturally occurring nucleotides. As such, an analog that operates, functionally, like adenosine triphosphate, may be generally referred to herein by the shorthand letter A. Likewise, the standard abbreviations of T, G, C, U and I, may be used in referring to analogs of naturally occurring nucleosides and nucleotides typically abbreviated in the same fashion. In some cases, a base may function in a more universal fashion, e.g., functioning like any of the purine bases in being able to hybridize with any pyrimidine base, or vice versa. The base moieties used in the present invention, e.g., for sequencing reactions and the like, may include the conventional bases described herein or they may include such bases substituted at one or more side groups, or other fluorescent bases or base analogs, such as 1,N6 ethenoadenosine or pyrrolo C, in which an additional ring structure renders the B group neither a purine nor a pyrimidine. For example, in certain cases, it may be desirable to substitute one or more side groups of the base moiety with a labeling group or a component of a labeling group, such as one of a donor or acceptor fluorophore, or other labeling group. Examples of labeled nucleobases and processes for labeling such groups are described in, e.g., U.S. Pat. Nos. 5,328,824 and 5,476,928, each of which is incorporated herein by reference in its entirety for all purposes.

In the analogs, the S group is optionally a sugar moiety that provides a suitable backbone for a synthesizing nucleic acid strand. For example, the sugar moiety is optionally selected from a D-ribosyl, 2' or 3' D-deoxyribosyl, 2',3'-D-dideoxyribosyl, 2',3'-D-didehydrodideoxyribosyl, 2' or 3' alkoxyribosyl, 2' or 3' aminoribosyl, 2' or 3' mercaptoribosyl, 2' or 3' alkothioribosyl, acyclic, carbocyclic or other modified sugar moieties. A variety of carbocyclic or acyclic moieties can be incorporated as the "S" group in place of a sugar moiety, including, e.g., those described in U.S. Patent Application Publication No. 2003/0124576, which is incorporated herein by reference in its entirety for all purposes.

For most cases, the phosphorus containing chain in the analogs, e.g., a triphosphate in conventional NTPs, is preferably coupled to the 5' hydroxyl group, as in natural nucleoside triphosphates. However, in some cases, the phosphorus containing chain is linked to the S group by the 3' hydroxyl group.

L generally refers to a detectable labeling group that is coupled to the terminal phosphorus atom via the $R_4$ (or $R_{10}$ or $R_{12}$) group. The labeling groups employed in the analogs of the invention may comprise any of a variety of detectable labels. Detectable labels generally denote a chemical moiety that provides a basis for detection of the analog compound separate and apart from the same compound lacking such a labeling group. Examples of labels include, e.g., optical labels, e.g., labels that impart a detectable optical property to the analog, electrochemical labels, e.g., labels that impart a detectable electrical or electrochemical property to the analog, and physical labels, e.g., labels that impart a different physical or spatial property to the analog, e.g., a mass tag or molecular volume tag. In some cases individual labels or combinations may be used that impart more than one of the aforementioned properties to the analogs of the invention. The present invention provides enzymes, e.g. polymerases, that retain their activity, e.g., polymerization activity, in the presence of such labels.

Optionally, the labeling groups incorporated into the analogs comprise optically detectable moieties, such as luminescent, chemiluminescent, fluorescent, fluorogenic, chromophoric and/or chromogenic moieties, with fluorescent and/or fluorogenic labels being preferred. A variety of different label moieties are readily employed in nucleotide analogs. Such groups include fluorescein labels, rhodamine labels, cyanine labels (i.e., Cy3, Cy5, and the like), generally available from the Amersham Biosciences division of GE Healthcare), the Alexa family of fluorescent dyes, and other fluorescent and fluorogenic dyes available from Life Technologies, Molecular Probes/Invitrogen, Inc. and described in 'The Handbook—A Guide to Fluorescent Probes and Labeling Technologies, Tenth Edition' (2005) (available from Invitrogen, Inc./Molecular Probes). A variety of other fluorescent and fluorogenic labels for use with nucleoside polyphosphates, and which would be applicable to the nucleotide analogs incorporated by the polymerases of the present invention, are described in, e.g., United States Patent Application Publication No. 2003/0124576, previously incorporated herein by reference in its entirety for all purposes.

Additional details regarding analogs and methods of making such analogs can be found in U.S. patent application Ser. No. 11/241,809, filed Sep. 29, 2005, and incorporated herein by reference in its entirety for all purposes.

Thus, in one illustrative example, the analog can be a phosphate analog (e.g., an analog that has more than the typical number of phosphates found in nucleoside triphosphates) that include, e.g., an Alexa dye label. For example, an Alexa488 dye can be labeled on a delta phosphate of a tetraphosphate analog (denoted, e.g., A488dC4P or A488dA4P, for the Alexa488 labeled tetraphosphate analogs of C and A, respectively), or an Alexa568 or Alexa633 dye can be used (e.g., A568dC4P and A633dC4P, respectively, for labeled tetraphosphate analogs of C), or an Alexa546 dye can be used (e.g., A546dG4P), or an Alexa594 dye can be used (e.g., A594dT4P). Similarly, to facilitate color separation, a pair of fluorophores exhibiting FRET (fluorescence resonance energy transfer) can be labeled on a delta phosphate of a tetraphosphate analog (denoted, e.g., FAM-amb-A532dG4P or FAM-amb-A594dT4P).

The invention provides methods of producing modified enzymes that exhibit increased resistance to photodamage. Enzymes that can particularly benefit from the methods described herein are DNA polymerases. Such modified polymerases can be assayed for their photodamage resistance phenotypes using the methods described in the example below.

EXAMPLES

Example

96 Well Format Flat-Glass Photodamage Assay

Minimizing the effects of photodamage in an analysis that makes use of optically detectable labeling groups is possible when the analysis is performed under conditions in which the reactants, e.g., enzymes, are present far in excess, e.g., where the number of enzyme molecules that do not sustain photodamage generally outnumber the enzyme molecules that are damaged by optical energy. However, an increasing number of analyses are performed with single enzyme molecules or with very few enzyme molecules. When fewer enzyme molecules are present in a reaction, damage to any one enzyme, e.g., from exposure to light sources or fluorescent detection, can have a detrimental impact on the operation of the analysis, e.g., reducing read length.

For example, in real-time sequencing by synthesis (SBS) technologies, detecting the incorporation of a nucleotide into a sequencing product entails the immobilization of, e.g., a single DNA polymerase in an illuminated nanofluidic reaction chamber in the presence of a template and nucleotide analogs that comprise fluorescent labels. When a particular base in the template strand is encountered by the polymerase during the polymerization reaction, it complexes with an available labeled nucleotide analogue that is complementary to that template nucleotide. As the polymerase incorporates the complementary labeled nucleotide (e.g., "cognate nucleotide") or nucleotide analog (e.g., "cognate analog") into the nascent and growing nucleic acid strand, the enzyme holds the cognate analog in its active site. During this time, the fluorescent label linked to the cognate analog emits an optical signal whose color corresponds to the nucleotide base's identity.

Because the fluorescent label of a cognate nucleotide analog generates highly reactive singlet oxygen species, the immobilized polymerase's active site is highly susceptible to photodamage, e.g., cognate photodamage. As used herein, "cognate photodamage" refers to the photodamage that occurs at a polymerase's active site, which results from the occupation of the active site by a cognate nucleotide or cognate analog comprising an optical label. In fact, most of the photodamage sustained by a polymerase in a single-molecule sequencing reaction occurs when an optically labeled cognate nucleotide or cognate analog is in the polymerization active site of the polymerase, e.g., in the nucleotide binding pocket. In contrast, a non-complementary nucleotide or nucleotide analog (e.g., non-cognate nucleotide or non-cognate analog) comprising a fluorescent label does not bind the polymerase active site with the same affinity, and, accordingly, the photodamage sustained by the polymerase enzyme by a non-cognate analog is low. (Low active site photodamage is also observed when free fluorescent dye is present in the sequencing reaction, e.g., at the same concentration as a labeled nucleotide analog.) Thus, the decreased activity of a photodamaged polymerase in a single-molecule sequencing reaction can generally be attributable to cognate photodamage.

The invention provides methods of generating modified recombinant polymerases, and other modified recombinant enzymes, that exhibit increased resistance to photodamage. However, single-molecule analyses are expensive and impractical for screening e.g., libraries comprising hundreds of mutant polymerases, for their photodamage resistance phenotypes. Furthermore, for the reasons described above, it can be difficult to detect cognate photodamage, or to distinguish cognate photodamage from non-cognate photodamage, in a bulk reaction, e.g., in which the reactants, e.g., polymerase molecules, are present in excess. Enzyme molecules in bulk reactions can diffuse freely within a large reaction volume, and illumination of the reaction from any source will not affect each enzyme molecule with the equivalent amount of optical energy for the same amount of time.

This example describes an assay that can be used to determine the resistance of a candidate polymerase mutant to cognate photodamage in a bulk reaction, e.g., wherein the polymerase molecules are in excess. Briefly, the assay entails capturing the biotinylated polymerase/template complexes on a streptavidin-coated surface. This immobilization permits the uniform exposure of the polymerases in the bulk reaction to highly reactive singlet oxygen species that are produced by the excitation of a high quantum yield label, e.g., a fluorescent label. This assay allows high-throughput screening of, e.g., candidate polymerase mutants to identify those mutants that exhibit resistance to cognate photodamage.

In addition, this assay can also be used in high-throughput screens to identify potential photodamage mitigating compounds. The assay can be advantageously used to determine the degree to which cognate photodamage can be minimized using alternate sources of illumination, e.g., LED illumination, laser illumination, etc., and/or under alternate reaction conditions, e.g., in the presence of $O_2$, in the presence of low $O_2$, in the absence of $O_2$, etc. Further details regarding the maintenance of low oxygen or anaerobic conditions, e.g., in a sequencing reaction, are described in, e.g., U.S. Provisional Patent Application No. 61/127,438, entitled "METHODS AND SYSTEMS FOR MITIGATING OXYGEN ENHANCED DAMAGE IN REAL-TIME ANALYTICAL OPERATIONS," by Dixon, et al., filed May 13, 2008, previously incorporated by reference. Optionally, nucleotide analogs comprising a variety of optical labels can also be screened in the assay, e.g., to identify those that cause the least cognate photodamage to the active site of a polymerase while still producing a detectable signal.

Furthermore, the assay can be performed by hand, or it can be automated. Both modes have been shown to produce consistent results, e.g., wherein a polymerase with a known photodamage resistance phenotype can be assayed either by hand or via robot and be shown to exhibit the same, e.g., expected, rate of decay in polymerization activity after exposure to optical energy for a given length of time.

To begin the assay, 100 nM of, e.g., each of a variety of candidate biotin-tagged polymerase mutants, is incubated with 150 nM of primer-bound template, e.g., 31-32 primer-template minicircles, in 50 μl volumes of 1×ACES buffer (50 mM ACES, pH=7.1, 75 mM KOAc, 0.05% Tween-20, and 5 mM DTT)+1 mM $CaCl_2$, to permit the formation of enzyme/template complexes. Each of the biotinylated polymerase mutant/template complexes are then transferred to and incubated in a separate streptavidin-coated well of a clear 96 well plate. The multi-well format of the photodamage assay allows multiple polymerase mutants to be screened in parallel, although other formats can optionally be used. The incubation takes place at room temperature for at least 15-20 minutes to permit attachment of the biotinylated polymerase/template complexes to the surfaces of the wells. Excess unbound complexes are washed away with 1×ACES buffer+1 mM $CaCl_2$. Optionally, the template and/or primer, rather than the polymerase, can comprise the biotin tag that permits the immobilization of the polymerase/template complex in a streptavidin-coated well. In fact, any of a variety of methods known to those of skill in the art, including those described previously, can be used to immobilize polymerase/template complexes to a variety of surfaces (e.g., glass, polystyrene, etc.) to perform the assay.

Next, Burn Mix is added to the wells in which mutant polymerase/template complexes have been immobilized. Burn Mix, which comprises 1×ACES buffer, 200 nM cognate nucleotide analog (comprising a fluorescent dye attached at the phosphate end), and 1 mM $CaCl_2$, provides the source of cognate photodamage, e.g., during the illumination step. Following the addition of Burn Mix, the wells are illuminated from the bottom of the plate. During the illumination step, labeled cognate nucleotide analogs occupy the immobilized polymerases' active sites, thus uniformly exposing the polymerases to equivalent levels of singlet oxygen, e.g. produced by the fluorescent label linked to the cognate nucleotide. The wells can be illuminated from about 5 to about 60 minutes. Any of a variety of illumination sources can be used, including, e.g., LEDs and lasers.

Certain polymerase mutants can comprise mutations that decrease the polymerase's affinity for the cognate nucleotide. Such polymerase mutants are less likely to be occupied by a fluorescently labeled cognate analog during the illumination step, and, thus, will not be exposed to the same level of optical energy as those polymerase mutants with high affinity for the cognate analog. The $Ca^{++}$ ions present in the Burn Mix increase the polymerase mutants' affinities for the cognate analog, thus ensuring that each mutant binds the cognate analog and that each mutant is exposed to equivalent levels of optical energy during the illumination step (or "burn step"). Alternately, the fluorescently labeled cognate analog can in the assay be supplied by an oligonucleotide comprising a 3' fluorescent label. The $Ca^{++}$ ions in the Burn Mix are non-catalytic, e.g., DNA polymerases do not exhibit polymerization activity in the presence of $Ca^{++}$ ions. Thus, the optically labeled cognate analog can occupy the active site of a DNA polymerase without being consumed, e.g., incorporated into a nascent DNA by the polymerase, during the illumination step of the assay.

Figure 2:
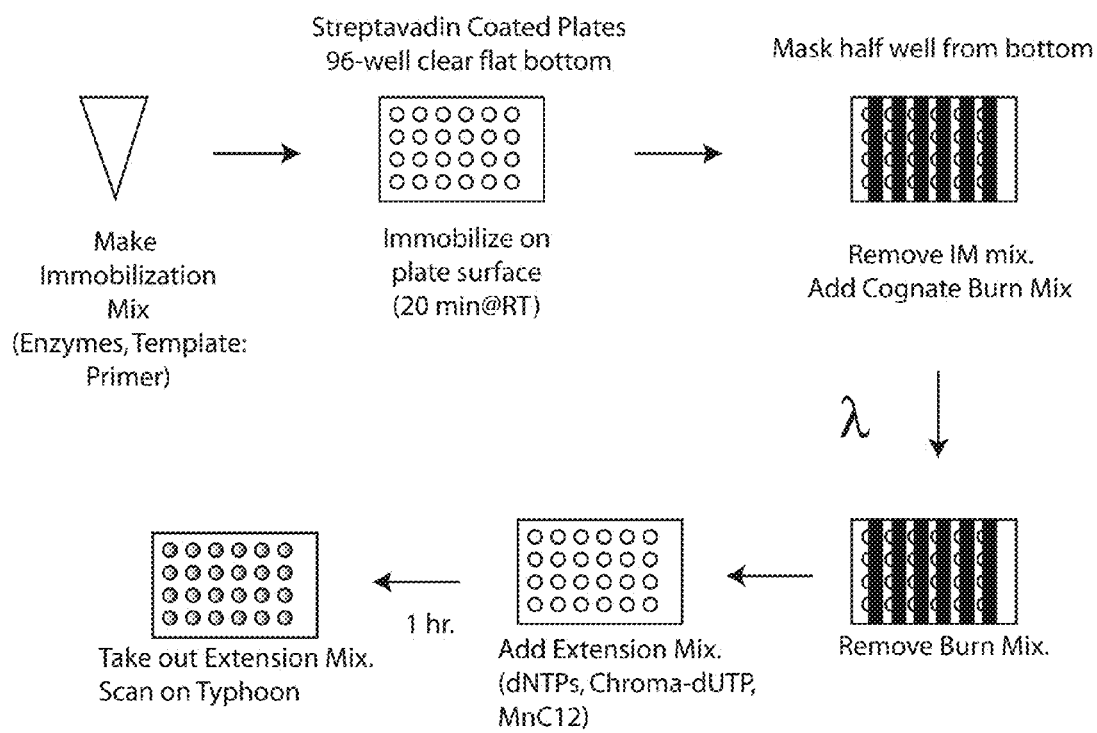
FIG. 2 provides a schematic of the workflow of the photodamage assay described in the Example.

Following the illumination step, during which the polymerases' active sites are exposed to a photosensitizer, the Burn Mix is then washed out with 1×ACES buffer+1 mM $CaCl_2$, and Extension Mix (1 uM each of dATP, dTTP, dCTP, dGTP, 200 nM base-labeled dUTP, such as ChromaTide™ dUTP-Alexa488, and 1.4 mM $MnCl_2$) is added. In the presence of all four nucleotides and $Mn^{++}$ ions, the immobilized polymerases synthesize strands of DNA comprising a sequence complementary to that of the template. The extension step can proceed for about 20 minutes, after which the extension mix is washed out with 1×ACES buffer+1 mM $CaCl_2$ 1×ACES+1 mM $CaCl_2$ is then added to each well to hold the polymerized extension products to the immobilized polymerases, and to prevent desiccation, as the immobilized polymerases become inactive once the wells have dried out. The 96-well plate is then scanned on a Typhoon Variable Mode Imager from Molecular Dynamics at a resolution of 100 microns/pixel to detect the fluorescent signal produced by ChromaTide™ dUTP-Alexa488 that has been incorporated into the extension product. A schematic of this assay is depicted in FIG. 2. The intensity of the fluorescent signal detected by the Imager correlates with the polymerization activity of each of the polymerase mutants following exposure to optical energy.

Figure 3:
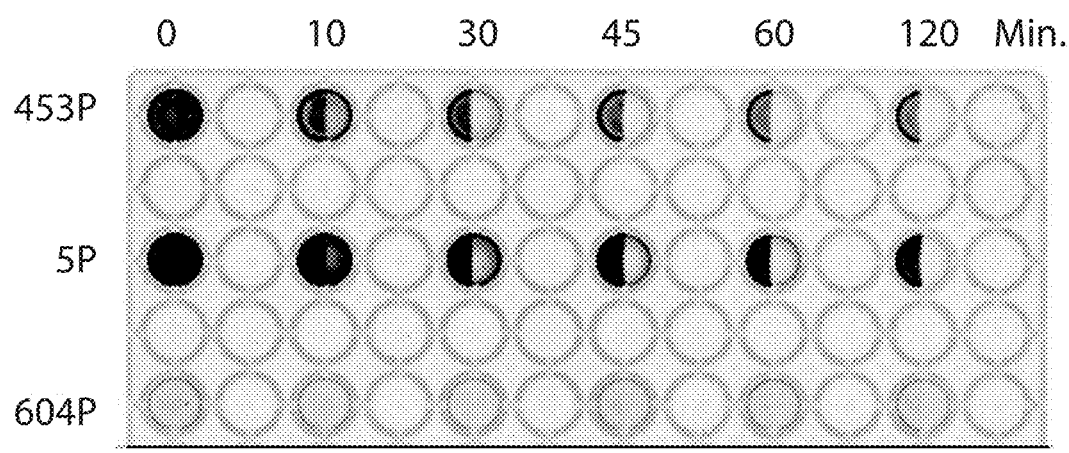
FIG. 3 shows a test plate in which the photodamage assay described in the Example was performed.

For example, LEDs can be used to illuminate wells, e.g., in which polymerase/template complexes have been bound, for up to 2 hours to generate a photodamage time course to determine the photodamage resistance phenotypes of three polymerase mutants, designated 453P, 5P, and 604P. 5P is a Φ29-derived polymerase mutant that comprises the substitution mutation N62D. 453P is derived from 5P and also includes three additional substitution mutations: T368F, E375Y, and K512Y. 604P (SEQ ID NO: 9) is a chimeric polymerase mutant derived from F29, PZA, B103, M2, and GA1 polymerases. The test plate in which the above-described assay was performed is shown in FIG. 3. In this experiment, the Immobilization Mixes included 100 nM of one of the three polymerase mutants and 150 nM of each template (31-32 primer-template minicircles). The Burn Mix included 200 nM of the fluorescently labeled cognate nucleotide analog A568-dC6P. The length of time for which each of the wells was illuminated is indicated at the top of the plate shown in FIG. 3.

Figure 4:
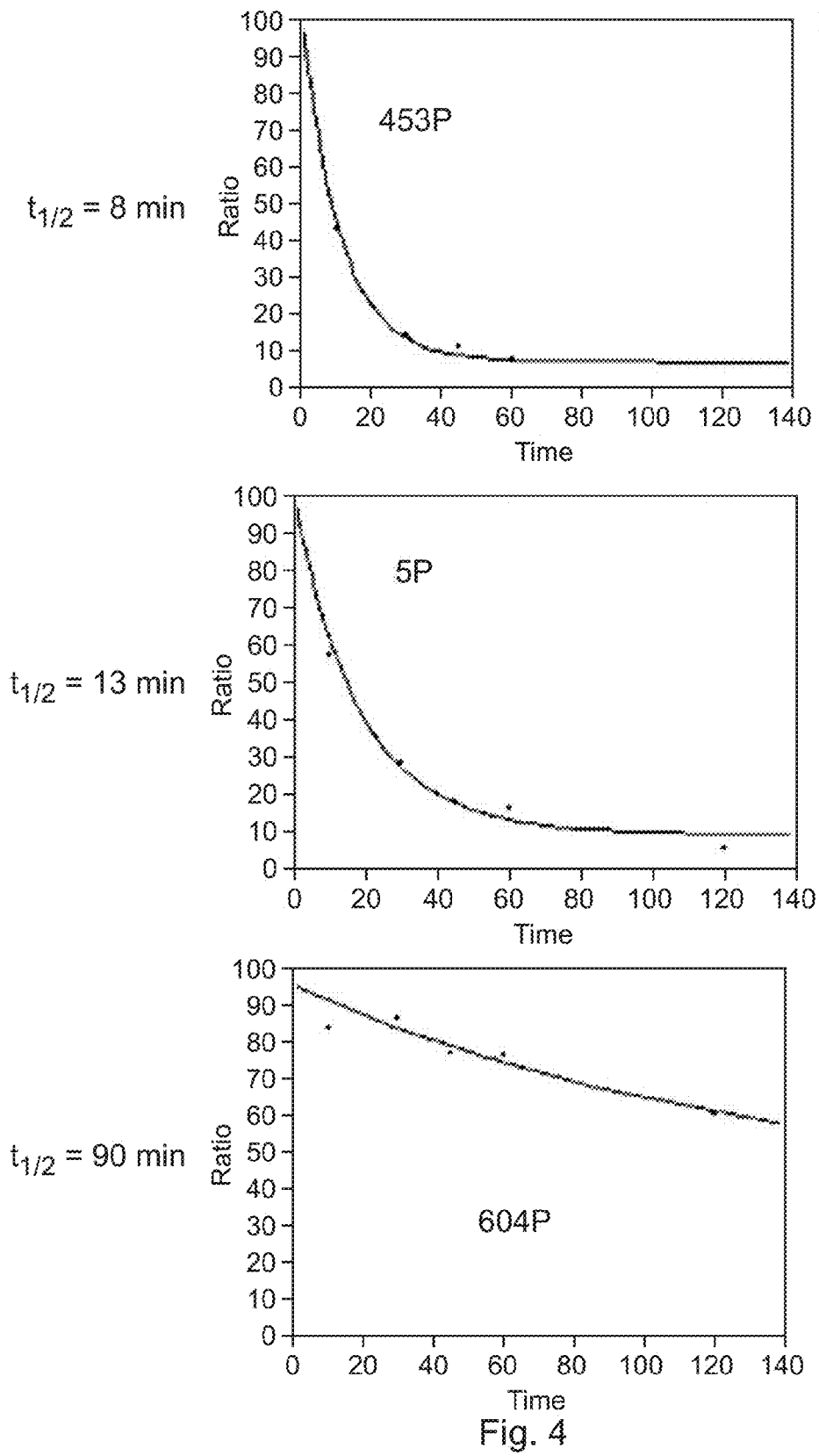
FIG. 4 shows the results of a photodamage time course experiment that was performed to determine the relative photostabilities exhibited by Φ29-derived polymerase mutants 453P, 604P, and 5P.

Prior to illuminating the wells comprising the bound polymerase mutant/template complexes, e.g., using LEDS, one half of the bottom of each well was masked to shield the complexes immobilized on that half of the well from optical energy (see FIGS. 2 and 3). Masking allows direct comparison of the polymerization activity of the polymerase mutants in the illuminated half of a well to the polymerization activity of the polymerase mutants in the masked, e.g., non-illuminated, half of the well. The ratio of these activities (e.g., illuminated polymerization activity/masked polymerization activity) is the % active polymerase remaining after exposure to optical energy for a given length of time. By calculating the activity ratios (y axis) of each polymerase mutant at each time point (x axis), the polymerization activity decay curves shown in FIG. 4 were constructed. The results shown in FIG. 4 confirm that there are measurable and significant differences between the half-lives of the three polymerase mutants tested. The activity of 453P was reduced by 50% after 8 minutes of exposure to optical energy from the cognate analog, while 604P exhibited the same reduction in activity after 90 minutes of exposure to optical energy from the same cognate analog. Thus, from these results, it can be concluded that 453P is more photosensitive than 604P enzyme. 453P comprises the substitution mutations N62D, T368F, E375Y, and K512Y. 604P (SEQ ID NO: 9) is a chimeric polymerase mutant derived from F29, PZA, B103, M2, and GA1 polymerases.

Figure 5:
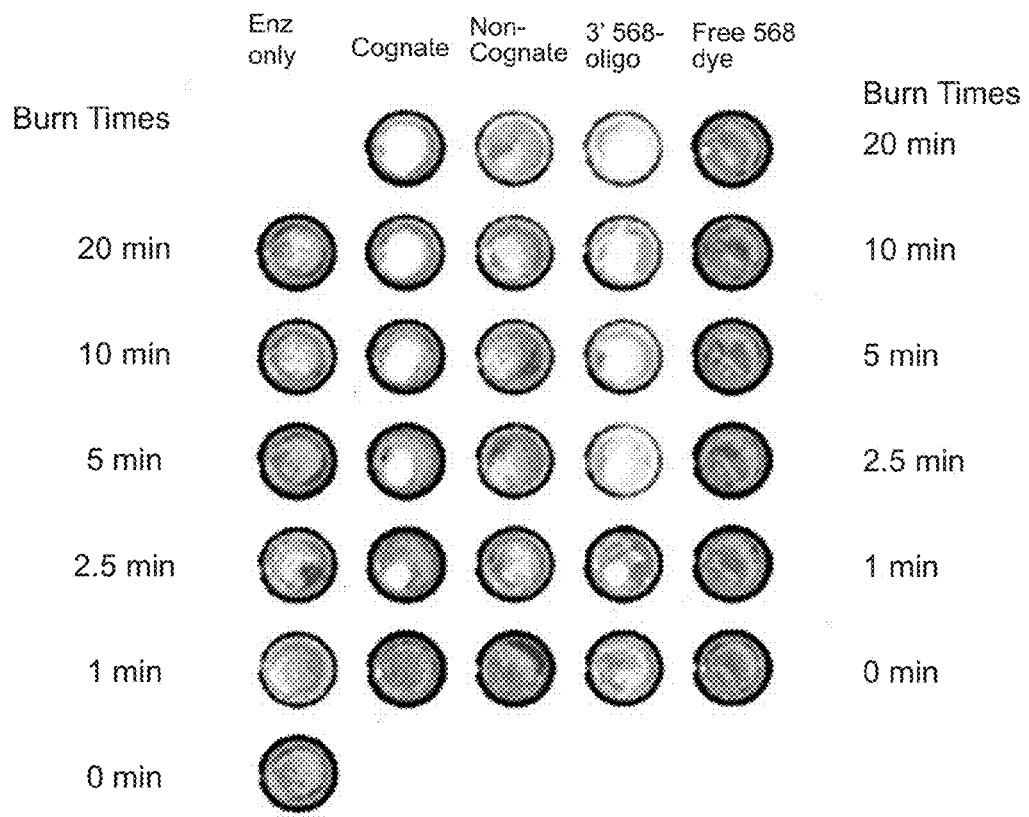
FIG. 5 shows a test plate in which the photodamage assay described herein was performed. The source of illumination in the assay was a 1 W, 800 μM laser, and the assay was performed in the presence of $O_2$.

As described above, a number of illumination sources can optionally be used during the illumination step of the photodamage assay. For example, FIG. 5 shows a test plate that was illuminated by a 1 W, 800 μm diameter laser in a photodamage assay that was performed under aerobic conditions with the Φ29-derived 453P polymerase mutant (described above). The polymerase/template complexes were illuminated with the laser for the times indicated at the sides of the test plate in the presence of the photodamage sources indicated at the top of the plate. (For example, the illumination mixes in the first column of wells did not include an optical label. The illumination mixes in the second, third, and fourth columns included a fluorescently labeled cognate analog, a fluorescently labeled non-cognate analog, a 3'-fluorescently labeled oligo template, and free fluorescent dye, respectively.)

As is shown in FIG. 5, the wells of the test plate are not masked. The illumination from a laser is specifically targeted to the center of each well, such that when the test plate is scanned, the polymerization activity at the center of each well, e.g., where the illumination was targeted, can be compared to the polymerization activity at the edge of the well, e.g., which was not illuminated, to determine the % active polymerase remaining after exposure to optical energy for a given length of time. Lasers are preferably used as a source of illumination when the photodamage assay is performed in low oxygen or in the absence of oxygen.

The results in Table 5 show that polymerase mutants 587P and 596P exhibit greater photostability than the parental polymerase 290P, e.g., from which 587P and 596P are derived. (The mutations that 587P, 596P, and 290P comprise are included in Table 5). Table 6 shows the photoresistance phenotypes of 23 Lib16 double mutants that were constructed from parental polymerase 520P. 520P comprises the mutations N62D, T368F, E375Y, and K512Y (e.g., SEQ ID NO: 20). The photoresistance phenotypes of chimeric polymerases 604P, 605P, 1093P, and 1094P are shown in Table 7. 604P, 605P, 1093P, and 1094P are derived from the polymerases encoded by SEQ ID NOs: 2-6.

The results in Tables 5, 6, and 7 were obtained using the assay described above. Each mutant was assayed in triplicate. LEDs were used in the illumination step, and the mutants were assays under aerobic conditions. "Mean photoresistance" in Tables 5, 6, and 7 indicates the average % active polymerase remaining after exposure to optical energy for 30 minutes (e.g., the average of the results of three experiments).

TABLE 5

PHOTORESISTANCE PHENOTYPES FOR Φ29-DERIVED MUTANTS COMPRISING A SINGLE AMINO ACID SUBSTITUTION (VS. PARENTAL POLYMERASE)

| Mutant | Mean Photoresistance | Standard Deviation | Mutations |
| --- | --- | --- | --- |
| 290P (parental) | 0.64 | +/− 0.02 | N62D |
| 578P | 0.48 | +/− 0.07 | N62D, M246L |
| 579P | 0.64 | +/− 0.05 | N62D, F248L |
| 581P | 0.44 | +/− 0.03 | N62D, W367S |
| 582P | 0.38 | +/− 0.08 | N62D, W367K |
| 583P | 0.65 | +/− 0.13 | N62D, Y369V |
| 584P | 0.63 | +/− 0.08 | N62D, Y369E |
| 290P (parental) | 0.64 | +/− 0.02 | N62D |
| 585P | 0.45 | +/− 0.08 | N62D, Y482V |
| 586P | 0.64 | +/− 0.07 | N62D, Y482K |
| 587P | 0.77 | +/− 0.05 | N62D, W483S |
| 588P | 0.59 | +/− 0.07 | N62D, W483V |
| 589P | 0.51 | +/− 0.11 | N62D, H485G |
| 590P | 0.49 | +/− 0.05 | N62D, Y505V |
| 591P | 0.50 | +/− 0.04 | N62D, Y505T |
| 592P | 0.65 | +/− 0.03 | N62D, M506L |
| 593P | 0.66 | +/− 0.05 | N62D, M506D |
| 594P | 0.57 | +/− 0.08 | N62D, Y521V |
| 595P | 0.62 | +/− 0.07 | N62D, Y521A |
| 596P | 0.70 | +/− 0.07 | N62D, F526L |
| 597P | 0.55 | +/− 0.08 | N62D, F526P |

TABLE 6

PHOTORESISTANCE PHENOTYPES FOR MEMBERS OF Lib16*

| Mutations | Mean Photoresistance | Standard Deviation |
| --- | --- | --- |
| 520P (parental) N62D, T368F, E375Y, K512Y | 0.41 | +/− 0.05 |
| N62D, T368F, E375Y, W483V, H485P, K512Y | 0.28 | +/− 0.16 |
| N62D, T368F, E375Y, W483A, H485P, K512Y | 0.41 | +/− 0.10 |
| N62D, T368F, E375Y, W483I, H485A K512Y, | 0.51 | +/− 0.01 |
| N62D, T368F, E375Y, W483F, H485E, K512Y | 0.53 | +/− 0.09 |
| N62D, T368F, E375Y, W483L, H485S, K512Y | 0.53 | +/− 0.04 |
| N62D, T368F, E375Y, W483F, H485N, K512Y | 0.53 | +/− 0.04 |
| N62D, T368F, E375Y, W483F, H485I, K512Y | 0.56 | +/− 0.04 |
| N62D, T368F, E375Y, W483L, H485P, K512Y | 0.56 | +/− 0.01 |
| N62D, T368F, E375Y, W483L, H485A, K512Y | 0.57 | +/− 0.07 |
| N62D, T368F, E375Y, W483F, H485Q, K512Y | 0.58 | +/− 0.02 |
| N62D, T368F, E375Y, W483F, H485P, K512Y | 0.59 | +/− 0.03 |
| N62D, T368F, E375Y, W483L, H485R, K512Y | 0.59 | +/− 0.09 |
| N62D, T368F, E375Y, W483L, H485I, K512Y | 0.60 | +/− 0.07 |
| N62D, T368F, E375Y, W483P, H485R, K512Y | 0.60 | +/− 0.01 |
| N62D, T368F, E375Y, W483F, H485A, K512Y | 0.60 | +/− 0.06 |
| N62D, T368F, E375Y, W483V, H485K, K512Y | 0.61 | +/− 0.06 |
| N62D, T368F, E375Y, W483L, H485T, K512Y | 0.62 | +/− 0.05 |
| N62D, T368F, E375Y, W483L, H485K, K512Y | 0.62 | +/− 0.04 |
| N62D, T368F, E375Y, W483L, H485Q, K512Y | 0.64 | +/− 0.05 |
| N62D, T368F, E375Y, W483L, H485F, K512Y | 0.65 | +/− 0.03 |
| N62D, T368F, E375Y, W483Q, H485G, K512Y | 0.68 | +/− 0.03 |
| N62D, T368F, E375Y, W483L, H485L, K512Y | 0.72 | +/− 0.04 |

*All the above mutants, including the parental mutant 520P, are derived from WT Φ29.

TABLE 7

PHOTORESISTANCE PHENOTYPES OF CHIMERIC DNA POLYMERASES*

| Mutant | Mean Photoresistance | Standard Deviation |
| --- | --- | --- |
| 604P | 0.96 | +/− 0.03 |
| 605P | 1.18 | +/− 0.03 |
| 1093P | 0.89 | |
| 1094P | 0.62 | |

*604P, 605P, 1093P, and 1094P are derived from the polymerases encoded by SEQ ID NOs: 2-6.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above can be used in various combinations. All publications, patents, patent applications, and/or other documents cited in this application are incorporated by reference in their entirety for all purposes to the same extent as if each individual publication, patent, patent application, and/or other document were individually indicated to be incorporated by reference for all purposes.

What is claimed is:

1. A composition comprising:
   a triplet state quencher, wherein the triplet state quencher is a trivalent lanthanide ion,
   a fluorescently labeled or fluorogenic nucleotide analog, and
   a recombinant DNA polymerase to which the triplet state quencher is noncovalently bound, wherein the recombinant polymerase comprises an amino acid sequence that is at least 90% identical to SEQ ID NO:1 or SEQ ID NO:21,
   wherein the nucleotide analog serves as a substrate for the polymerase, wherein the nucleotide analog does not comprise the triplet state quencher, and wherein the triplet state quencher serves as an acceptor for the excited triplet state of the fluorescently labeled analog or of the fluorogenic analog's product.

2. The composition of claim 1 wherein the recombinant polymerase comprises one or more mutations relative to a parental polymerase that increase the affinity of the recombinant polymerase's exonuclease domain for the trivalent lanthanide ion relative to the parental polymerase while maintaining the polymerase's polymerase activity.

3. The composition of claim 1, wherein the lanthanide ion is $Eu^{3+}$ or $Tb^{3+}$.

4. The composition of claim 2, wherein the affinity of the recombinant polymerase's exonuclease domain for the trivalent lanthanide ion is increased by at least 100-fold.

5. The composition of claim 1 wherein the recombinant polymerase comprises an EF-hand motif to which the trivalent lanthanide ion binds.

6. The composition of claim 1, wherein the recombinant polymerase comprises a first moiety to which is covalently attached a second moiety that noncovalently binds the triplet state quencher.

7. The composition of claim 6, wherein the first moiety comprises a cysteine residue and the second moiety comprises a chelator to which the trivalent lanthanide ion binds.

8. The composition of claim 1, comprising a DNA template, wherein the recombinant polymerase incorporates the nucleotide analog into a copy nucleic acid in response to the DNA template.

9. The composition of claim 1, wherein the composition is present in a DNA sequencing system.

10. The composition of claim 9, wherein the sequencing system comprises a zero mode waveguide.

11. The composition of claim 1, wherein the recombinant polymerase is immobilized on a surface.

12. A method of sequencing a DNA template, the method comprising:
   a) providing a reaction mixture comprising:
      the DNA template,
      a replication initiating moiety that complexes with or is integral to the template,
      the composition of claim 1, wherein the recombinant polymerase is capable of replicating at least a portion of the template using the moiety in a template-dependent polymerization reaction, and
      optionally one or more nucleotides and/or additional nucleotide analogs;
   b) subjecting the reaction mixture to a polymerization reaction in which the recombinant polymerase replicates at least a portion of the template in a template-dependent manner, whereby the nucleotides and/or nucleotide analogs are incorporated into the resulting DNA; and
   c) identifying a time sequence of incorporation of the nucleotides and/or nucleotide analogs into the resulting DNA.

13. The method of claim 12, wherein the subjecting and identifying steps are performed in a zero mode waveguide.

14. A method of making a DNA, the method comprising:
   a) providing a reaction mixture comprising:
      a template,
      a replication initiating moiety that complexes with or is integral to the template,
      the composition of claim 1, wherein the recombinant polymerase is capable of replicating at least a portion of the template using the moiety in a template-dependent polymerase reaction, and
      optionally one or more nucleotides and/or additional nucleotide analogs; and
   b) reacting the mixture such that the polymerase replicates at least a portion of the template in a template-dependent manner, whereby the nucleotides and/or nucleotide analogs are incorporated into the resulting DNA.

15. The method of claim 14, wherein the mixture is reacted in a zero mode waveguide.

16. The method of claim 14, the method comprising detecting incorporation of the fluorescently labeled or fluorogenic nucleotide analog.

* * * * *

SEQUENCE LISTING

<160> NUMBER OF SEQ ID NOS: 21

<210> SEQ ID NO 1
<211> LENGTH: 575
<212> TYPE: PRT
<213> ORGANISM: Bacteriophage phi-29

<400> SEQUENCE: 1

```
Met Lys His Met Pro Arg Lys Met Tyr Ser Cys Asp Phe Glu Thr Thr
1               5                   10                  15

Thr Lys Val Glu Asp Cys Arg Val Trp Ala Tyr Gly Tyr Met Asn Ile
            20                  25                  30

Glu Asp His Ser Glu Tyr Lys Ile Gly Asn Ser Leu Asp Glu Phe Met
        35                  40                  45

Ala Trp Val Leu Lys Val Gln Ala Asp Leu Tyr Phe His Asn Leu Lys
    50                  55                  60

Phe Asp Gly Ala Phe Ile Ile Asn Trp Leu Glu Arg Asn Gly Phe Lys
65                  70                  75                  80

Trp Ser Ala Asp Gly Leu Pro Asn Thr Tyr Asn Thr Ile Ile Ser Arg
                85                  90                  95

Met Gly Gln Trp Tyr Met Ile Asp Ile Cys Leu Gly Tyr Lys Gly Lys
            100                 105                 110

Arg Lys Ile His Thr Val Ile Tyr Asp Ser Leu Lys Lys Leu Pro Phe
        115                 120                 125

Pro Val Lys Lys Ile Ala Lys Asp Phe Lys Leu Thr Val Leu Lys Gly
    130                 135                 140

Asp Ile Asp Tyr His Lys Glu Arg Pro Val Gly Tyr Lys Ile Thr Pro
145                 150                 155                 160

Glu Glu Tyr Ala Tyr Ile Lys Asn Asp Ile Gln Ile Ile Ala Glu Ala
                165                 170                 175

Leu Leu Ile Gln Phe Lys Gln Gly Leu Asp Arg Met Thr Ala Gly Ser
            180                 185                 190

Asp Ser Leu Lys Gly Phe Lys Asp Ile Ile Thr Thr Lys Lys Phe Lys
        195                 200                 205

Lys Val Phe Pro Thr Leu Ser Leu Gly Leu Asp Lys Glu Val Arg Tyr
    210                 215                 220

Ala Tyr Arg Gly Gly Phe Thr Trp Leu Asn Asp Arg Phe Lys Glu Lys
225                 230                 235                 240

Glu Ile Gly Glu Gly Met Val Phe Asp Val Asn Ser Leu Tyr Pro Ala
                245                 250                 255

Gln Met Tyr Ser Arg Leu Leu Pro Tyr Gly Glu Pro Ile Val Phe Glu
            260                 265                 270

Gly Lys Tyr Val Trp Asp Glu Asp Tyr Pro Leu His Ile Gln His Ile
        275                 280                 285

Arg Cys Glu Phe Glu Leu Lys Glu Gly Tyr Ile Pro Thr Ile Gln Ile
    290                 295                 300

Lys Arg Ser Arg Phe Tyr Lys Gly Asn Glu Tyr Leu Lys Ser Ser Gly
305                 310                 315                 320

Gly Glu Ile Ala Asp Leu Trp Leu Ser Asn Val Asp Leu Glu Leu Met
                325                 330                 335

Lys Glu His Tyr Asp Leu Tyr Asn Val Glu Tyr Ile Ser Gly Leu Lys
            340                 345                 350

Phe Lys Ala Thr Thr Gly Leu Phe Lys Asp Phe Ile Asp Lys Trp Thr
        355                 360                 365
```

```
Tyr Ile Lys Thr Thr Ser Glu Gly Ala Ile Lys Gln Leu Ala Lys Leu
            370                 375                 380

Met Leu Asn Ser Leu Tyr Gly Lys Phe Ala Ser Asn Pro Asp Val Thr
385                 390                 395                 400

Gly Lys Val Pro Tyr Leu Lys Glu Asn Gly Ala Leu Gly Phe Arg Leu
                405                 410                 415

Gly Glu Glu Glu Thr Lys Asp Pro Val Tyr Thr Pro Met Gly Val Phe
            420                 425                 430

Ile Thr Ala Trp Ala Arg Tyr Thr Thr Ile Thr Ala Ala Gln Ala Cys
                435                 440                 445

Tyr Asp Arg Ile Ile Tyr Cys Asp Thr Asp Ser Ile His Leu Thr Gly
450                 455                 460

Thr Glu Ile Pro Asp Val Ile Lys Asp Ile Val Asp Pro Lys Lys Leu
465                 470                 475                 480

Gly Tyr Trp Ala His Glu Ser Thr Phe Lys Arg Ala Lys Tyr Leu Arg
                485                 490                 495

Gln Lys Thr Tyr Ile Gln Asp Ile Tyr Met Lys Glu Val Asp Gly Lys
            500                 505                 510

Leu Val Glu Gly Ser Pro Asp Asp Tyr Thr Asp Ile Lys Phe Ser Val
            515                 520                 525

Lys Cys Ala Gly Met Thr Asp Lys Ile Lys Lys Glu Val Thr Phe Glu
530                 535                 540

Asn Phe Lys Val Gly Phe Ser Arg Lys Met Lys Pro Lys Pro Val Gln
545                 550                 555                 560

Val Pro Gly Gly Val Val Leu Val Asp Asp Thr Phe Thr Ile Lys
                565                 570                 575

<210> SEQ ID NO 2
<211> LENGTH: 575
<212> TYPE: PRT
<213> ORGANISM: Artificial Sequence
<220> FEATURE:
<223> OTHER INFORMATION: DNA polymerase mutant 290P derived from WT
      phage phi29 DNA polymerase (SEQ ID NO: 1)

<400> SEQUENCE: 2

Met Lys His Met Pro Arg Lys Met Tyr Ser Cys Asp Phe Glu Thr Thr
1               5                   10                  15

Thr Lys Val Glu Asp Cys Arg Val Trp Ala Tyr Gly Tyr Met Asn Ile
            20                  25                  30

Glu Asp His Ser Glu Tyr Lys Ile Gly Asn Ser Leu Asp Glu Phe Met
        35                  40                  45

Ala Trp Val Leu Lys Val Gln Ala Asp Leu Tyr Phe His Asp Leu Lys
50                  55                  60

Phe Asp Gly Ala Phe Ile Ile Asn Trp Leu Glu Arg Asn Gly Phe Lys
65                  70                  75                  80

Trp Ser Ala Asp Gly Leu Pro Asn Thr Tyr Asn Thr Ile Ile Ser Arg
                85                  90                  95

Met Gly Gln Trp Tyr Met Ile Asp Ile Cys Leu Gly Tyr Lys Gly Lys
            100                 105                 110

Arg Lys Ile His Thr Val Ile Tyr Asp Ser Leu Lys Lys Leu Pro Phe
        115                 120                 125

Pro Val Lys Lys Ile Ala Lys Asp Phe Lys Leu Thr Val Leu Lys Gly
130                 135                 140

Asp Ile Asp Tyr His Lys Glu Arg Pro Val Gly Tyr Lys Ile Thr Pro
145                 150                 155                 160
```

```
Glu Glu Tyr Ala Tyr Ile Lys Asn Asp Ile Gln Ile Ala Glu Ala
            165                 170                 175

Leu Leu Ile Gln Phe Lys Gln Gly Leu Asp Arg Met Thr Ala Gly Ser
            180                 185                 190

Asp Ser Leu Lys Gly Phe Lys Asp Ile Ile Thr Thr Lys Lys Phe Lys
            195                 200                 205

Lys Val Phe Pro Thr Leu Ser Leu Gly Leu Asp Lys Glu Val Arg Tyr
        210                 215                 220

Ala Tyr Arg Gly Gly Phe Thr Trp Leu Asn Asp Arg Phe Lys Glu Lys
225                 230                 235                 240

Glu Ile Gly Glu Gly Met Val Phe Asp Val Asn Ser Leu Tyr Pro Ala
                245                 250                 255

Gln Met Tyr Ser Arg Leu Leu Pro Tyr Gly Glu Pro Ile Val Phe Glu
            260                 265                 270

Gly Lys Tyr Val Trp Asp Glu Asp Tyr Pro Leu His Ile Gln His Ile
        275                 280                 285

Arg Cys Glu Phe Glu Leu Lys Glu Gly Tyr Ile Pro Thr Ile Gln Ile
        290                 295                 300

Lys Arg Ser Arg Phe Tyr Lys Gly Asn Glu Tyr Leu Lys Ser Ser Gly
305                 310                 315                 320

Gly Glu Ile Ala Asp Leu Trp Leu Ser Asn Val Asp Leu Glu Leu Met
                325                 330                 335

Lys Glu His Tyr Asp Leu Tyr Asn Val Glu Tyr Ile Ser Gly Leu Lys
            340                 345                 350

Phe Lys Ala Thr Thr Gly Leu Phe Lys Asp Phe Ile Asp Lys Trp Thr
            355                 360                 365

Tyr Ile Lys Thr Thr Ser Glu Gly Ala Ile Lys Gln Leu Ala Lys Leu
        370                 375                 380

Met Leu Asn Ser Leu Tyr Gly Lys Phe Ala Ser Asn Pro Asp Val Thr
385                 390                 395                 400

Gly Lys Val Pro Tyr Leu Lys Glu Asn Gly Ala Leu Gly Phe Arg Leu
                405                 410                 415

Gly Glu Glu Glu Thr Lys Asp Pro Val Tyr Thr Pro Met Gly Val Phe
            420                 425                 430

Ile Thr Ala Trp Ala Arg Tyr Thr Thr Ile Thr Ala Ala Gln Ala Cys
        435                 440                 445

Tyr Asp Arg Ile Ile Tyr Cys Asp Thr Asp Ser Ile His Leu Thr Gly
        450                 455                 460

Thr Glu Ile Pro Asp Val Ile Lys Asp Ile Val Asp Pro Lys Lys Leu
465                 470                 475                 480

Gly Tyr Trp Ala His Glu Ser Thr Phe Lys Arg Ala Lys Tyr Leu Arg
                485                 490                 495

Gln Lys Thr Tyr Ile Gln Asp Ile Tyr Met Lys Glu Val Asp Gly Lys
            500                 505                 510

Leu Val Glu Gly Ser Pro Asp Asp Tyr Thr Asp Ile Lys Phe Ser Val
            515                 520                 525

Lys Cys Ala Gly Met Thr Asp Lys Ile Lys Glu Val Thr Phe Glu
        530                 535                 540

Asn Phe Lys Val Gly Phe Ser Arg Lys Met Lys Pro Lys Pro Val Gln
545                 550                 555                 560

Val Pro Gly Gly Val Val Leu Val Asp Asp Thr Phe Thr Ile Lys
                565                 570                 575
```

<210> SEQ ID NO 3
<211> LENGTH: 572
<212> TYPE: PRT
<213> ORGANISM: Artificial Sequence
<220> FEATURE:
<223> OTHER INFORMATION: DNA polymerase mutant derived from WT phage PZA
      DNA polymerase

<400> SEQUENCE: 3

```
Met Pro Arg Lys Met Tyr Ser Cys Asp Phe Glu Thr Thr Thr Lys Val
 1               5                  10                  15

Glu Asp Cys Arg Val Trp Ala Tyr Gly Tyr Met Asn Ile Glu Asp His
             20                  25                  30

Ser Glu Tyr Lys Ile Gly Asn Ser Leu Asp Glu Phe Met Ala Trp Val
         35                  40                  45

Leu Lys Val Gln Ala Asp Leu Tyr Phe His Asp Leu Lys Phe Asp Gly
     50                  55                  60

Ala Phe Ile Ile Asn Trp Leu Glu Arg Asn Gly Phe Lys Trp Ser Ala
 65                  70                  75                  80

Asp Gly Leu Pro Asn Thr Tyr Asn Thr Ile Ile Ser Arg Met Gly Gln
                 85                  90                  95

Trp Tyr Met Ile Asp Ile Cys Leu Gly Tyr Lys Gly Lys Arg Lys Ile
            100                 105                 110

His Thr Val Ile Tyr Asp Ser Leu Lys Lys Leu Pro Phe Pro Val Lys
        115                 120                 125

Lys Ile Ala Lys Asp Phe Lys Leu Thr Val Leu Lys Gly Asp Ile Asp
    130                 135                 140

Tyr His Lys Glu Arg Pro Val Gly Tyr Glu Ile Thr Pro Asp Glu Tyr
145                 150                 155                 160

Ala Tyr Ile Lys Asn Asp Ile Gln Ile Ile Ala Glu Ala Leu Leu Ile
                165                 170                 175

Gln Phe Lys Gln Gly Leu Asp Arg Met Thr Ala Gly Ser Asp Asp Leu
            180                 185                 190

Lys Gly Phe Lys Asp Ile Ile Thr Thr Lys Lys Phe Lys Lys Val Phe
        195                 200                 205

Pro Thr Leu Ser Leu Gly Leu Asp Lys Glu Val Arg Tyr Ala Tyr Arg
    210                 215                 220

Gly Gly Phe Thr Trp Leu Asn Asp Arg Phe Lys Glu Lys Glu Ile Gly
225                 230                 235                 240

Glu Gly Met Val Phe Asp Val Asn Ser Leu Tyr Pro Ala Gln Met Tyr
                245                 250                 255

Ser Arg Leu Leu Pro Tyr Gly Glu Pro Ile Val Phe Glu Gly Lys Tyr
            260                 265                 270

Val Trp Asp Glu Asp Tyr Pro Leu His Ile Gln His Ile Arg Cys Glu
        275                 280                 285

Phe Glu Leu Lys Glu Gly Tyr Ile Pro Thr Ile Gln Ile Lys Arg Ser
    290                 295                 300

Arg Phe Tyr Lys Gly Asn Glu Tyr Leu Lys Ser Ser Gly Gly Glu Ile
305                 310                 315                 320

Ala Asp Leu Trp Val Ser Asn Val Asp Leu Glu Leu Met Lys Glu His
                325                 330                 335

Tyr Asp Leu Tyr Asn Val Glu Tyr Ile Ser Gly Leu Lys Phe Lys Ala
            340                 345                 350

Thr Thr Gly Leu Phe Lys Asp Phe Ile Asp Lys Trp Thr His Ile Lys
        355                 360                 365
```

```
Thr Thr Ser Glu Gly Ala Ile Lys Gln Leu Ala Lys Leu Met Leu Asn
    370                 375                 380

Ser Leu Tyr Gly Lys Phe Ala Ser Asn Pro Asp Val Thr Gly Lys Val
385                 390                 395                 400

Pro Tyr Leu Lys Glu Asn Gly Ala Leu Gly Phe Arg Leu Gly Glu Glu
                405                 410                 415

Glu Thr Lys Asp Pro Val Tyr Thr Pro Met Gly Val Phe Ile Thr Ala
            420                 425                 430

Trp Ala Arg Tyr Thr Thr Ile Thr Ala Ala Gln Ala Cys Phe Asp Arg
        435                 440                 445

Ile Ile Tyr Cys Asp Thr Asp Ser Ile His Leu Thr Gly Thr Glu Ile
    450                 455                 460

Pro Asp Val Ile Lys Asp Ile Val Asp Pro Lys Lys Leu Gly Tyr Trp
465                 470                 475                 480

Ala His Glu Ser Thr Phe Lys Arg Ala Lys Tyr Leu Arg Gln Lys Thr
                485                 490                 495

Tyr Ile Gln Asp Ile Tyr Met Lys Glu Val Asp Gly Lys Leu Val Glu
            500                 505                 510

Gly Ser Pro Asp Asp Tyr Thr Thr Ile Lys Phe Ser Val Lys Cys Ala
        515                 520                 525

Gly Met Thr Asp Lys Ile Lys Lys Glu Val Thr Phe Glu Asn Phe Lys
    530                 535                 540

Val Gly Phe Ser Arg Lys Met Lys Pro Lys Pro Val Gln Val Pro Gly
545                 550                 555                 560

Gly Val Val Leu Val Asp Asp Thr Phe Thr Ile Lys
                565                 570

<210> SEQ ID NO 4
<211> LENGTH: 593
<212> TYPE: PRT
<213> ORGANISM: Artificial Sequence
<220> FEATURE:
<223> OTHER INFORMATION: DNA polymerase mutant derived from WT phage
      B103 DNA polymerase

<400> SEQUENCE: 4

Met Pro Arg Lys Met Phe Ser Cys Asp Phe Glu Thr Thr Thr Lys Leu
1               5                   10                  15

Asp Asp Cys Arg Val Trp Ala Tyr Gly Tyr Met Glu Ile Gly Asn Leu
                20                  25                  30

Asp Asn Tyr Lys Ile Gly Asn Ser Leu Asp Glu Phe Met Gln Trp Val
            35                  40                  45

Met Glu Ile Gln Ala Asp Leu Tyr Phe His Asp Leu Lys Phe Asp Gly
        50                  55                  60

Ala Phe Ile Val Asn Trp Leu Glu His His Gly Phe Lys Trp Ser Asn
65                  70                  75                  80

Glu Gly Leu Pro Asn Thr Tyr Asn Thr Ile Ser Lys Met Gly Gln
                85                  90                  95

Trp Tyr Met Ile Asp Ile Cys Phe Gly Tyr Lys Gly Lys Arg Lys Leu
                100                 105                 110

His Thr Val Ile Tyr Asp Ser Leu Lys Lys Leu Pro Phe Pro Val Lys
            115                 120                 125

Lys Ile Ala Lys Asp Phe Gln Leu Pro Leu Leu Lys Gly Asp Ile Asp
130                 135                 140

Tyr His Ala Glu Arg Pro Val Gly His Glu Ile Thr Pro Glu Glu Tyr
```

```
            145                 150                 155                 160
Glu Tyr Ile Lys Asn Asp Ile Glu Ile Ile Ala Arg Ala Leu Asp Ile
                165                 170                 175
Gln Phe Lys Gln Gly Leu Asp Arg Met Thr Ala Gly Ser Asp Ser Leu
                180                 185                 190
Lys Gly Phe Lys Asp Ile Leu Ser Thr Lys Lys Phe Asn Lys Val Phe
                195                 200                 205
Pro Lys Leu Ser Leu Pro Met Asp Lys Glu Ile Arg Arg Ala Tyr Arg
            210                 215                 220
Gly Gly Phe Thr Trp Leu Asn Asp Lys Tyr Lys Glu Lys Ile Gly
225                 230                 235                 240
Glu Gly Met Val Phe Asp Val Asn Ser Leu Tyr Pro Ser Gln Met Tyr
                245                 250                 255
Ser Arg Pro Leu Pro Tyr Gly Ala Pro Ile Val Phe Gln Gly Lys Tyr
                260                 265                 270
Glu Lys Asp Glu Gln Tyr Pro Leu Tyr Ile Gln Arg Ile Arg Phe Glu
            275                 280                 285
Phe Glu Leu Lys Glu Gly Tyr Ile Pro Thr Ile Gln Ile Lys Lys Asn
            290                 295                 300
Pro Phe Phe Lys Gly Asn Glu Tyr Leu Lys Asn Ser Gly Ala Glu Pro
305                 310                 315                 320
Val Glu Leu Tyr Leu Thr Asn Val Asp Leu Glu Leu Ile Gln Glu His
                325                 330                 335
Tyr Glu Met Tyr Asn Val Glu Tyr Ile Asp Gly Phe Lys Phe Arg Glu
                340                 345                 350
Lys Thr Gly Leu Phe Lys Glu Phe Ile Asp Lys Trp Thr Tyr Val Lys
                355                 360                 365
Thr His Glu Lys Gly Ala Lys Lys Gln Leu Ala Lys Leu Met Phe Asp
            370                 375                 380
Ser Leu Tyr Gly Lys Phe Ala Ser Asn Pro Asp Val Thr Gly Lys Val
385                 390                 395                 400
Pro Tyr Leu Lys Glu Asp Gly Ser Leu Gly Phe Arg Val Gly Asp Glu
                405                 410                 415
Glu Tyr Lys Asp Pro Val Tyr Thr Pro Met Gly Val Phe Ile Thr Ala
                420                 425                 430
Trp Ala Arg Phe Thr Thr Ile Thr Ala Ala Gln Ala Cys Tyr Asp Arg
                435                 440                 445
Ile Ile Tyr Cys Asp Thr Asp Ser Ile His Leu Thr Gly Thr Glu Val
            450                 455                 460
Pro Glu Ile Ile Lys Asp Ile Val Asp Pro Lys Lys Leu Gly Tyr Trp
465                 470                 475                 480
Ala His Glu Ser Thr Phe Lys Arg Ala Lys Tyr Leu Arg Gln Lys Thr
                485                 490                 495
Tyr Ile Gln Asp Ile Tyr Ala Lys Glu Val Asp Gly Lys Leu Ile Glu
            500                 505                 510
Cys Ser Pro Asp Glu Ala Thr Thr Thr Lys Phe Ser Val Lys Cys Ala
            515                 520                 525
Gly Met Thr Asp Thr Ile Lys Lys Lys Val Thr Phe Asp Asn Phe Arg
            530                 535                 540
Val Gly Phe Ser Ser Thr Gly Lys Pro Lys Pro Val Gln Val Asn Gly
545                 550                 555                 560
Gly Val Val Leu Val Asp Ser Val Phe Thr Ile Lys Lys Pro Lys Pro
                565                 570                 575
```

```
Val Gln Val Asn Gly Gly Val Val Leu Val Asp Ser Val Phe Thr Ile
            580                 585                 590

Lys

<210> SEQ ID NO 5
<211> LENGTH: 572
<212> TYPE: PRT
<213> ORGANISM: Artificial Sequence
<220> FEATURE:
<223> OTHER INFORMATION: DNA polymerase mutant derived from WT phage M2
      DNA polymerase

<400> SEQUENCE: 5

Met Ser Arg Lys Met Phe Ser Cys Asp Phe Glu Thr Thr Thr Lys Leu
1               5                   10                  15

Asp Asp Cys Arg Val Trp Ala Tyr Gly Tyr Met Glu Ile Gly Asn Leu
            20                  25                  30

Asp Asn Tyr Lys Ile Gly Asn Ser Leu Asp Glu Phe Met Gln Trp Val
        35                  40                  45

Met Glu Ile Gln Ala Asp Leu Tyr Phe His Asp Leu Lys Phe Asp Gly
    50                  55                  60

Ala Phe Ile Val Asn Trp Leu Glu Gln His Gly Phe Lys Trp Ser Asn
65                  70                  75                  80

Glu Gly Leu Pro Asn Thr Tyr Asn Thr Ile Ile Ser Lys Met Gly Gln
                85                  90                  95

Trp Tyr Met Ile Asp Ile Cys Phe Gly Tyr Lys Gly Lys Arg Lys Leu
            100                 105                 110

His Thr Val Ile Tyr Asp Ser Leu Lys Lys Leu Pro Phe Pro Val Lys
        115                 120                 125

Lys Ile Ala Lys Asp Phe Gln Leu Pro Leu Leu Lys Gly Asp Ile Asp
    130                 135                 140

Tyr His Thr Glu Arg Pro Val Gly His Glu Ile Thr Pro Glu Glu Tyr
145                 150                 155                 160

Glu Tyr Ile Lys Asn Asp Ile Glu Ile Ile Ala Arg Ala Leu Asp Ile
                165                 170                 175

Gln Phe Lys Gln Gly Leu Asp Arg Met Thr Ala Gly Ser Asp Ser Leu
            180                 185                 190

Lys Gly Phe Lys Asp Ile Leu Ser Thr Lys Lys Phe Asn Lys Val Phe
        195                 200                 205

Pro Lys Leu Ser Leu Pro Met Asp Lys Glu Ile Arg Lys Ala Tyr Arg
    210                 215                 220

Gly Gly Phe Thr Trp Leu Asn Asp Lys Tyr Lys Glu Lys Glu Ile Gly
225                 230                 235                 240

Glu Gly Met Val Phe Asp Val Asn Ser Leu Tyr Pro Ser Gln Met Tyr
                245                 250                 255

Ser Arg Pro Leu Pro Tyr Gly Ala Pro Ile Val Phe Gln Gly Lys Tyr
            260                 265                 270

Glu Lys Asp Glu Gln Tyr Pro Leu Tyr Ile Gln Arg Ile Arg Phe Glu
        275                 280                 285

Phe Glu Leu Lys Glu Gly Tyr Ile Pro Thr Ile Gln Ile Lys Lys Asn
    290                 295                 300

Pro Phe Phe Lys Gly Asn Glu Tyr Leu Lys Asn Ser Gly Val Glu Pro
305                 310                 315                 320

Val Glu Leu Tyr Leu Thr Asn Val Asp Leu Glu Leu Ile Gln Glu His
                325                 330                 335
```

```
Tyr Glu Leu Tyr Asn Val Glu Tyr Ile Asp Gly Phe Lys Phe Arg Glu
                340                 345                 350

Lys Thr Gly Leu Phe Lys Asp Phe Ile Asp Lys Trp Thr Tyr Val Lys
            355                 360                 365

Thr His Glu Glu Gly Ala Lys Lys Gln Leu Ala Lys Leu Met Leu Asn
        370                 375                 380

Ser Leu Tyr Gly Lys Phe Ala Ser Asn Pro Asp Val Thr Gly Lys Val
385                 390                 395                 400

Pro Tyr Leu Lys Asp Asp Gly Ser Leu Gly Phe Arg Val Gly Asp Glu
                405                 410                 415

Glu Tyr Lys Asp Pro Val Tyr Thr Pro Met Gly Val Phe Ile Thr Ala
            420                 425                 430

Trp Ala Arg Phe Thr Thr Ile Thr Ala Ala Gln Ala Cys Tyr Asp Arg
        435                 440                 445

Ile Ile Tyr Cys Asp Thr Asp Ser Ile His Leu Thr Gly Thr Glu Val
450                 455                 460

Pro Glu Ile Ile Lys Asp Ile Val Asp Pro Lys Lys Leu Gly Tyr Trp
465                 470                 475                 480

Ala His Glu Ser Thr Phe Lys Arg Ala Lys Tyr Leu Arg Gln Lys Thr
                485                 490                 495

Tyr Ile Gln Asp Ile Tyr Val Lys Glu Val Asp Gly Lys Leu Lys Glu
            500                 505                 510

Cys Ser Pro Asp Glu Ala Thr Thr Thr Lys Phe Ser Val Lys Cys Ala
        515                 520                 525

Gly Met Thr Asp Thr Ile Lys Lys Val Thr Phe Asp Asn Phe Ala
530                 535                 540

Val Gly Phe Ser Ser Met Gly Lys Pro Lys Pro Val Gln Val Asn Gly
545                 550                 555                 560

Gly Val Val Leu Val Asp Ser Val Phe Thr Ile Lys
                565                 570

<210> SEQ ID NO 6
<211> LENGTH: 578
<212> TYPE: PRT
<213> ORGANISM: Artificial Sequence
<220> FEATURE:
<223> OTHER INFORMATION: DNA polymerase mutant derived from WT phage GA1
      DNA polymerase

<400> SEQUENCE: 6

Met Ala Arg Ser Val Tyr Val Cys Asp Phe Glu Thr Thr Thr Asp Pro
1               5                   10                  15

Glu Asp Cys Arg Leu Trp Ala Trp Gly Trp Met Asp Ile Tyr Asn Thr
            20                  25                  30

Asp Lys Trp Ser Tyr Gly Glu Asp Ile Asp Ser Phe Met Glu Trp Ala
        35                  40                  45

Leu Asn Ser Asn Ser Asp Ile Tyr Phe His Asp Leu Lys Phe Asp Gly
    50                  55                  60

Ser Phe Ile Leu Pro Trp Trp Leu Arg Asn Gly Tyr Val His Thr Glu
65                  70                  75                  80

Glu Asp Arg Thr Asn Thr Pro Lys Glu Phe Thr Thr Ile Ser Gly
                85                  90                  95

Met Gly Gln Trp Tyr Ala Val Asp Val Cys Ile Asn Thr Arg Gly Lys
            100                 105                 110

Asn Lys Asn His Val Val Phe Tyr Asp Ser Leu Lys Lys Leu Pro Phe
```

```
            115                 120                 125
Lys Val Glu Gln Ile Ala Lys Gly Phe Gly Leu Pro Val Leu Lys Gly
    130                 135                 140

Asp Ile Asp Tyr Lys Lys Tyr Arg Pro Val Gly Tyr Val Met Asp Asp
145                 150                 155                 160

Asn Glu Ile Glu Tyr Leu Lys His Asp Leu Leu Ile Val Ala Leu Ala
                165                 170                 175

Leu Arg Ser Met Phe Asp Asn Asp Phe Thr Ser Met Thr Val Gly Ser
            180                 185                 190

Asp Ala Leu Asn Thr Tyr Lys Glu Met Leu Gly Val Lys Gln Trp Glu
        195                 200                 205

Lys Tyr Phe Pro Val Leu Ser Leu Lys Val Asn Ser Glu Ile Arg Lys
    210                 215                 220

Ala Tyr Lys Gly Gly Phe Thr Trp Val Asn Pro Lys Tyr Gln Gly Glu
225                 230                 235                 240

Thr Val Tyr Gly Gly Met Val Phe Asp Val Asn Ser Met Tyr Pro Ala
                245                 250                 255

Met Met Lys Asn Lys Leu Leu Pro Tyr Gly Glu Pro Val Met Phe Lys
            260                 265                 270

Gly Glu Tyr Lys Lys Asn Val Glu Tyr Pro Leu Tyr Ile Gln Gln Val
        275                 280                 285

Arg Cys Phe Phe Glu Leu Lys Lys Asp Lys Ile Pro Cys Ile Gln Ile
    290                 295                 300

Lys Gly Asn Ala Arg Phe Gly Gln Asn Glu Tyr Leu Ser Thr Ser Gly
305                 310                 315                 320

Asp Glu Tyr Val Asp Leu Tyr Val Thr Asn Val Asp Trp Glu Leu Ile
                325                 330                 335

Lys Lys His Tyr Asp Ile Phe Glu Glu Glu Phe Ile Gly Gly Phe Met
            340                 345                 350

Phe Lys Gly Phe Ile Gly Phe Phe Asp Glu Tyr Ile Asp Arg Phe Met
        355                 360                 365

Glu Ile Lys Asn Ser Pro Asp Ser Ser Ala Glu Gln Ser Leu Gln Ala
    370                 375                 380

Lys Leu Met Leu Asn Ser Leu Tyr Gly Lys Phe Ala Thr Asn Pro Asp
385                 390                 395                 400

Ile Thr Gly Lys Val Pro Tyr Leu Asp Glu Asn Gly Val Leu Lys Phe
                405                 410                 415

Arg Lys Gly Glu Leu Lys Glu Arg Asp Pro Val Tyr Thr Pro Met Gly
            420                 425                 430

Cys Phe Ile Thr Ala Tyr Ala Arg Glu Asn Ile Leu Ser Asn Ala Gln
        435                 440                 445

Lys Leu Tyr Pro Arg Phe Ile Tyr Ala Asp Thr Asp Ser Ile His Val
    450                 455                 460

Glu Gly Leu Gly Glu Val Asp Ala Ile Lys Asp Val Ile Asp Pro Lys
465                 470                 475                 480

Lys Leu Gly Tyr Trp Asp His Glu Ala Thr Phe Gln Arg Ala Arg Tyr
                485                 490                 495

Val Arg Gln Lys Thr Tyr Phe Ile Glu Thr Thr Trp Lys Glu Asn Asp
            500                 505                 510

Lys Gly Lys Leu Val Val Cys Glu Pro Gln Asp Ala Thr Lys Val Lys
        515                 520                 525

Pro Lys Ile Ala Cys Ala Gly Met Ser Asp Ala Ile Lys Glu Arg Ile
    530                 535                 540
```

```
Arg Phe Asn Glu Phe Lys Ile Gly Tyr Ser Thr His Gly Ser Leu Lys
545                 550                 555                 560

Pro Lys Asn Val Leu Gly Gly Val Val Leu Met Asp Tyr Pro Phe Ala
                565                 570                 575

Ile Lys

<210> SEQ ID NO 7
<211> LENGTH: 575
<212> TYPE: PRT
<213> ORGANISM: Artificial Sequence
<220> FEATURE:
<223> OTHER INFORMATION: DNA polymerase mutant 587P.  Derived from WT
      phage phi29 DNA polymerase (SEQ ID NO: 1)

<400> SEQUENCE: 7

Met Lys His Met Pro Arg Lys Met Tyr Ser Cys Asp Phe Glu Thr Thr
1               5                   10                  15

Thr Lys Val Glu Asp Cys Arg Val Trp Ala Tyr Gly Tyr Met Asn Ile
            20                  25                  30

Glu Asp His Ser Glu Tyr Lys Ile Gly Asn Ser Leu Asp Glu Phe Met
        35                  40                  45

Ala Trp Val Leu Lys Val Gln Ala Asp Leu Tyr Phe His Asp Leu Lys
    50                  55                  60

Phe Asp Gly Ala Phe Ile Ile Asn Trp Leu Glu Arg Asn Gly Phe Lys
65                  70                  75                  80

Trp Ser Ala Asp Gly Leu Pro Asn Thr Tyr Asn Thr Ile Ile Ser Arg
                85                  90                  95

Met Gly Gln Trp Tyr Met Ile Asp Ile Cys Leu Gly Tyr Lys Gly Lys
            100                 105                 110

Arg Lys Ile His Thr Val Ile Tyr Asp Ser Leu Lys Lys Leu Pro Phe
        115                 120                 125

Pro Val Lys Lys Ile Ala Lys Asp Phe Lys Leu Thr Val Leu Lys Gly
    130                 135                 140

Asp Ile Asp Tyr His Lys Glu Arg Pro Val Gly Tyr Lys Ile Thr Pro
145                 150                 155                 160

Glu Glu Tyr Ala Tyr Ile Lys Asn Asp Ile Gln Ile Ile Ala Glu Ala
                165                 170                 175

Leu Leu Ile Gln Phe Lys Gln Gly Leu Asp Arg Met Thr Ala Gly Ser
            180                 185                 190

Asp Ser Leu Lys Gly Phe Lys Asp Ile Ile Thr Thr Lys Lys Phe Lys
        195                 200                 205

Lys Val Phe Pro Thr Leu Ser Leu Gly Leu Asp Lys Glu Val Arg Tyr
    210                 215                 220

Ala Tyr Arg Gly Gly Phe Thr Trp Leu Asn Asp Arg Phe Lys Glu Lys
225                 230                 235                 240

Glu Ile Gly Glu Gly Met Val Phe Asp Val Asn Ser Leu Tyr Pro Ala
                245                 250                 255

Gln Met Tyr Ser Arg Leu Leu Pro Tyr Gly Glu Pro Ile Val Phe Glu
            260                 265                 270

Gly Lys Tyr Val Trp Asp Glu Asp Tyr Pro Leu His Ile Gln His Ile
        275                 280                 285

Arg Cys Glu Phe Glu Leu Lys Glu Gly Tyr Ile Pro Thr Ile Gln Ile
    290                 295                 300

Lys Arg Ser Arg Phe Tyr Lys Gly Asn Glu Tyr Leu Lys Ser Ser Gly
305                 310                 315                 320
```

```
Gly Glu Ile Ala Asp Leu Trp Leu Ser Asn Val Asp Leu Glu Leu Met
                325                 330                 335

Lys Glu His Tyr Asp Leu Tyr Asn Val Glu Tyr Ile Ser Gly Leu Lys
            340                 345                 350

Phe Lys Ala Thr Thr Gly Leu Phe Lys Asp Phe Ile Asp Lys Trp Thr
        355                 360                 365

Tyr Ile Lys Thr Thr Ser Glu Gly Ala Ile Lys Gln Leu Ala Lys Leu
    370                 375                 380

Met Leu Asn Ser Leu Tyr Gly Lys Phe Ala Ser Asn Pro Asp Val Thr
385                 390                 395                 400

Gly Lys Val Pro Tyr Leu Lys Glu Asn Gly Ala Leu Gly Phe Arg Leu
                405                 410                 415

Gly Glu Glu Thr Lys Asp Pro Val Tyr Thr Pro Met Gly Val Phe
            420                 425                 430

Ile Thr Ala Trp Ala Arg Tyr Thr Thr Ile Thr Ala Ala Gln Ala Cys
        435                 440                 445

Tyr Asp Arg Ile Ile Tyr Cys Asp Thr Asp Ser Ile His Leu Thr Gly
    450                 455                 460

Thr Glu Ile Pro Asp Val Ile Lys Asp Ile Val Asp Pro Lys Lys Leu
465                 470                 475                 480

Gly Tyr Ser Ala His Glu Ser Thr Phe Lys Arg Ala Lys Tyr Leu Arg
                485                 490                 495

Gln Lys Thr Tyr Ile Gln Asp Ile Tyr Met Lys Glu Val Asp Gly Lys
            500                 505                 510

Leu Val Glu Gly Ser Pro Asp Asp Tyr Thr Asp Ile Lys Phe Ser Val
        515                 520                 525

Lys Cys Ala Gly Met Thr Asp Lys Ile Lys Lys Glu Val Thr Phe Glu
    530                 535                 540

Asn Phe Lys Val Gly Phe Ser Arg Lys Met Lys Pro Lys Pro Val Gln
545                 550                 555                 560

Val Pro Gly Gly Val Val Leu Val Asp Asp Thr Phe Thr Ile Lys
                565                 570                 575

<210> SEQ ID NO 8
<211> LENGTH: 575
<212> TYPE: PRT
<213> ORGANISM: Artificial Sequence
<220> FEATURE:
<223> OTHER INFORMATION: DNA polymerase mutant 596P.  Derived from WT
      phage phi29 DNA polymerase (SEQ ID NO: 1)

<400> SEQUENCE: 8

Met Lys His Met Pro Arg Lys Met Tyr Ser Cys Asp Phe Glu Thr Thr
1               5                   10                  15

Thr Lys Val Glu Asp Cys Arg Val Trp Ala Tyr Gly Tyr Met Asn Ile
            20                  25                  30

Glu Asp His Ser Glu Tyr Lys Ile Gly Asn Ser Leu Asp Glu Phe Met
        35                  40                  45

Ala Trp Val Leu Lys Val Gln Ala Asp Leu Tyr Phe His Asp Leu Lys
    50                  55                  60

Phe Asp Gly Ala Phe Ile Ile Asn Trp Leu Glu Arg Asn Gly Phe Lys
65                  70                  75                  80

Trp Ser Ala Asp Gly Leu Pro Asn Thr Tyr Asn Thr Ile Ile Ser Arg
                85                  90                  95

Met Gly Gln Trp Tyr Met Ile Asp Ile Cys Leu Gly Tyr Lys Gly Lys
```

```
                100             105             110
Arg Lys Ile His Thr Val Ile Tyr Asp Ser Leu Lys Lys Leu Pro Phe
            115                 120             125
Pro Val Lys Lys Ile Ala Lys Asp Phe Lys Leu Thr Val Leu Lys Gly
        130                 135             140
Asp Ile Asp Tyr His Lys Glu Arg Pro Val Gly Tyr Lys Ile Thr Pro
145                 150             155                 160
Glu Glu Tyr Ala Tyr Ile Lys Asn Asp Ile Gln Ile Ile Ala Glu Ala
                165             170             175
Leu Leu Ile Gln Phe Lys Gln Gly Leu Asp Arg Met Thr Ala Gly Ser
            180             185             190
Asp Ser Leu Lys Gly Phe Lys Asp Ile Ile Thr Thr Lys Lys Phe Lys
        195             200             205
Lys Val Phe Pro Thr Leu Ser Leu Gly Leu Asp Lys Glu Val Arg Tyr
    210             215             220
Ala Tyr Arg Gly Gly Phe Thr Trp Leu Asn Asp Arg Phe Lys Glu Lys
225             230             235             240
Glu Ile Gly Glu Gly Met Val Phe Asp Val Asn Ser Leu Tyr Pro Ala
                245             250             255
Gln Met Tyr Ser Arg Leu Leu Pro Tyr Gly Glu Pro Ile Val Phe Glu
            260             265             270
Gly Lys Tyr Val Trp Asp Glu Asp Tyr Pro Leu His Ile Gln His Ile
        275             280             285
Arg Cys Glu Phe Glu Leu Lys Glu Gly Tyr Ile Pro Thr Ile Gln Ile
    290             295             300
Lys Arg Ser Arg Phe Tyr Lys Gly Asn Glu Tyr Leu Lys Ser Ser Gly
305             310             315             320
Gly Glu Ile Ala Asp Leu Trp Leu Ser Asn Val Asp Leu Glu Leu Met
                325             330             335
Lys Glu His Tyr Asp Leu Tyr Asn Val Glu Tyr Ile Ser Gly Leu Lys
            340             345             350
Phe Lys Ala Thr Thr Gly Leu Phe Lys Asp Phe Ile Asp Lys Trp Thr
        355             360             365
Tyr Ile Lys Thr Thr Ser Glu Gly Ala Ile Lys Gln Leu Ala Lys Leu
    370             375             380
Met Leu Asn Ser Leu Tyr Gly Lys Phe Ala Ser Asn Pro Asp Val Thr
385             390             395             400
Gly Lys Val Pro Tyr Leu Lys Glu Asn Gly Ala Leu Gly Phe Arg Leu
                405             410             415
Gly Glu Glu Glu Thr Lys Asp Pro Val Tyr Thr Pro Met Gly Val Phe
            420             425             430
Ile Thr Ala Trp Ala Arg Tyr Thr Thr Ile Thr Ala Ala Gln Ala Cys
        435             440             445
Tyr Asp Arg Ile Ile Tyr Cys Asp Thr Asp Ser Ile His Leu Thr Gly
    450             455             460
Thr Glu Ile Pro Asp Val Ile Lys Asp Ile Val Asp Pro Lys Lys Leu
465             470             475             480
Gly Tyr Trp Ala His Glu Ser Thr Phe Lys Arg Ala Lys Tyr Leu Arg
                485             490             495
Gln Lys Thr Tyr Ile Gln Asp Ile Tyr Met Lys Glu Val Asp Gly Lys
            500             505             510
Leu Val Glu Gly Ser Pro Asp Asp Tyr Thr Asp Ile Lys Leu Ser Val
        515             520             525
```

```
Lys Cys Ala Gly Met Thr Asp Lys Ile Lys Lys Glu Val Thr Phe Glu
            530                 535                 540

Asn Phe Lys Val Gly Phe Ser Arg Lys Met Lys Pro Lys Pro Val Gln
545                 550                 555                 560

Val Pro Gly Gly Val Val Leu Val Asp Asp Thr Phe Thr Ile Lys
                565                 570                 575

<210> SEQ ID NO 9
<211> LENGTH: 577
<212> TYPE: PRT
<213> ORGANISM: Artificial Sequence
<220> FEATURE:
<223> OTHER INFORMATION: Chimeric DNA polymerase mutant 604P.  Derived
      from the polymerases encoded by SEQ ID NOs: 2-6.

<400> SEQUENCE: 9

Met Lys His Met Pro Arg Lys Met Tyr Ser Cys Asp Phe Glu Thr Thr
1               5                   10                  15

Thr Lys Val Glu Asp Cys Arg Val Trp Ala Tyr Gly Tyr Met Asn Ile
            20                  25                  30

Glu Asp His Ser Glu Tyr Lys Ile Gly Asn Ser Leu Asp Glu Phe Met
        35                  40                  45

Ala Trp Val Leu Lys Val Gln Ala Asp Leu Tyr Phe His Asp Leu Lys
    50                  55                  60

Phe Asp Gly Ala Phe Ile Ile Asn Trp Leu Glu Arg Asn Gly Phe Lys
65                  70                  75                  80

Trp Ser Ala Asp Gly Leu Pro Asn Thr Tyr Asn Thr Ile Ile Ser Arg
                85                  90                  95

Met Gly Gln Trp Tyr Met Ile Asp Ile Cys Leu Gly Tyr Lys Gly Lys
            100                 105                 110

Arg Lys Ile His Thr Val Ile Tyr Asp Ser Leu Lys Lys Leu Pro Phe
        115                 120                 125

Pro Val Lys Lys Ile Ala Lys Asp Phe Gln Leu Pro Leu Leu Lys Gly
    130                 135                 140

Asp Ile Asp Tyr His Ala Glu Arg Pro Val Gly His Glu Ile Thr Pro
145                 150                 155                 160

Glu Glu Tyr Glu Tyr Ile Lys Asn Asp Ile Glu Ile Ile Ala Arg Ala
                165                 170                 175

Leu Asp Ile Gln Phe Lys Gln Gly Leu Asp Arg Met Thr Ala Gly Ser
            180                 185                 190

Asp Ser Leu Lys Gly Phe Lys Asp Ile Leu Ser Thr Lys Lys Phe Asn
        195                 200                 205

Lys Val Phe Pro Lys Leu Ser Leu Pro Met Asp Lys Glu Ile Arg Arg
    210                 215                 220

Ala Tyr Arg Gly Gly Phe Thr Trp Leu Asn Asp Lys Tyr Lys Glu Lys
225                 230                 235                 240

Glu Ile Gly Glu Gly Met Val Phe Asp Val Asn Ser Met Tyr Pro Ala
                245                 250                 255

Met Met Lys Asn Lys Leu Leu Pro Tyr Gly Glu Pro Val Met Phe Lys
            260                 265                 270

Gly Glu Tyr Lys Lys Asn Val Glu Tyr Pro Leu Tyr Ile Gln Gln Val
        275                 280                 285

Arg Cys Phe Phe Glu Leu Lys Lys Asp Lys Ile Pro Cys Ile Gln Ile
    290                 295                 300

Lys Gly Asn Ala Arg Phe Gly Gln Asn Glu Tyr Leu Ser Thr Ser Gly
```

```
305                 310                 315                 320
Asp Glu Tyr Val Asp Leu Tyr Val Thr Asn Val Asp Trp Glu Leu Ile
                325                 330                 335
Lys Lys His Tyr Asp Ile Phe Glu Glu Phe Ile Gly Gly Phe Met
                340                 345                 350
Phe Lys Gly Phe Ile Gly Phe Asp Glu Tyr Ile Asp Arg Phe Met
                355                 360                 365
Glu Ile Lys Asn Ser Pro Asp Ser Ser Ala Glu Gln Ser Leu Gln Ala
        370                 375                 380
Lys Leu Met Leu Asn Ser Leu Tyr Gly Lys Phe Ala Thr Asn Pro Asp
385                 390                 395                 400
Val Thr Gly Lys Val Pro Tyr Leu Lys Glu Asn Gly Ala Leu Gly Phe
                405                 410                 415
Arg Leu Gly Glu Glu Thr Lys Asp Pro Val Tyr Thr Pro Met Gly
                420                 425                 430
Val Phe Ile Thr Ala Trp Ala Arg Phe Thr Thr Ile Thr Ala Ala Gln
                435                 440                 445
Ala Cys Tyr Asp Arg Ile Ile Tyr Cys Asp Thr Asp Ser Ile His Leu
        450                 455                 460
Thr Gly Thr Glu Val Pro Glu Ile Ile Lys Asp Ile Val Asp Pro Lys
465                 470                 475                 480
Lys Leu Gly Tyr Trp Ala His Glu Ser Thr Phe Lys Arg Ala Lys Tyr
                485                 490                 495
Leu Arg Gln Lys Thr Tyr Ile Gln Asp Ile Tyr Val Lys Glu Val Asp
                500                 505                 510
Gly Lys Leu Lys Glu Cys Ser Pro Asp Glu Ala Thr Thr Lys Phe
        515                 520                 525
Ser Val Lys Cys Ala Gly Met Thr Asp Thr Ile Lys Lys Val Thr
                530                 535                 540
Phe Asp Asn Phe Arg Val Gly Phe Ser Ser Thr Gly Lys Pro Lys Pro
545                 550                 555                 560
Val Gln Val Asn Gly Gly Val Val Leu Val Asp Ser Val Phe Thr Ile
                565                 570                 575
Lys

<210> SEQ ID NO 10
<211> LENGTH: 572
<212> TYPE: PRT
<213> ORGANISM: Artificial Sequence
<220> FEATURE:
<223> OTHER INFORMATION: Chimeric DNA polymerase mutant 605P.  Derived
      from the polymerases encoded by SEQ ID NOs: 2-6.

<400> SEQUENCE: 10

Met Ala Arg Ser Val Tyr Val Cys Asp Phe Glu Thr Thr Thr Asp Pro
1               5                   10                  15
Glu Asp Cys Arg Leu Trp Ala Trp Gly Trp Met Asp Ile Tyr Asn Thr
                20                  25                  30
Asp Lys Trp Ser Tyr Gly Glu Asp Ile Asp Ser Phe Met Glu Trp Ala
        35                  40                  45
Leu Asn Ser Asn Ser Asp Ile Tyr Phe His Asp Leu Lys Phe Asp Gly
        50                  55                  60
Ala Phe Ile Ile Asn Trp Leu Glu Arg Asn Gly Phe Lys Trp Ser Ala
65                  70                  75                  80
Asp Gly Leu Pro Asn Thr Tyr Asn Thr Ile Ile Ser Arg Met Gly Gln
```

```
                    85                  90                  95
Trp Tyr Met Ile Asp Ile Cys Leu Gly Tyr Lys Gly Lys Arg Lys Ile
                    100                 105                 110
His Thr Val Ile Tyr Asp Ser Leu Lys Lys Leu Pro Phe Lys Val Glu
                    115                 120                 125
Gln Ile Ala Lys Gly Phe Gly Leu Pro Val Leu Lys Gly Asp Ile Asp
            130                 135                 140
Tyr Lys Lys Tyr Arg Pro Val Gly Tyr Val Met Asp Asp Asn Glu Ile
145                 150                 155                 160
Glu Tyr Leu Lys His Asp Leu Leu Ile Val Ala Leu Ala Leu Arg Ser
                    165                 170                 175
Met Phe Asp Asn Asp Phe Thr Ser Met Thr Val Gly Ser Asp Ala Leu
                    180                 185                 190
Asn Thr Tyr Lys Glu Met Leu Gly Val Lys Gln Trp Glu Lys Tyr Phe
                    195                 200                 205
Pro Val Leu Ser Leu Lys Val Asn Ser Glu Ile Arg Lys Ala Tyr Lys
            210                 215                 220
Gly Gly Phe Thr Trp Val Asn Pro Lys Tyr Gln Gly Glu Thr Val Tyr
225                 230                 235                 240
Gly Gly Met Val Phe Asp Val Asn Ser Leu Tyr Pro Ala Gln Met Tyr
                    245                 250                 255
Ser Arg Leu Leu Pro Tyr Gly Glu Pro Ile Val Phe Gly Lys Tyr
                    260                 265                 270
Val Trp Asp Glu Asp Tyr Pro Leu His Ile Gln His Ile Arg Cys Glu
                    275                 280                 285
Phe Glu Leu Lys Glu Gly Tyr Ile Pro Thr Ile Gln Ile Lys Arg Ser
            290                 295                 300
Arg Phe Tyr Lys Gly Asn Glu Tyr Leu Lys Ser Ser Gly Gly Glu Ile
305                 310                 315                 320
Ala Asp Leu Trp Leu Ser Asn Val Asp Leu Glu Leu Met Lys Glu His
                    325                 330                 335
Tyr Asp Leu Tyr Asn Val Glu Tyr Ile Ser Gly Leu Lys Phe Lys Ala
                    340                 345                 350
Thr Thr Gly Leu Phe Lys Asp Phe Ile Asp Lys Trp Thr Tyr Ile Lys
                    355                 360                 365
Thr Thr Ser Glu Gly Ala Ile Lys Gln Leu Ala Lys Leu Met Leu Asn
            370                 375                 380
Ser Leu Tyr Gly Lys Phe Ala Ser Asn Pro Asp Val Thr Gly Lys Val
385                 390                 395                 400
Pro Tyr Leu Lys Glu Asp Gly Ser Leu Gly Phe Arg Val Gly Asp Glu
                    405                 410                 415
Glu Tyr Lys Asp Pro Val Tyr Thr Pro Met Gly Val Phe Ile Thr Ala
                    420                 425                 430
Trp Ala Arg Phe Thr Thr Ile Thr Ala Ala Gln Ala Cys Tyr Asp Arg
                    435                 440                 445
Ile Ile Tyr Cys Asp Thr Asp Ser Ile His Leu Thr Gly Thr Glu Val
            450                 455                 460
Pro Glu Ile Ile Lys Asp Ile Val Asp Pro Lys Lys Leu Gly Tyr Trp
465                 470                 475                 480
Ala His Glu Ser Thr Phe Lys Arg Ala Lys Tyr Leu Arg Gln Lys Thr
                    485                 490                 495
Tyr Ile Gln Asp Ile Tyr Ala Lys Glu Val Asp Gly Lys Leu Ile Glu
                    500                 505                 510
```

```
Cys Ser Pro Asp Glu Ala Thr Thr Thr Lys Phe Ser Val Lys Cys Ala
        515                 520                 525

Gly Met Thr Asp Thr Ile Lys Lys Val Thr Phe Asp Asn Phe Arg
    530                 535                 540

Val Gly Phe Ser Ser Thr Gly Lys Pro Lys Pro Val Gln Val Asn Gly
545                 550                 555                 560

Gly Val Val Leu Val Asp Ser Val Phe Thr Ile Lys
                565                 570
```

<210> SEQ ID NO 11
<211> LENGTH: 577
<212> TYPE: PRT
<213> ORGANISM: Artificial Sequence
<220> FEATURE:
<223> OTHER INFORMATION: Chimeric DNA polymerase mutant 1093P.  Derived
      from the polymerases encoded by SEQ ID NOs: 2-6.

<400> SEQUENCE: 11

```
Met Lys His Met Pro Arg Lys Met Tyr Ser Cys Asp Phe Glu Thr Thr
1               5                   10                  15

Thr Lys Val Glu Asp Cys Arg Val Trp Ala Tyr Gly Tyr Met Asn Ile
            20                  25                  30

Glu Asp His Ser Glu Tyr Lys Ile Gly Asn Ser Leu Asp Glu Phe Met
        35                  40                  45

Ala Trp Val Leu Lys Val Gln Ala Asp Leu Tyr Phe His Asp Leu Lys
    50                  55                  60

Phe Asp Gly Ala Phe Ile Ile Asn Trp Leu Glu Arg Asn Gly Phe Lys
65                  70                  75                  80

Trp Ser Ala Asp Gly Leu Pro Asn Thr Tyr Asn Thr Ile Ile Ser Arg
                85                  90                  95

Met Gly Gln Trp Tyr Met Ile Asp Ile Cys Leu Gly Tyr Lys Gly Lys
            100                 105                 110

Arg Lys Ile His Thr Val Ile Tyr Asp Ser Leu Lys Lys Leu Pro Phe
        115                 120                 125

Pro Val Lys Lys Ile Ala Lys Asp Phe Gln Leu Pro Leu Leu Lys Gly
    130                 135                 140

Asp Ile Asp Tyr His Ala Glu Arg Pro Val Gly His Glu Ile Thr Pro
145                 150                 155                 160

Glu Glu Tyr Glu Tyr Ile Lys Asn Asp Ile Glu Ile Ala Arg Ala
                165                 170                 175

Leu Asp Ile Gln Phe Lys Gln Gly Leu Asp Arg Met Thr Ala Gly Ser
            180                 185                 190

Asp Ser Leu Lys Gly Phe Lys Asp Ile Leu Ser Thr Lys Lys Phe Asn
        195                 200                 205

Lys Val Phe Pro Lys Leu Ser Leu Pro Met Asp Lys Glu Ile Arg Arg
    210                 215                 220

Ala Tyr Arg Gly Gly Phe Thr Trp Leu Asn Asp Lys Tyr Lys Glu Lys
225                 230                 235                 240

Glu Ile Gly Glu Gly Met Val Phe Asp Val Asn Ser Met Tyr Pro Ala
                245                 250                 255

Met Met Lys Asn Lys Leu Leu Pro Tyr Gly Glu Pro Val Met Phe Lys
            260                 265                 270

Gly Glu Tyr Lys Lys Asn Val Glu Tyr Pro Leu Tyr Ile Gln Gln Val
        275                 280                 285

Arg Cys Phe Phe Glu Leu Lys Lys Asp Lys Ile Pro Cys Ile Gln Ile
```

```
            290                 295                 300
Lys Gly Asn Ala Arg Phe Gly Gln Asn Glu Tyr Leu Ser Thr Ser Gly
305                 310                 315                 320

Asp Glu Tyr Val Asp Leu Tyr Val Thr Asn Val Asp Trp Glu Leu Ile
                325                 330                 335

Lys Lys His Tyr Asp Ile Phe Glu Glu Phe Ile Gly Gly Phe Met
            340                 345                 350

Phe Lys Gly Phe Ile Gly Phe Asp Glu Tyr Ile Asp Arg Phe Phe
                355                 360                 365

Glu Ile Lys Asn Ser Pro Tyr Ser Ser Ala Lys Gln Ser Leu Gln Ala
370                 375                 380

Lys Leu Met Leu Asn Ser Leu Tyr Gly Lys Phe Ala Thr Asn Pro Asp
385                 390                 395                 400

Val Thr Gly Lys Val Pro Tyr Leu Lys Glu Asn Gly Ala Leu Gly Phe
                405                 410                 415

Arg Leu Gly Glu Glu Glu Thr Lys Asp Pro Val Tyr Thr Pro Met Gly
                420                 425                 430

Val Phe Ile Thr Ala Trp Ala Arg Phe Thr Thr Ile Thr Ala Ala Gln
                435                 440                 445

Ala Cys Tyr Asp Arg Ile Ile Tyr Cys Asp Thr Asp Ser Ile His Leu
    450                 455                 460

Thr Gly Thr Glu Val Pro Glu Ile Ile Lys Asp Ile Val Asp Pro Lys
465                 470                 475                 480

Lys Leu Gly Tyr Trp Ala His Glu Ser Thr Phe Lys Arg Ala Lys Tyr
                485                 490                 495

Leu Arg Gln Lys Thr Tyr Ile Gln Asp Ile Tyr Val Lys Glu Val Asp
                500                 505                 510

Gly Tyr Leu Lys Glu Cys Ser Pro Asp Glu Ala Thr Thr Thr Lys Phe
                515                 520                 525

Ser Val Lys Cys Ala Gly Met Thr Asp Thr Ile Lys Lys Lys Val Thr
                530                 535                 540

Phe Asp Asn Phe Arg Val Gly Phe Ser Ser Thr Gly Lys Pro Lys Pro
545                 550                 555                 560

Val Gln Val Asn Gly Gly Val Val Leu Val Asp Ser Val Phe Thr Ile
                565                 570                 575

Lys

<210> SEQ ID NO 12
<211> LENGTH: 575
<212> TYPE: PRT
<213> ORGANISM: Artificial Sequence
<220> FEATURE:
<223> OTHER INFORMATION: Chimeric DNA polymerase mutant 1094P.  Derived
      from the polymerases encoded by SEQ ID NOs: 2-6.

<400> SEQUENCE: 12

Met Lys His Met Pro Arg Lys Met Tyr Ser Cys Asp Phe Glu Thr Thr
1               5                   10                  15

Thr Lys Val Glu Asp Cys Arg Val Trp Ala Tyr Gly Tyr Met Asn Ile
                20                  25                  30

Glu Asp His Ser Glu Tyr Lys Ile Gly Asn Ser Leu Asp Glu Phe Met
            35                  40                  45

Ala Trp Val Leu Lys Val Gln Ala Asp Leu Tyr Phe His Asp Leu Lys
50                  55                  60

Phe Asp Gly Ala Phe Ile Ile Asn Trp Leu Glu Arg Asn Gly Phe Lys
```

-continued

```
            65                  70                  75                  80
       Trp Ser Ala Asp Gly Leu Pro Asn Thr Tyr Asn Thr Ile Ile Ser Arg
                           85                  90                  95
       Met Gly Gln Trp Tyr Met Ile Asp Ile Cys Leu Gly Tyr Lys Gly Lys
                          100                 105                 110
       Arg Lys Ile His Thr Val Ile Tyr Asp Ser Leu Lys Lys Leu Pro Phe
                          115                 120                 125
       Pro Val Lys Lys Ile Ala Lys Asp Phe Gln Leu Pro Leu Leu Lys Gly
                          130                 135                 140
       Asp Ile Asp Tyr His Ala Glu Arg Pro Val Gly His Glu Ile Thr Pro
       145                 150                 155                 160
       Glu Glu Tyr Glu Tyr Ile Lys Asn Asp Ile Glu Ile Ala Arg Ala
                          165                 170                 175
       Leu Asp Ile Gln Phe Lys Gln Gly Leu Asp Arg Met Thr Ala Gly Ser
                          180                 185                 190
       Asp Ser Leu Lys Gly Phe Lys Asp Ile Leu Ser Thr Lys Lys Phe Asn
                          195                 200                 205
       Lys Val Phe Pro Lys Leu Ser Leu Pro Met Asp Lys Glu Ile Arg Arg
       210                 215                 220
       Ala Tyr Arg Gly Gly Phe Thr Trp Leu Asn Asp Lys Tyr Lys Glu Lys
       225                 230                 235                 240
       Glu Ile Gly Glu Gly Met Val Phe Asp Val Asn Ser Met Tyr Pro Ala
                          245                 250                 255
       Met Met Lys Asn Lys Leu Leu Pro Tyr Gly Glu Pro Val Met Phe Lys
                          260                 265                 270
       Gly Glu Tyr Lys Lys Asn Val Glu Tyr Pro Leu Tyr Ile Gln Gln Val
                          275                 280                 285
       Arg Cys Phe Phe Glu Leu Lys Lys Asp Lys Ile Pro Cys Ile Gln Ile
                          290                 295                 300
       Lys Gly Asn Ala Arg Phe Gly Gln Asn Glu Tyr Leu Ser Thr Ser Gly
       305                 310                 315                 320
       Asp Glu Tyr Val Asp Leu Tyr Val Thr Asn Val Asp Trp Glu Leu Ile
                          325                 330                 335
       Lys Lys His Tyr Asp Ile Phe Glu Glu Phe Ile Gly Gly Phe Met
                          340                 345                 350
       Phe Lys Gly Phe Ile Gly Phe Asp Glu Tyr Ile Asp Arg Phe Phe
                          355                 360                 365
       Glu Ile Lys Asn Ser Pro Tyr Ser Ser Ala Lys Gln Leu Ala Lys Leu
                          370                 375                 380
       Met Leu Asn Ser Leu Tyr Gly Lys Phe Ala Thr Asn Pro Asp Val Thr
       385                 390                 395                 400
       Gly Lys Val Pro Tyr Leu Lys Glu Asn Gly Ala Leu Gly Phe Arg Leu
                          405                 410                 415
       Gly Glu Glu Thr Lys Asp Pro Val Tyr Thr Pro Met Gly Val Phe
                          420                 425                 430
       Ile Thr Ala Trp Ala Arg Phe Thr Thr Ile Thr Ala Ala Gln Ala Cys
                          435                 440                 445
       Tyr Asp Arg Ile Ile Tyr Cys Asp Thr Asp Ser Ile His Leu Thr Gly
                          450                 455                 460
       Thr Glu Val Pro Glu Ile Ile Lys Asp Ile Val Asp Pro Lys Lys Leu
       465                 470                 475                 480
       Gly Tyr Trp Ala His Glu Ser Thr Phe Lys Arg Ala Lys Tyr Leu Arg
                          485                 490                 495
```

```
Gln Lys Thr Tyr Ile Gln Asp Ile Tyr Val Lys Glu Val Asp Gly Tyr
            500                 505                 510
Leu Lys Glu Cys Ser Pro Asp Glu Ala Thr Thr Thr Lys Phe Ser Val
        515                 520                 525
Lys Cys Ala Gly Met Thr Asp Thr Ile Lys Lys Val Thr Phe Asp
    530                 535                 540
Asn Phe Arg Val Gly Phe Ser Ser Thr Gly Lys Pro Lys Pro Val Gln
545                 550                 555                 560
Val Asn Gly Gly Val Val Leu Val Asp Ser Val Phe Thr Ile Lys
                565                 570                 575

<210> SEQ ID NO 13
<211> LENGTH: 1728
<212> TYPE: DNA
<213> ORGANISM: Artificial Sequence
<220> FEATURE:
<223> OTHER INFORMATION: Phi29-derived DNA polymerase mutant 290P.

<400> SEQUENCE: 13
atgaaacaca tgccacgtaa aatgtattcc tgcgactttg agactaccac caaggttgaa      60
gattgccgcg tatgggcata cggttacatg aacatcgaag accactccga gtataagatt     120
ggtaactccc tggatgaatt tatggcttgg gttctgaaag ttcaggctga cctgtacttc     180
cacgatctga aatttgatgg cgcattcatc atcaactggc tggaacgtaa cggttttaaa     240
tggtccgcag atggtctgcc aaatacctac aacaccatca tttctcgcat gggccagtgg     300
tatatgatta atatttgcct gggttacaag ggtaaacgca agatccacac cgtgatctac     360
gactctctga agaaactgcc gtttccggtt aagaaaattg cgaaagactt taagctgacg     420
gtactgaaag cgacatcga ctatcataag gagcgcccgg tcggttacaa aatcaccccg     480
gaagaatatg cctacattaa aaacgatatt cagattatcg cagaagctct gctgatccag     540
ttcaagcagg gtctggatcg tatgacggca ggttctgact ctctgaaagg cttcaaagac     600
attatcacca ccaagaagtt taaaaaggtt tcccgacccc tgagcctggg tctggacaag     660
gaagttcgtt atgcctaccg tggtggtttc acctggctga tgaccgtttt taagaaaaaa     720
gagatcggcg aaggtatggt ttttgatgtt aattccctgt acccagcgca aatgtactct     780
cgcctgctgc gtacggcga gccgatcgta ttcgagggta atacgtctg ggacgaggac     840
tacctctgc acattcagca cattcgttgt gaatttgaac tgaaggaagg ctacatcccg     900
accatccaga tcaagcgttc ccgtttctac aagggtaacg aatacctgaa atcttccggc     960
ggtgaaattg ctgacctgtg ctgtctaat gttgatctgg aactgatgaa agagcactac    1020
gacctgtaca atgttgaata tctctctggt ctgaagttca agcaaccac tggcctgttc    1080
aaggactta tcgacaaatg gacgtatatc aaaactacct ctgaaggcgc catcaaacag    1140
ctggcgaagc tgatgctgaa cagcctgtac ggtaaattcg cgtccaaccc ggacgttacc    1200
ggtaaagtgc cataccgtga agagaacggt gctctgggtt ttcgtctggg tgaggaggaa    1260
acgaaagacc ctgtatatac cccgatgggt gtctttatca cggcctgggc acgctatacg    1320
accatcacgg cagcgcaggc ttgttatgat cgtattatct actgcgatac cgattctatt    1380
cacctgactg gtactgaaat tccggacgtt atcaaagaca tcgtagaccc gaagaaactg    1440
ggctactggg cgcacgaatc cacttttaag cgtgcaaaat atctgcgtca gaaaacctac    1500
atccaggata tttacatgaa agaagtagac ggcaaactgg tagagggctc tcctgacgac    1560
tacactgaca tcaagttctc tgtgaaatgc gcaggcatga cggacaaaat caaaaaggaa    1620
```

```
gtgactttcg aaaacttcaa agtgggtttt tctcgtaaaa tgaaaccgaa gcctgttcag    1680
gtaccgggtg gcgtagtgct ggttgatgac acttttacta tcaaataa                 1728
```

<210> SEQ ID NO 14
<211> LENGTH: 1728
<212> TYPE: DNA
<213> ORGANISM: Artificial Sequence
<220> FEATURE:
<223> OTHER INFORMATION: Phi29-derived DNA polymerase mutant 587P.

<400> SEQUENCE: 14

```
atgaaacaca tgccacgtaa aatgtattcc tgcgactttg agactaccac caaggttgaa     60
gattgccgcg tatgggcata cggttacatg aacatcgaag accactccga gtataagatt    120
ggtaactccc tggatgaatt tatggcttgg gttctgaaag ttcaggctga cctgtacttc    180
cacgatctga aatttgatgg cgcattcatc atcaactggc tggaacgtaa cggttttaaa    240
tggtccgcag atggtctgcc aaataccttac aacaccatca tttctcgcat gggccagtgg    300
tatatgattg atatttgcct gggttacaag ggtaaacgca agatccacac cgtgatctac    360
gactctctga gaaaactgcc gtttccggtt aagaaaattg cgaaagactt taagctgacg    420
gtactgaaag gcgacatcga ctatcataag gagcgcccgg tcggttacaa aatcaccccg    480
gaagaatatg cctacattaa aaacgatatt cagattatcg cagaagctct gctgatccag    540
ttcaagcagg gtctggatcg tatgacggca ggttctgact ctctgaaagg cttcaaagac    600
attatcacca ccaagaagtt taaaaaggtt ttcccgacccc tgagcctggg tctggacaag    660
gaagttcgtt atgcctaccg tggtggtttc acctggctga atgaccgttt taagaaaaaa    720
gagatcggcg aaggtatggt ttttgatgtt aattccctgt acccagcgca aatgtactct    780
cgcctgctgc cgtacggcga gccgatcgta ttcgagggta aatacgtctg ggacgaggac    840 tacccctctgc acattcagca cattcgttgt gaatttgaac tgaaggaagg ctacatcccg    900
accatccaga tcaagcgttc ccgtttctac aagggtaacg aatacctgaa atcttccggc    960
ggtgaaattg ctgacctgtg gctgtctaat gttgatctgg aactgatgaa agagcactac   1020
gacctgtaca atgttgaata tatctctggt ctgaagttca aagcaaccac tggcctgttc   1080
aaggacttta tcgacaaatg gacgtatatc aaaactacct ctgaaggcgc catcaaacag   1140
ctggcgaagc tgatgctgaa cagcctgtac ggtaaattcg cgtccaaccc ggacgttacc   1200
ggtaaagtgc catacctgaa agagaacggt gctctgggtt ttcgtctggg tgaggaggaa   1260
acgaaagacc ctgtatatac cccgatgggt gtctttatca cggcctgggc acgctatacg   1320
accatcacgg cagcgcaggc ttgttatgat cgtattatct actgcgatac cgattctatt   1380
cacctgactg gtactgaaat tccggacgtt atcaaagaca tcgtagaccc gaagaaactg   1440
ggctacagcg cgcacgaatc cacttttaag cgtgcaaaat atctgcgtca gaaaacctac   1500
atccaggata tttacatgaa agaagtagac ggcaaactgg tagagggctc tcctgacgac   1560
tacactgaca tcaagttctc tgtgaaatgc gcaggcatga cggacaaaat caaaaaggaa   1620
gtgactttcg aaaacttcaa agtgggtttt tctcgtaaaa tgaaaccgaa gcctgttcag   1680
gtaccgggtg gcgtagtgct ggttgatgac acttttacta tcaaataa                 1728
```

<210> SEQ ID NO 15
<211> LENGTH: 1728
<212> TYPE: DNA
<213> ORGANISM: Artificial Sequence
<220> FEATURE:

<223> OTHER INFORMATION: Phi29-derived DNA polymerase mutant 596P.

<400> SEQUENCE: 15

| | |
|---|---|
| atgaaacaca tgccacgtaa aatgtattcc tgcgactttg agactaccac caaggttgaa | 60 |
| gattgccgcg tatgggcata cggttacatg aacatcgaag accactccga gtataagatt | 120 |
| ggtaactccc tggatgaatt tatggcttgg gttctgaaag ttcaggctga cctgtacttc | 180 |
| cacgatctga aatttgatgg cgcattcatc atcaactggc tggaacgtaa cggttttaaa | 240 |
| tggtccgcag atggtctgcc aaatacctac aacaccatca tttctcgcat gggccagtgg | 300 |
| tatatgattg atatttgcct gggttacaag ggtaaacgca agatccacac cgtgatctac | 360 |
| gactctctga gaaactgcc gtttccggtt aagaaaattg cgaaagactt taagctgacg | 420 |
| gtactgaaag cgacatcga ctatcataag gagcgcccgg tcggttacaa aatcaccccg | 480 |
| gaagaatatg cctacattaa aaacgatatt cagattatcg cagaagctct gctgatccag | 540 |
| ttcaagcagg tctggatcg tatgacggca ggttctgact ctctgaaagg cttcaaagac | 600 |
| attatcacca ccaagaagtt taaaaaggtt tccccgaccc tgagcctggg tctggacaag | 660 |
| gaagttcgtt atgcctaccg tggtggtttc acctggctga tgaccgtttt aaagaaaaaa | 720 |
| gagatcggcg aaggtatggt ttttgatgtt aattccctgt acccagcgca aatgtactct | 780 |
| cgcctgctgc cgtacggcga ccgatcgta ttcgaggta aatacgtctg gacgaggac | 840 |
| taccctctgc acattcagca cattcgttgt gaatttgaac tgaaggaagg ctacatcccg | 900 |
| accatccaga tcaagcgttc ccgtttctac aagggtaacg aatacctgaa atcttccggc | 960 |
| ggtgaaattg ctgacctgtg ctgtctaat gttgatctgg aactgatgaa agagcactac | 1020 |
| gacctgtaca atgttgaata tatctctggt ctgaagttca agcaaccac tggcctgttc | 1080 |
| aaggacttta tcgacaaatg gacgtatatc aaaaactacct tgaaggcgc catcaaacag | 1140 |
| ctggcgaagc tgatgctgaa cagcctgtac ggtaaattcg cgtccaaccc ggacgttacc | 1200 |
| ggtaaagtgc catacctgaa agagaacggt gctctgggtt tcgtctgggt gaggaggaa | 1260 |
| acgaaagacc ctgtatatac cccgatgggt gtctttatca cggcctgggc acgctatacg | 1320 |
| accatcacgg cagcgcaggc ttgttatgat cgtattatct actgcgatac cgattctatt | 1380 |
| cacctgactg gtactgaaat tccggacgtt atcaaagaca tcgtagaccc gaagaaactg | 1440 |
| ggctactggg cgcacgaatc cacttttaag cgtgcaaaat atctgcgtca gaaaacctac | 1500 |
| atccaggata tttacatgaa agaagtagac ggcaaactgg tagagggctc tcctgacgac | 1560 |
| tacactgaca tcaagctgtc tgtgaaatgc gcaggcatga cggacaaaat caaaaaggaa | 1620 |
| gtgactttcg aaaacttcaa agtgggtttt tctcgtaaaa tgaaaccgaa gcctgttcag | 1680 |
| gtaccgggtg gcgtagtgct ggttgatgac acttttacta tcaaataa | 1728 |

<210> SEQ ID NO 16
<211> LENGTH: 1734
<212> TYPE: DNA
<213> ORGANISM: Artificial Sequence
<220> FEATURE:
<223> OTHER INFORMATION: Chimeric DNA polymerase mutant 604P.

<400> SEQUENCE: 16

| | |
|---|---|
| atgaaacaca tgccacgtaa aatgtattcc tgcgactttg agactaccac caaggttgaa | 60 |
| gattgccgcg tatgggcata cggttacatg aacatcgaag accactccga gtataagatt | 120 |
| ggtaactccc tggatgaatt tatggcttgg gttctgaaag ttcaggctga cctgtacttc | 180 |
| cacgatctga aatttgatgg cgcattcatc atcaactggc tggaacgtaa cggttttaaa | 240 |

```
tggtccgcag atggtctgcc aaatacctac aacaccatca tttctcgcat gggccagtgg      300
tatatgattg atatttgcct gggttacaag ggtaaacgca agatccacac cgtgatctac      360
gactctctga agaaactgcc gtttccggtt aagaaaattg cgaaagactt tcagctgcca      420
ctgctgaaag cgacatcga ctatcatgct gagcgcccgg tcggtcatga gatcaccccg       480
gaagaatatg aatacattaa aaacgatatt gaaattatcg cacgcgctct ggacatccag      540
ttcaagcagg tctggatcg tatgacggca ggttctgact ctctgaaagg cttcaaagac       600
attctgtcta ccaagaagtt taacaaagtt ttcccgaaac tgagcctgcc gatggacaag      660
gaaatccgtc gtgcctaccg tggtggtttc acctggctga atgacaaata caagaaaaaa      720
gagatcggcg aaggtatggt ttttgatgtt aattccatgt acccagcgat gatgaaaaac      780
aaactgctgc gtacggcga ccgtaatg ttcaaaggcg agtacaagaa aaacgtcgag         840
taccctctgt acattcagca ggtgcgttgt ttctttgaac tgaagaaaga caagatcccg      900
tgcatccaga tcaagggcaa cgcacgtttc ggtcaaaacg aatacctgtc tacctccggc      960
gacgaatacg tggacctgta cgtgactaat gttgattggg aactgatcaa gaaacactac     1020
gacattttcg aagaagagtt catcggcggt tttatgttca agggcttcat tggcttcttc     1080
gacgaataca tcgaccgttt catggaaatc aaaaactctc cagactcctc tgctgaacag     1140
agcctgcaag cgaagctgat gctgaacagc ctgtacggta aattcgcgac caacccggac     1200
gttaccggta aagtgccata cctgaaagag aacggtgctc tgggttttcg tctgggtgag     1260
gaggaaacga aagaccctgt atataccccg atgggtgtct ttatcacggc ctgggcacgc     1320
ttcacgacca tcacggcagc gcaggcttgt tatgatcgta ttatctactg cgataccgat     1380
tctattcacc tgactggtac tgaggttccg gaaattatca agacatcgt agacccgaag      1440 aaactgggct actgggcgca cgaatccact tttaagcgtg caaaatatct gcgtcagaaa     1500
acctacatcc aggatattta cgttaaagaa gtagacggca aactgaaaga gtgttctcct     1560
gacgaagcta ccactactaa gttctctgtg aaatgcgcag gcatgacgga caccatcaaa     1620
aagaaggtga cttctgacaa cttccgtgtg ggttttttcct ctactggcaa accgaagcct     1680
gttcaggtaa acggtggcgt agtgctggtt gattctgttt tactatcaa ataa             1734
```

<210> SEQ ID NO 17  
<211> LENGTH: 1719  
<212> TYPE: DNA  
<213> ORGANISM: Artificial Sequence  
<220> FEATURE:  
<223> OTHER INFORMATION: Chimeric DNA polymerase mutant 605P.

<400> SEQUENCE: 17

```
atggcacgtt ctgtttatgt atgcgacttt gagactacca ccgatccgga agattgccgc       60
ctgtgggcat ggggttggat ggatatctac aacactgaca aatggtccta cggtgaggac      120
attgactcct ttatggagtg ggctctgaat agcaattccg acatttactt ccacgatctg      180
aaatttgatg cgcattcat catcaactgg ctggaacgta acggttttaa atggtccgca       240
gatggtctgc caaatacacta caacaccatc atttctcgca tgggccagtg gtatatgatt     300
gatatttgcc tgggttacaa gggtaaacgc aagatccaca ccgtgatcta cgactctctg      360
aagaaactgc cgtttaaagt tgagcagatt gcgaaaggtt ttggcctgcc agtactgaaa      420
ggcgacatcg actataaaaa gtaccgcccg gtcggttacg ttatggatga taacgaaatc      480
gaatatctga aacacgatct gctgattgtt gcactggctc tgcgtagcat gttcgacaac      540
```

-continued

```
gatttcactt ctatgacggt tggttctgac gctctgaaca cctacaaaga aatgctgggc      600
gttaaacagt gggaaaagta ctttccggtt ctgagcctga aggttaactc cgaaatccgt      660
aaagcctaca aggtggtttt cacctgggta atccgaaat atcagggtga aactgtatat       720
ggcggtatgg tttttgatgt taattccctg tacccagcgc aaatgtactc tcgcctgctg      780
ccgtacggcg agccgatcgt attcgagggt aaatacgtct gggacgagga ctaccctctg     840
cacattcagc acattcgttg tgaatttgaa ctgaaggaag ctacatccc gaccatccag       900 atcaagcgtt cccgtttcta caagggtaac gaatacctga atcttccgg cggtgaaatt      960 gctgacctgt ggctgtctaa tgttgatctg gaactgatga agagcacta cgacctgtac     1020 aatgttgaat atatctctgg tctgaagttc aaagcaacca ctggcctgtt caaggacttt    1080
atcgacaaat ggacgtatat caaaactacc tctgaaggcg ccatcaaaca gctggcgaag    1140
ctgatgctga acagcctgta cggtaaattc gcgtccaacc cggacgttac cggtaaagtg    1200
ccatacctga agaggatgg ttccctgggt tttcgtgttg gtgatgagga gtacaaagac     1260
cctgtatata ccccgatggg tgtctttatc acggcctggg cacgcttcac gaccatcacg    1320
gcagcgcagg cttgttatga tcgtattatc tactgcgata ccgattctat tcacctgact    1380
ggtactgaag tgccggaaat tatcaaagac atcgtagacc cgaagaaact gggctactgg    1440
gcgcacgaat ccacttttaa gcgtgcaaaa tatctgcgtc agaaaaccta catccaggat    1500
atttacgcca agaagtaga cggcaaactg attgagtgtt ctcctgacga agcgacgacc    1560
actaagttct ctgtgaaatg cgcaggcatg acggacacca tcaaaaagaa ggtgactttc    1620
gacaacttcc gtgtgggttt ttcctctact ggcaaaccga agcctgttca ggtaaacggt    1680
ggcgtagtgc tggttgattc tgttttttact atcaaataa                           1719
```

<210> SEQ ID NO 18
<211> LENGTH: 1734
<212> TYPE: DNA
<213> ORGANISM: Artificial Sequence
<220> FEATURE:
<223> OTHER INFORMATION: Chimeric DNA polymerase mutant 1093P.

<400> SEQUENCE: 18

```
atgaaacaca tgccacgtaa aatgtattcc tgcgactttg agactaccac caaggttgaa      60
gattgccgcg tatgggcata cggttacatg aacatcgaag accactccga gtataagatt     120
ggtaactccc tggatgaatt tatggcttgg gttctgaaag ttcaggctga cctgtacttc     180
cacgatctga aatttgatgg cgcattcatc atcaactggc tggaacgtaa cggttttaaa     240
tggtccgcag atggtctgcc aaatacctac aacaccatca tttctcgcat gggccagtgg     300
tatatgattg atatttgcct gggttacaag ggtaaacgca agatccacac cgtgatctac     360
gactctctga gaaactgcc gtttccggtt aagaaaattg cgaaagactt tcagctgcca     420
ctgctgaaag cgacatcga ctatcatgct gagcgcccgg tcgtcatga atcaccccg       480 gaagaatatg aatacattaa aaacgatatt gaaattatcg cacgcgctct ggacatccag    540
ttcaagcagg gtctggatcg tatgacggca ggttctgact ctctgaaagg cttcaaagac    600
attctgtcta ccaagaagtt taacaaagtt ttcccgaaac tgagcctgcc gatggacaag    660
gaaatccgtc gtgcctaccg tggtggtttc acctggctga tgacaaata caagaaaaa     720 gagatcggcg aaggtatggt ttttgatgtt aattccatgt acccagcgat gatgaaaaac    780
aaactgctgc cgtacggcga gccggtaatg ttcaaaggcg agtacaagaa aaacgtcgag    840
taccctctgt acattcagca ggtgcgttgt ttctttgaac tgaagaaaga caagatcccg    900
```

```
tgcatccaga tcaagggcaa cgcacgtttc ggtcaaaacg aatacctgtc tacctccggc    960
gacgaatacg tggacctgta cgtgactaat gttgattggg aactgatcaa gaaacactac   1020
gacattttcg aagaagagtt catcggcggt tttatgttca agggcttcat tggcttcttc   1080
gacgaataca tcgaccgttt cttcgaaatc aaaaactctc catattcctc tgctaagcag   1140
agcctgcaag cgaagctgat gctgaacagc ctgtacggta aattcgcgac caacccggac   1200
gttaccggta aagtgccata cctgaaagag aacggtgctc tgggttttcg tctgggtgag   1260
gaggaaacga aagaccctgt atataccccg atgggtgtct ttatcacggc ctgggcacgc   1320
ttcacgacca tcacggcagc gcaggcttgt tatgatcgta ttatctactg cgataccgat   1380
tctattcacc tgactggtac tgaggttccg gaaattatca agacatcgt agacccgaag   1440 aaactgggct actgggcgca cgaatccact tttaagcgtg caaatatct gcgtcagaaa   1500 acctacatcc aggatattta cgttaaagaa gtagacggct acctgaaaga gtgttctcct   1560
gacgaagcta ccactactaa gttctctgtg aaatgcgcag gcatgacgga caccatcaaa   1620
aagaaggtga ctttcgacaa cttccgtgtg ggttttttcct ctactggcaa accgaagcct   1680
gttcaggtaa acggtggcgt agtgctggtt gattctgttt ttactatcaa ataa          1734
```

<210> SEQ ID NO 19
<211> LENGTH: 1728
<212> TYPE: DNA
<213> ORGANISM: Artificial Sequence
<220> FEATURE:
<223> OTHER INFORMATION: Chimeric DNA polymerase mutant 1094P.

<400> SEQUENCE: 19

```
atgaaacaca tgccacgtaa aatgtattcc tgcgactttg agactaccac caaggttgaa     60
gattgccgcg tatgggcata cggttacatg aacatcgaag accactccga gtataagatt    120
ggtaactccc tggatgaatt tatggcttgg gttctgaaag ttcaggctga cctgtacttc    180
cacgatctga atttgatgg cgcattcatc atcaactggc tggaacgtaa cggttttaaa    240
tggtccgcag atggtctgcc aaataccctac aacaccatca tttctcgcat gggccagtgg    300
tatatgattg atatttgcct gggttacaag ggtaaacgca agatccacac cgtgatctac    360
gactctctga gaaaactgcc gtttccggtt aagaaaattg cgaaagactt tcagctgcca    420
ctgctgaaag cgacatcga ctatcatgct gagcgcccgg tcggtcatga gatcaccccg    480
gaagaatatg aatacattaa aaacgatatt gaaattatcg cacgcgctct ggacatccag    540
ttcaagcagg gtctggatcg tatgacggca ggttctgact ctctgaaagg cttcaaagac    600
attctgtcta ccaagaagtt taacaaagtt ttcccgaaac tgagcctgcc gatggacaag    660
gaaatccgtc gtgcctaccg tggtggtttc acctggctga tgacaaata caagaaaaaa    720 gagatcggcg aaggtatggt ttttgatgtt aattccatgt acccagcgat gatgaaaaac    780
aaactgctgc cgtacggcga gccggtaatg ttcaaaggcg agtacaagaa aaacgtcgag    840
taccctctgt acattcagca ggtgcgttgt ttctttgaac tgaagaaaga caagatcccg    900
tgcatccaga tcaagggcaa cgcacgtttc ggtcaaaacg aatacctgtc tacctccggc    960
gacgaatacg tggacctgta cgtgactaat gttgattggg aactgatcaa gaaacactac   1020
gacattttcg aagaagagtt catcggcggt tttatgttca agggcttcat tggcttcttc   1080
gacgaataca tcgaccgttt cttcgaaatc aaaaactctc catattcctc tgctaagcag   1140
ctggcgaagc tgatgctgaa cagcctgtac ggtaaattcg cgaccaaccc ggacgttacc   1200
```

```
ggtaaagtgc catacctgaa agagaacggt gctctgggtt ttcgtctggg tgaggaggaa    1260
acgaaagacc ctgtatatac cccgatgggt gtctttatca cggcctgggc acgcttcacg    1320
accatcacgg cagcgcaggc ttgttatgat cgtattatct actgcgatac cgattctatt    1380
cacctgactg gtactgaggt tccggaaatt atcaaagaca tcgtagaccc gaagaaactg    1440
ggctactggg cgcacgaatc cacttttaag cgtgcaaaat atctgcgtca gaaaacctac    1500
atccaggata tttacgttaa agaagtagac ggctacctga agagtgttc tcctgacgaa     1560 gctaccacta ctaagttctc tgtgaaatgc gcaggcatga cggacaccat caaaaagaag    1620
gtgactttcg acaacttccg tgtgggtttt tcctctactg caaaccgaa gcctgttcag     1680 gtaaacggtg gcgtagtgct ggttgattct gttttacta tcaaataa                  1728
```

<210> SEQ ID NO 20
<211> LENGTH: 575
<212> TYPE: PRT
<213> ORGANISM: Artificial Sequence
<220> FEATURE:
<223> OTHER INFORMATION: Phi29-derived DNA polymerase mutant 520P.

<400> SEQUENCE: 20

```
Met Lys His Met Pro Arg Lys Met Tyr Ser Cys Asp Phe Glu Thr Thr
1               5                   10                  15

Thr Lys Val Glu Asp Cys Arg Val Trp Ala Tyr Gly Tyr Met Asn Ile
            20                  25                  30

Glu Asp His Ser Glu Tyr Lys Ile Gly Asn Ser Leu Asp Glu Phe Met
        35                  40                  45

Ala Trp Val Leu Lys Val Gln Ala Asp Leu Tyr Phe His Asp Leu Lys
    50                  55                  60

Phe Asp Gly Ala Phe Ile Ile Asn Trp Leu Glu Arg Asn Gly Phe Lys
65                  70                  75                  80

Trp Ser Ala Asp Gly Leu Pro Asn Thr Tyr Asn Thr Ile Ile Ser Arg
                85                  90                  95

Met Gly Gln Trp Tyr Met Ile Asp Ile Cys Leu Gly Tyr Lys Gly Lys
            100                 105                 110

Arg Lys Ile His Thr Val Ile Tyr Asp Ser Leu Lys Lys Leu Pro Phe
        115                 120                 125

Pro Val Lys Lys Ile Ala Lys Asp Phe Lys Leu Thr Val Leu Lys Gly
    130                 135                 140

Asp Ile Asp Tyr His Lys Glu Arg Pro Val Gly Tyr Lys Ile Thr Pro
145                 150                 155                 160

Glu Glu Tyr Ala Tyr Ile Lys Asn Asp Ile Gln Ile Ile Ala Glu Ala
                165                 170                 175

Leu Leu Ile Gln Phe Lys Gln Gly Leu Asp Arg Met Thr Ala Gly Ser
            180                 185                 190

Asp Ser Leu Lys Gly Phe Lys Asp Ile Ile Thr Thr Lys Lys Phe Lys
        195                 200                 205

Lys Val Phe Pro Thr Leu Ser Leu Gly Leu Asp Lys Glu Val Arg Tyr
    210                 215                 220

Ala Tyr Arg Gly Gly Phe Thr Trp Leu Asn Asp Arg Phe Lys Glu Lys
225                 230                 235                 240

Glu Ile Gly Glu Gly Met Val Phe Asp Val Asn Ser Leu Tyr Pro Ala
                245                 250                 255

Gln Met Tyr Ser Arg Leu Leu Pro Tyr Gly Glu Pro Ile Val Phe Glu
            260                 265                 270
```

```
Gly Lys Tyr Val Trp Asp Glu Asp Tyr Pro Leu His Ile Gln His Ile
            275                 280                 285
Arg Cys Glu Phe Glu Leu Lys Glu Gly Tyr Ile Pro Thr Ile Gln Ile
        290                 295                 300
Lys Arg Ser Arg Phe Tyr Lys Gly Asn Glu Tyr Leu Lys Ser Ser Gly
305                 310                 315                 320
Gly Glu Ile Ala Asp Leu Trp Leu Ser Asn Val Asp Leu Glu Leu Met
                325                 330                 335
Lys Glu His Tyr Asp Leu Tyr Asn Val Glu Tyr Ile Ser Gly Leu Lys
            340                 345                 350
Phe Lys Ala Thr Thr Gly Leu Phe Lys Asp Phe Ile Asp Lys Trp Phe
        355                 360                 365
Tyr Ile Lys Thr Thr Ser Tyr Gly Ala Ile Lys Gln Leu Ala Lys Leu
    370                 375                 380
Met Leu Asn Ser Leu Tyr Gly Lys Phe Ala Ser Asn Pro Asp Val Thr
385                 390                 395                 400
Gly Lys Val Pro Tyr Leu Lys Glu Asn Gly Ala Leu Gly Phe Arg Leu
                405                 410                 415
Gly Glu Glu Glu Thr Lys Asp Pro Val Tyr Thr Pro Met Gly Val Phe
            420                 425                 430
Ile Thr Ala Trp Ala Arg Tyr Thr Thr Ile Thr Ala Ala Gln Ala Cys
        435                 440                 445
Tyr Asp Arg Ile Ile Tyr Cys Asp Thr Asp Ser Ile His Leu Thr Gly
    450                 455                 460
Thr Glu Ile Pro Asp Val Ile Lys Asp Ile Val Asp Pro Lys Lys Leu
465                 470                 475                 480
Gly Tyr Trp Ala His Glu Ser Thr Phe Lys Arg Ala Lys Tyr Leu Arg
                485                 490                 495
Gln Lys Thr Tyr Ile Gln Asp Ile Tyr Met Lys Glu Val Asp Gly Tyr
            500                 505                 510
Leu Val Glu Gly Ser Pro Asp Asp Tyr Thr Asp Ile Lys Phe Ser Val
        515                 520                 525
Lys Cys Ala Gly Met Thr Asp Lys Ile Lys Lys Glu Val Thr Phe Glu
    530                 535                 540
Asn Phe Lys Val Gly Phe Ser Arg Lys Met Lys Pro Lys Pro Val Gln
545                 550                 555                 560
Val Pro Gly Gly Val Val Leu Val Asp Asp Thr Phe Thr Ile Lys
                565                 570                 575

<210> SEQ ID NO 21
<211> LENGTH: 572
<212> TYPE: PRT
<213> ORGANISM: Bacteriophage M2

<400> SEQUENCE: 21

Met Ser Arg Lys Met Phe Ser Cys Asp Phe Glu Thr Thr Thr Lys Leu
1               5                   10                  15
Asp Asp Cys Arg Val Trp Ala Tyr Gly Tyr Met Glu Ile Gly Asn Leu
            20                  25                  30
Asp Asn Tyr Lys Ile Gly Asn Ser Leu Asp Glu Phe Met Gln Trp Val
        35                  40                  45
Met Glu Ile Gln Ala Asp Leu Tyr Phe His Asn Leu Lys Phe Asp Gly
    50                  55                  60
Ala Phe Ile Val Asn Trp Leu Glu Gln His Gly Phe Lys Trp Ser Asn
65                  70                  75                  80
```

```
Glu Gly Leu Pro Asn Thr Tyr Asn Thr Ile Ile Ser Lys Met Gly Gln
                85                  90                  95

Trp Tyr Met Ile Asp Ile Cys Phe Gly Tyr Lys Gly Lys Arg Lys Leu
            100                 105                 110

His Thr Val Ile Tyr Asp Ser Leu Lys Lys Leu Pro Phe Pro Val Lys
        115                 120                 125

Lys Ile Ala Lys Asp Phe Gln Leu Pro Leu Lys Gly Asp Ile Asp
    130                 135                 140

Tyr His Thr Glu Arg Pro Val Gly His Glu Ile Thr Pro Glu Glu Tyr
145                 150                 155                 160

Glu Tyr Ile Lys Asn Asp Ile Glu Ile Ala Arg Ala Leu Asp Ile
                165                 170                 175

Gln Phe Lys Gln Gly Leu Asp Arg Met Thr Ala Gly Ser Asp Ser Leu
                180                 185                 190

Lys Gly Phe Lys Asp Ile Leu Ser Thr Lys Lys Phe Asn Lys Val Phe
                195                 200                 205

Pro Lys Leu Ser Leu Pro Met Asp Lys Glu Ile Arg Lys Ala Tyr Arg
        210                 215                 220

Gly Gly Phe Thr Trp Leu Asn Asp Lys Tyr Lys Glu Lys Glu Ile Gly
225                 230                 235                 240

Glu Gly Met Val Phe Asp Val Asn Ser Leu Tyr Pro Ser Gln Met Tyr
                245                 250                 255

Ser Arg Pro Leu Pro Tyr Gly Ala Pro Ile Val Phe Gln Gly Lys Tyr
                260                 265                 270

Glu Lys Asp Glu Gln Tyr Pro Leu Tyr Ile Gln Arg Ile Arg Phe Glu
            275                 280                 285

Phe Glu Leu Lys Glu Gly Tyr Ile Pro Thr Ile Gln Ile Lys Lys Asn
        290                 295                 300

Pro Phe Phe Lys Gly Asn Glu Tyr Leu Lys Asn Ser Gly Val Glu Pro
305                 310                 315                 320

Val Glu Leu Tyr Leu Thr Asn Val Asp Leu Glu Leu Ile Gln Glu His
                325                 330                 335

Tyr Glu Leu Tyr Asn Val Glu Tyr Ile Asp Gly Phe Lys Phe Arg Glu
                340                 345                 350

Lys Thr Gly Leu Phe Lys Asp Phe Ile Asp Lys Trp Thr Tyr Val Lys
        355                 360                 365

Thr His Glu Glu Gly Ala Lys Lys Gln Leu Ala Lys Leu Met Leu Asn
    370                 375                 380

Ser Leu Tyr Gly Lys Phe Ala Ser Asn Pro Asp Val Thr Gly Lys Val
385                 390                 395                 400

Pro Tyr Leu Lys Asp Asp Gly Ser Leu Gly Phe Arg Val Gly Asp Glu
                405                 410                 415

Glu Tyr Lys Asp Pro Val Tyr Thr Pro Met Gly Val Phe Ile Thr Ala
            420                 425                 430

Trp Ala Arg Phe Thr Thr Ile Thr Ala Ala Gln Ala Cys Tyr Asp Arg
        435                 440                 445

Ile Ile Tyr Cys Asp Thr Asp Ser Ile His Leu Thr Gly Thr Glu Val
    450                 455                 460

Pro Glu Ile Ile Lys Asp Ile Val Asp Pro Lys Lys Leu Gly Tyr Trp
465                 470                 475                 480

Ala His Glu Ser Thr Phe Lys Arg Ala Lys Tyr Leu Arg Gln Lys Thr
                485                 490                 495
```

-continued

```
Tyr Ile Gln Asp Ile Tyr Val Lys Glu Val Asp Gly Lys Leu Lys Glu
            500             505             510

Cys Ser Pro Asp Glu Ala Thr Thr Thr Lys Phe Ser Val Lys Cys Ala
            515             520             525

Gly Met Thr Asp Thr Ile Lys Lys Lys Val Thr Phe Asp Asn Phe Ala
            530             535             540

Val Gly Phe Ser Ser Met Gly Lys Pro Lys Pro Val Gln Val Asn Gly
545                 550             555                 560

Gly Val Val Leu Val Asp Ser Val Phe Thr Ile Lys
                565             570
```